United States Patent
Liu et al.

(10) Patent No.: US 7,399,743 B2
(45) Date of Patent: Jul. 15, 2008

(54) TARGETED THROMBOSIS

(75) Inventors: Cheng Liu, Carlsbad, CA (US); Thomas S. Edgington, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 245 days.

(21) Appl. No.: 10/279,733

(22) Filed: Oct. 24, 2002

(65) Prior Publication Data

US 2003/0194400 A1    Oct. 16, 2003

Related U.S. Application Data

(60) Provisional application No. 60/412,194, filed on Sep. 20, 2002, provisional application No. 60/336,331, filed on Oct. 26, 2001.

(51) Int. Cl.
*A61K 38/16* (2006.01)
*A61K 38/36* (2006.01)
(52) U.S. Cl. ........................................ 514/12
(58) Field of Classification Search ................ 530/350, 530/388.22; 424/143.1; 350/530, 388.22; 514/12
See application file for complete search history.

(56) References Cited

U.S. PATENT DOCUMENTS

| | | | |
|---|---|---|---|
| 4,196,265 A | 4/1980 | Koprowski et al. | 435/2 |
| 4,554,101 A | 11/1985 | Hopp | 260/112.5 |
| 4,938,949 A | 7/1990 | Borch et al. | 424/10 |
| 4,975,369 A | 12/1990 | Beavers et al. | 435/69.1 |
| 5,017,556 A | 5/1991 | O'Brien et al. | 514/2 |
| 5,110,730 A | 5/1992 | Edgington et al. | 435/69.6 |
| 5,139,941 A | 8/1992 | Muzyczka et al. | 435/172.3 |
| 5,183,756 A | 2/1993 | Schlom | 435/240.27 |
| 5,223,427 A | 6/1993 | Edgington et al. | 435/240.27 |
| 5,242,813 A | 9/1993 | Pastan et al. | 435/70.21 |
| 5,288,641 A | 2/1994 | Roizman | 435/320.1 |
| 5,346,991 A | 9/1994 | Roy et al. | 530/350 |
| 5,374,617 A | 12/1994 | Morrissey et al. | 514/8 |
| 5,437,864 A | 8/1995 | Edgington et al. | 424/145.1 |
| 5,504,064 A | 4/1996 | Morrissey et al. | 514/8 |
| 5,504,067 A | 4/1996 | Morrissey et al. | 514/8 |
| 5,589,173 A | 12/1996 | O'Brien et al. | 424/145.1 |
| 5,589,363 A | 12/1996 | Roy et al. | 435/69.6 |
| 5,795,877 A | 8/1998 | Jackson et al. | 514/75 |
| 5,804,602 A * | 9/1998 | Slusher et al. | 514/574 |
| 5,863,536 A | 1/1999 | Jackson et al. | 424/130.1 |
| 5,880,112 A | 3/1999 | Jackson et al. | 514/121 |
| 5,902,817 A | 5/1999 | Jackson et al. | 514/347 |
| 5,968,915 A | 10/1999 | Jackson et al. | 514/89 |
| 6,004,555 A * | 12/1999 | Thorpe et al. | 424/181.1 |
| 6,036,955 A * | 3/2000 | Thorpe et al. | 424/136.1 |
| 6,150,508 A * | 11/2000 | Murphy et al. | 530/387.1 |
| 6,156,321 A | 12/2000 | Thorpe et al. | 424/198.1 |

FOREIGN PATENT DOCUMENTS

| | | |
|---|---|---|
| WO | WO-93/17715 | 9/1993 |
| WO | WO-94/05328 | 3/1994 |
| WO | WO-94/07515 | 4/1994 |
| WO | WO-94/28017 | 12/1994 |
| WO | WO-96/01653 | 1/1996 |
| WO | WO-97/48409 | * 12/1997 |

OTHER PUBLICATIONS

Akiyama, S.K., Human Cell, 1996, vol. 9: pp. 181-186.*
Abraham, Judith A., et al., "Nucleotide Sequence of a Bovine Clone Encoding the Angiogenic Protein, Basic Fibroblast Growth Factor", *Science*, 233, (1986),545-548.
Abrams, Paul G., et al., "Monoclonal Antibody Therapy of Solid Tumors", In: *Monoclonal Antibody Therapy of Human Cancer*, Foon, Kenneth A., and Alton C. Morgan, Jr., eds. Martinus Nijhoff Publishing: Boston,(1985),103-120.
Bach, Ronald, et al., "Factor VII Binding to Tissue Factor in Reconstituted Phospholipid Vesicles: Induction of Cooperativity by Phosphatidylserine", *Biochemistry*, 25, (1986),4007-4020.
Bauer, Therese, et al., "Bispecific Antibodies and Targeted Cellular Cytotoxicity: Therapeutic Hopes Confirmed", *Vox Sanguinis*, 61, (1991),156-157.
Baxter, Laurence T., et al., "Transport of Fluid and Macromolecules in Tumors III. Role in Binding and Metabolism", *Microvascular Research*, 41, (1991),5-23.
Bevilacqua, Michael P., et al., "Identification of an Inducible Endothelial-Leukocyte Adhesion Molecule", *Proceedings of the National Academy of Sciences*, 84, (1987),9238-9242.
Bhagwat, Shripad S., et al., "Synthesis and Structure of the Platelet Aggregation Factor Thromboxane A2", *Nature*, 315, (1985),511-513.
Bicknell, R., et al., "Anticancer Strategies Involving the Vasculature: Vascular Targeting and the Inhibition of Angiogenesis", *Cancer Biology*, 3, (1992),399-407.
Birembaut, P., et al., "Usefulness of Basement Membrane Markers in Tumoural Pathology", *Journal of Pathology*, 145, (1985),283-296.

(Continued)

*Primary Examiner*—Brandon J Fetterolf
(74) *Attorney, Agent, or Firm*—Hugh Wang; Thomas Fitting; Michael J. McCarthy

(57) ABSTRACT

The invention provided compositions and methods to initiate site-specific thrombosis in tumor vasculature. The present invention also provides methods for using the disclosed compositions and methods to treat tumors.

42 Claims, 13 Drawing Sheets

OTHER PUBLICATIONS

Bjorndahl, Jay M., et al., "Human T Cell Activation: Differential Response to Anti-CD28 as Compared to Anti-CD3 Monoclonal Antibodies", *European Journal of Immunology*, 19, (1989),881-887.

Borden, Ernest C., et al., "Lymphokines and Cytokines as Cancer Treatment: Immunotherapy Realized", *Cancer*, 65, (1990),800-814.

Brennan, Maureen, et al., "Preparation of Bispecific Antibodies by Chemical Recombination of Monoclonal Immunoglobulin G1 Fragments", *Science*, 229, (1985),81-83.

Brinkmann, Ulrich, et al., "B3(Fv)-PE38KDEL, a Single-Chain Immunotoxin that Causes Complete Regression of a Human Carcinoma in Mice", *Proceedings of the National Academy of Sciences*, 88, (1991),8616-8620.

Broze, Jr., George J., "The Role of Tissue Factor Pathway Inhibitor in a Revised Coagulation Cascade", *Seminars in Hematology*, 29, (1992),159-169.

Burchell, Joy, et al., "Complexity of Expression of Antigenic Determinants, Recognized by Monoclonal Antibodies HMFG-1 and HMFG-2, in Normal and Malignant Human Mammary Epithelial Cells", *Journal of Immunology*, 131, (1983),508-513.

Burrows, Francis J., et al., "A Murine Model for Antibody-Directed Targeting of Vascular Endothelial Cells in Solid Tumors", *Cancer Research*, 52, (1992),5954-5962.

Burrows, Francis J., et al., "Eradication of Large Solid Tumors in Mice with an Immuotoxin Directed Against Tumor Vasculature", *Proceedings of the National Acacemy of Sciences*, 90, (1993),8996-9000.

Burrows, Francis J., et al., "Influence of Tumor-Derived Interleukin 1 on Melanoma-Endothelial Cell Interactions in Vitro", *Cancer Research*, 51, (1991),4768-4775.

Burtin, P., et al., "Alterations of the Basement Membrane and Connective Tissue Antigens in Human Metastatic Lymph Nodes", *International Journal of Cancer*, 31, (1983),719-726.

Byers, V. S., et al., "Therapeutic Strategies with Monoclonal Antibodies and Immunoconjugates", *Immunology*, 65, (1988),329-335.

Campbell, "Selection of Animals and Cell Lines 3.4", *In: Monoclonal Antibody Technology, Laboratory Techniques in Biochemistry and Molecular Biology*, 13, Burdon, R.H. and P.H. van Knippenberg, eds. Elsevier: Amsterdam,(1984),75-83.

Carmeliet, Peter, et al., "Role of Tissue Factor in Embryonic Blood Vessel Development", *Nature*, 383, (1996),73-75.

Carter, Ruth E., et al., "Prostate-Specific Membrane Antigen is a Hydrolase with Substrate and Pharmacologic Characteristics of a Neuropeptidase", *Proceedings of the National Academy of Sciences*, 93, (1996),749-753.

Chang, Sam S., et al., "Five Different Anti-Prostate-Specific Membrane Antigen (PSMA) Antibodies Confirm PSMA Expression in Tumor-Associated Neovasculature", *Cancer Research*, 59, (1999),3192-3198.

Chen, Tai-Ying, et al., "Induction of Macrophage-Mediated Tumor Cytotoxicity by a Hamster Monoclonal Antibody with Specificity for Lipopolysaccharide Receptor", *Journal of Immunology*, 145, (1990),8-12.

Further Differences in Lymphokine Synthesis Between Th1 and Th2 Clones Revealed by RNA Hybridization, Functionally Monospecific Bioassays, and Monoclonal Antibodies, *Journal of Experimental Medicine*, 166, (1987),1229-1244.

Clark, Gary M., et al., "Follow-up Study of HER-2/neu Amplification in Primary Breast Cancer", *Cancer Research*, 51, (1991),944-948.

Clark, Adrian, et al., "Synthesis of Epidermal Growth Factor (EGF) Receptor In Vitro Using SP6 RNA Polymerase-Transcribed Template mRNA", *Biochimica et Biophysica Acta*, 867, (1986),244-251.

Clark, Mike, et al., "The Potential of Hybrid Antibodies Secreted by Hybrid-Hybridomas in Tumour Therapy", *International Journal of Cancer: Supp. 2*, (1988),15-17.

Colcher, David, et al., "Complementation of Intracavitary and Intravenous Administration of a Monoclonal Antibody (B72.3) in Patients with Carcinoma", *Cancer Research*, 47, (1987),4218-4224.

Colcher, David, et al., "Quantitive Analyses of Selective Radiolabeled Monoclonal Antibody Localization in Metastatic Lesions of Colorectal Cancer Patients", *Cancer Research*, 47, (1987),1185-1189.

Collins, Tucker, et al., "Immune Interferon Activates Multiple Class II Major Histocompatibility Complex Genes and the Associated Invariant Chain Gene in Human Endothelial Cells and Dermal Fibroblasts", *Proceedings of the National Academy of Sciences*, 81, (1984),4917-4921.

Cotran, Ramzi S., et al., "Induction and Detection of a Human Endothelial Activation Antigen In Vivo", *Journal of Experimental Medicine*, 164, (1986),661-666.

Daar, A. S., et al., "The Detailed Distribution of MHC Class II Antigens in Normal Human Organs", *Transplantation*, 38, (1984),293-298.

Davie, Earl W., et al., "The Coagulation Cascade: Initiation, Maintenance, and Regulation", *Biochemistry*, 30, (1991),10363-10370.

Davies, David R., et al., "Cytokines and Their Receptor Complexes", *FASEB Journal*, 9, (1995),50-56.

Davis, Minh-Tam B., et al., "A Simple Modified Carbodiimide Method for Conjugation of Small-Molecular-Weight Compounds to Immunoglobulin G with Minimal Protein Crosslinking", *Analytical Biochemistry*, 116. (1981),402-407.

De Lau, Wim, et al., "Heterodimeric Complex Formation with CD8 and TCR by Bispecific Antibody Sustains Paracrine IL-2-Dependent Growth of CD3+ CD8+ T Cells", *Journal of Immunology*, 149, (1992),1840-1846.

Defranco, Anthony L., et al., "Immunosuppressants at Work", *Nature*, 352, (1991),754-755.

Denekamp, J., et al., "Endothelial-Cell Proliferation in Experimental Tumours", *British Journal of Cancer*, (1982),711-720.

Dewerchin, M., et al., "Effect of Chemical Conjugation of Recombinant Single-Chain Urokinase-Type Plasminogen Activator With Monoclonal Antiplatelet Antibodies on Platelet Aggregation and on Plasma Clot Lysis In Vitro and In Vivo", *Blood*, 78, (1991),1005-1018.

Di Scipio, Richard G., et al., "Activation of Human Factor X (Stuart Factor) by a Protease from Russell's Viper Venom", *Biochemistry*, 16, (1977),5253-5260.

Dillman, Robert O., et al., "Comparisons of Drug and Toxin Immunoconjugates", *Antibody, Immunoconjugates, and Radiopharmaceuticals*, 1, (1988),65-77.

Drake, Thomas A., et al., "Functional Tissue Factor is Entirely Cell Surface Expressed on Lipopolysaccharide-Stimulated Human Blood Monocytes and a Constitutively Tissue Factor-Producing Neoplastic Cell LIne", *Journal of Cell Biology*, 109, (1989),389-395.

Dustin, Michael L., et al., "Induction by IL 1 and Interferon-y: Tissue Distribution, Biochemistry, and Function of a Natural Adherence Molecule (ICAM-1)1", *Journal of Immunology*, 137, (1986),245-254.

Dvorak, Harold F., et al., "Distribution of Vascular Permeability Factor (Vascular Endothelial Growth Factor) in Tumors: Concentration in Tumor Blood Vessels" *Journal of Experimental Medicine*, 174, (1991),1275-1278.

Edgington, Thomas S., et al., "The Structural Basis of Function of the TF-VIIa Complex in the Cellular Initiation of Coagulation", *Thrombosis and Haemostasis*, 78, (1997),401-405.

Edgington, Thomas S., et al., "The Structural Biology of Expression and Function of Tissue Factor", *Thrombosis and Haemostasis*, 66, (1991),67-79.

Embleton, M. J., et al., "Recombinant Ricin Toxin A Chain Cytotoxicity Against Carcinoembryonic Antigen Expressing Tumour Cells Mediated by a Bispecific Monoclonal Antibody and its Potentiation by Ricin Toxin B Chain", *British Journal of Cancer*, 63, (1991),670-674.

Epenetos, Agamemnon A., et al., "Limitations of Radiolabeled Monoclonal Antibodies for Localization of Human Neoplasms", *Cancer Research*, 46, (1986),3183-3191.

Erlanson, Daniel A., et al., "The Leucine Zipper Domain Controls the Orientation of AP-1 in the NFAT-AP-1-DNA Complex", *Chemistry and Biology*, 3, (1996),981-991.

Fair, Daryl S., et al., "Cooperative Interaction between Factor VII and Cell Surface-expressed Tissue Factor", *Journal of Biological Chemistry*, 262, (1987),11692-11698.

Fair, Daryl S., "Quantitation of Factor VII in the Plasma of Normal and Warfarin-Treated Individuals by Radioimmunoassay", *Blood*, 62, (1983),784-791.

Ferrara, Napoleone, et al., "The Vascular Endothelial Growth Factor Family of Polypeptides", *Journal of Cellular Biochemistry*, 47, (1991),211-218.

Flavell, D.J., et al., "Characteristics and Performance of a Bispecific F (ab'y)2 Antibody for Delivering Saporin to CD7+ Human Acute T-cell Leukaemia Cell Line", *British Journal of Cancer*, 64, (1991),274-280.

Flavell, D.J., et al., "Effectiveness of Combinations of Bispecific Antibodies for Delivering Saporin to Human Acute T-cell Lymphoblastic Leukaemia Cell Line via CD7 and CD38 as Cellular Target Molecules", *British Journal of Cancer*, 65, (1992),545-551.

Folkman, Judah, "Angiogenesis and Its Inhibitors", *In: Important Advances in Oncology*, Winters, Richard, ed. J. B. Lippincott Company: Philadelphia,(1985),42-62.

Folkman, Judah, "Tumor Angiogenesis", *In: Advances in Cancer Research*, 43, Klein, George, ed. Academic Press, Inc.: Orlando,(1985),175-203.

Fox, Bernard A., et al., "In Vitro and In Vivo Antitumor Properties of a T-Cell Clone Generated from Murine Tumor-Infiltrating Lymphocytes", *Journal of Biological Response Modifiers*, 9, (1990), 499-511.

Freelinger III, Andrew L., et al., "Monoclonal Antibodies to Ligand-occupied Conformers of Integrin aiibB3 (Glycoprotein IIb-IIIa) Alter Receptor Affinity, Specificity, and Function", *Journal of Biological Chemistry*, 266, (1991),17106-17111.

Frelinger III, Andrew L., et al., "Selective Inhibition of Integrin Function by Antibodies Specific for Ligand-occupied Receptor Conformers", *Journal of Biological Chemistry*, 265, (1990), 6346-6352.

French, Ruth R., et al., "Cooperative Mixtures of Bispecific F(ab')2 Antibodies for Delivering Saporin to Lymphoma in Vitro and in Vivo", *Cancer Research*, 51, (1991),2353-2361.

Galfre, G., "Preparation of Monoclonal Antibodies: Strategies and Procedures", *In: Methods in Enzymology: Immunochemical Techniques, Part B*, 73, Langone, John J., ed. Academic Press: New York,(1981),3-46.

Galivan, J., et al., "The Role of Folylpolyglutamate Synthetase and y-Glutamyl Hydrolase in Altering Cellular Foly- and Antifolylpolyglutamates", *In: Advances in Enzyme Regulation*, 26, Weber George, ed. Pergamon Press: New York,(1987),147-155.

Gefter, Malcolm L., et al., "A Simple Method for Polyethylene Glycol-Promoted Hybridization of Mouse Myeloma Cells", *Somatic Cell Genetics*, 3, (1977),231-236.

Geppert, Thomas D., et al., "Accessory Cell Signals Involved in T-Cell Activation", *Immunological Reviews*, 117, (1990),5-66.

Ghose, Tarun I., et al., "Preparation of Antibody-Linked Cytotoxic Agents", *In: Methods in Enzymology: Immunochemical Techniques, Part F Conventional Antibodies, Fc Receptors, and Cytotoxicity*, 93, Langone, John J., ed. Academic Press: New York,(1983),280-333.

Ghose, T., et al., "The Design of Cytotoic-Agent-Antibody Conjugates", *In: CRC Critical Reviews in Therapeutic Drug Carrier Systems*, 3, (1987),263-359.

Giles, Alan R., et al., "A Combination of Factor Xa and Phosphatidylcholine-Phosphatidylserine Vesicles Bypasses Factor VIII in Vivo", *Journal of Haematology*, 69, (1988),491-497.

Glennie, Martin J., et al., "Preparation and Performance of Bispecific F(ab'y)2 Antibody Containing Thioether-Linked Fab'y Fragments", *Journal of Immunology*, 139, (1987),2367-2375.

Goding, James W., "Production of Monclonal Antibodies", *In: Monoclonal Antibodies: Principles and Practice*, 2nd ed., Academic Press Limited: London,(1986),59-74.

Gougos, Anne, et al., "Identification of a Human Endothelial Cell Antigen with Monclonal Antibody 44G4 Produced Against a Pre-B Leukemic Cell Line", *Journal of Immunology*, 141, (1988),1925-1933.

Grauer, Lana S., et al., "Identification, Purification, and Subcellular Localization of Prostate-Specific Membrane Antigen PSM' Protein in the LNCaP Prostatic Carcinoma Cell Line", *Cancer Research*, 58, (1998),4787-4789.

Griffith, Eric C., et al., "Methionine Aminopeptidase (Type 2) is the Common Target for Angiogenesis Inhibitors AGM-1470 and Ovalicin", *Chemistry and Biology*1, 4, (1997),461-471.

Groenewegen, G., et al., "Lymphokine Dependence of In Vivo Expression of MHC Class II Antigens by Endothelium", *Nature*, 316, (1985),361-363.

Hagen, Fredericks S., et al., "Characterization of a cDNA Coding for Human Factor VII", *Proceedings of the National Academy of Sciences*, 83, (1986),2412-2416.

Halling, Kevin C., et al., "Genomic Cloning and Characterization of a Ricin Gene from Ricinus Communis", *Nucleic Acids Research*, 13, (1985),8019-8033.

Hammerling, G. J., "Tissue Distribution of Ia Antigens and Their Expression on Lymphocyte Subpopulations", *In: Transplantation Reviews: Biochemistry and Biology of Ia Antigens*, 30, (1976),64-82.

Hattey, E., et al., "Monoclonal Antibodies Against Plasminogen and Alpha-2-Antiplasmin: Binding to Native and Modified Antigens", *Thrombosis Research*, 45, (1987),485-495.

Hayward, Catherine, et al., "p-155, a Multimeric Platelet Protein that is Expressed on Activated Platelets", *Journal of Biological Chemistry*, 266, (1991),7114-7120.

Hess, Allan D., et al., "The Effect of the CD28 Activation Pathway on the Immunosuppressive Action of Cyclosporine", *Transplantation*, 51, (1991),1232-1240.

Heston, W., "Bedeutung des prostataspezifischen Membranantigens (PSMA)", *Urologe*, 35, (1996),400-407.

Heston, Warren, "Characterization and Glutamyl Preferring Carboxypeptidase Function of Prostate Specific Membrane Antigen: A Novel Folate Hydrolase", *Urology*, 49, (1997),104-112.

Heynen, Harry, et al., "Absence of Ligands Bound to Glycoprotein IIB-IIIA on the Exposed Surface of a Thrombus May Limit Thrombus Growth in Flowing Blood", *Journal of Clinical Investigation*, 94, (1994),1098-1112.

Horoszewicz, Julius S., et al., "Monoclonal Antibodies to a New Antigenic Marker in Epithelial Prostatic Cells and Serum of Prostatic Cancer Patients", *Anticancer Research*, 7, (1987),927-936.

Huang, Xianming, et al., "Tumor Infarction in Mice by Antibody-Directed Targeting of Tissue Factor to Tumor Vasculature", *Science*, 275, (1997),547-550.

Ingber, Donald, et al., "Synthetic Analogues of Fumagillin that Inhibit Angiogenesis and Suppress Tumour Growth", *Nature*, 348, (1990),555-557.

Israeli, Ron S., et al., "Molecular Cloning of a Complementary DNA Encoding a Prostate-Specific Membrane Antigen", *Cancer Research*, 53, (1993),227-230.

Jackson, Paul F., et al., "Design, Synthesis, and Biological Activity of a Potent Inhibitor of the Neuropeptidase N-Acetylated a-Linked Acidic Dipeptidase", *Journal of Medicinal Chemistry*, 39, (1996),619-622.

Jain, Rakesh K., "Vascular and Interstitial Barriers to Delivery of Therapeutic Agents in Tumors", *Cancer and Metastasis Reviews*, 9, (1990),253-266.

June, Carl H., et al., "Role of the CD28 Receptor in T-cell Activation", *Immunology Today*, 11, (1990),211-216.

June, Carl H., et al., "T-Cell Proliferation Involving the CD28 Pathway is Associated with Cyclosporine-Resistant Interleukin 2 Gene Expression", *Molecular and Cellular Biology*, 7, (1987),4472-4481.

Juweid, Malik, et al., "Micropharmacology of Monoclonal Antibodies in Solid Tumors: Direct Experimental Evidence for a Binding Site Barrier", *Cancer Research*, 52, (1992),5144-5153.

Kandel, J., "Neovasculatization is Associated with a Switch to the Export of bFGF in the Multistep Development of Fibrosarcoma", *Cell*, 66, (Sep. 20, 1991),pp. 1095-1104.

Kim, K. J., et al., "Inhibition of Vascular Endothelial Growth Factor-Induced Angiogenesis Suppresses Tumour Growth In Vivo", *Nature*, 362, (1993),841-844.

Kimura, Shoji, et al., "Studies of the Mouse Ly-6 Alloantigen System I. Serological Characterization of Mouse Ly-6 Alloantigen by Monoclonal Antibodies", *Immunogenetics*, 11, (1980),373-381.

Kisiel, Walter, et al., "Molecular Properties of the Factor V-activating Enzyme from Russell's Viper Venom", *Journal of Biological Chemistry*, 254, (1979),12230-12234.

Klagsbrun, M., et al., "Angiogenesis", *In: Peptide Growth Factors and Their Receptors II*, Ch. 37, Ed. Sporn, Michael B. and Anita B. Roberts, Springer-Verlag: Berlin,(1990),549-586.

Kohler, G., "Continuous cultures of fused cells secreting antibody of predefined specifity", *Nature*, 256, (Aug. 7, 1975),495-497.

Kohler, G., et al., "Derivation of Specific Antibody-Producing Tissue Culture and Tumor Lines by Cell Fusion", *European Journal of Immunology*, 6, (1976),511-519.

Krishnaswamy, Sriram, et al., "Role of the Membrane Surface in the Activation of Human Coagulation Factor X", *Journal of Biological Chemistry*, 267, (1992),26110-26120.

Kyte, Jack, et al., "A Simple Method for Displaying the Hydropathic Charcter of a Protein", *Journal of Molecular Biology*, 157, (1982),105-132.

Lamb, F. I., et al., "Nucleotide Sequence of Cloned cDNA Coding for Preproricin", *European Journal of Biochemistry*, 148, (1985),265-270.

Lee, Ethan, et al., "Expression of G-Protein a Subunits in *Escherichia coli*", In: *Methods in Enzymology, Heterotrimeric G Proteins*, 237, Iyengar, Ravi, ed. Academic Press: New York,(1994),146-164.

Liu, He, et al., "Constitutive and Antibody-Induced Internalization of Prostate-Specific Membrane Antigen", *Cancer Research*, 58, (1998),4055-4060.

Liu, He, et al., "Monoclonal Antibodies to the Extracellular Domain of Prostate-Specific Membrane Antigen Also React with Tumor Vascular Endothelium", *Cancer Research*, 57, (1997),3629-3634.

Liu, Cheng, et al., "Prostate-Specific Membrane Antigen Directed Selective Thrombotic Infarction of Tumors", *Cancer Research*, 62, (2002),5470-5475.

Liu, Shenping, et al., "Structure of Human Methionine Aminopeptidase-2 Complexed with Fumagillin", *Science*, 282, (1998),1324-1327.

Lord, J. M., et al., "Chimeric Proteins Containing Ricin A Chain", *In: Genetically Engineered Toxins*, Frankel, Arthur E., ed. Marcel Dekker, Inc.: New York,(1992),183.

Lowder, James N., et al., "Studies on B Lymphoid Tumors Treated with Monoclonal Anti-Idiotype Antibodies: Correlation with Clinical Responses", *Blood*, 69, (1987),199-210.

Lowe, Jennifer, et al., "Studies on the Reappearance of MHC Class II Antigens on Cells of a Variant Human Lymphoblastoid Line", *Immunology Letters*, 12, (1986),263-269.

Maeda, Kazuo, et al., "Production and Characterization of Tumor Infiltrating Lymphocyte Clones Derived from B16-F10 Murine Melanoma", *Journal of Investigative Dermatology*, 97, (1991),183-189.

Manabe, Yuichi, et al., "Production of a Monoclonal Antibody-Methotrexate Conjugate Utilizing Dextran T-40 and Its Biologic Activity", *Journal of Laboratory and Clinical Medicine*, 104, (1984),445-454.

Martin, David M., et al., "Tissue Factor: Molecular Recognition and Cofactor Function", *FASEB Journal*, 9, (1995),852-859.

Massoglia, S. L., et al., "Characterization of Murine Monoclonal Antibodies Directed Against Basic Fibroblast Growth Factor", *Journal of Cellular Physiology*, 132, (1987),531-537.

Mazzocchi, Arabella, et al., "T Lymphocytes can Mediate Lysis of Autologous Melanoma Cells by Multiple Mechanisms: Evidence with a Single T Cell Clone", *Cancer Immunology Immunotherapy*, 32, (1990),13-21.

McGuire, John J., "Exploitation of Folate and Antifolate Polyglutamylation to Achieve Selective Anticancer Chemotherapy", *Investigational New Drugs*, 14, (1996),317-323.

Mignatti, Paolo, et al., "Expression fo the Urokinase Receptor in Vascular Endothelial Cells is Stimulated by Basic Fibroblast Growth Factor", *Journal of Cell Biology*, 113, (1991),1193-1201.

Miotti, Silvia, et al., "Biochemical Analysis of Human Ovarian Cancer-associated Antigens Defined by Murine Monoclonal Antibodies", *Cancer Research*, 45, (1985),826-832.

Moroi, Masaaki, et al., "Isolation and Characterization of a2-Plasmin Inhibitor from Human Plasma", *Journal of Biological Chemistry*, 251, (1976),5956-5965.

Morrison, Sherie L., et al., "Production of Novel Immunoglobulin Molecules by Gene Transfection", *Mount Sinai Journal of Medicine*, 53, (1986), 175-180.

Morrissey, James H., et al., "Molecular Cloning of the cDNA for Tissue Factor, the Cellular Receptor for the Initiation of the Coagulation Protease Cascade", *Cell*, 50, (1987),129-135.

Morrissey, James H., et al., "Monoclonal Antibody Analysis of Purified and Cell-Associated Tissue Factor", *Thrombosis Research*, 52, (1988),247-261.

Morrissey, James H., et al., "Ouantitation of Activated Factor VII Levels in Plasma Using a Tissue Factor Mutant Selectively Deficient in Promoting Factor VII Activation", *Blood*, 81, (1993),734-744.

Mueller, Barbara M., et al., "Expression of Tissue Factor by Melanoma Cells Promotes Efficient Hematogenous Metastasis", *Proceedings of the National Academy of Sciences*, 89, (1992),11832-11836.

Murray, J. C., et al. "Tumour-Derived Factors Which Induce Endothelial Tissue Factor and Enhance the Procoagulant Response to TNF", *International Journal of Radiation Biology*, 60, (1991),273-277.

Nakamura, Toshikazu, "Structure and Function of Hepatocyte Growth Factor", *Progress in Growth Factor Research*, 3, (1991),67-85.

Nawroth, Peter, et al., "Modulation of Endothelial Cell Hemostatic Properties by Tumor Necrosis Factor", *Journal of Experimental Medicine*, 163, (Mar. 1986),740-745.

Nawroth, Peter, et al., "Tumor Necrosis Factor/Cachectin-Induced Intravascular Fibrin Formation in Meth a Fibrosarcomas", *Journal of Experimental Medicine*, 168, (Aug. 1988),637-647.

Nelson, Heidi, "Targeted Cellular Immunotherapy with Bifunctional Antibodies", *Cancer Cells*, 3, (May 1991),163-172.

Nemerson, Yale, "Tissue Factor and Hemostasis", *Blood*71, (Jan. 1988),1-8.

Nitta, Taizo, et al., "Preliminary Trial of Specific Targeting Therapy Against Malignant Glioma", *The Lancet*, 335, (1990),368-371.

O'Brien, Donogh P., et al., "Factor VIII-Bypassing Activity of Bovine Tissue Factor Using the Canine Hemophilic Model", *Journal of Clinical Investigation*, 82, (1988),206-211.

O'Connell, Kathryn A., et al., "A Mouse Lymphoid Endothelial Cell Line Immortalized by Simian Virus 40 Binds Lymphocytes and Retains Functional Characteristics of Normal Endothelial Cells", *Journal of Immunology*, 144, (1990),521-525.

O'Connor, Brigid M., et al., "Secretion of y-Glutamyl Hydrolase in Vitro", *Cancer Research*, 51, (1991),3874-3881.

O'Hare, Mary, et al., "Expression of Ricin A Chain in *Escherichia coli*", *FEBS Letters*, 216, (1987),73-78.

Ogata, Masato, et al., "Processing of *Pseudomonas* Exotoxin by a Cellular Protease Results in the Generation of a 37,000-Da Toxin Fragment That is translocated to the Cytosol", *Journal of Biological Chemistry*, 265, (1990),20678-20685.

Ogawa, Satoshi, et al., "The Effect of Hypoxia on Capillary Endothelial Cell Function: Modulation of Barrier and Coagulant Function", *British Journal of Haematology*, 75, (1990),517-524.

Ohuchida, Shuichi, et al., "Synthesis of Thromboxane A2 Analogues: DL-9,11:11,12-Dideoxa-9,11:11,12-diepithiothromboxane A2", *Journal of the American Chemical Society*, 103, (1981),4597-4599.

Osborn, Laurelee, et al., "Direct Expression Cloning of Vascular Cell Adhesion Molecule 1, a Cytokine-Induced Endothelial Protein That Binds to Lymphocytes", *Cell*, 59, (1989),1203-1211.

Osterud, B., et al., "Thromboplastin Content in the Vessell Walls of Different Arteries and Organs of Rabbits", *Thrombosis Research*, 42, (1986),323-329.

Paborsky, Lisa R., et al., "Lipid Association, but Not the Transmembrane Domain, Is Required for Tissue Factor Activity", *Journal f Biological Chemistry*, 266, (1991),21911-21916.

Palleroni, Alicia V., et al., "Tumoricidal Alveolar Macrophage and Tumor Infiltrating Macrophage Cell Lines", *International Journal of Cancer*, 49, (1991),296-302.

Pasqualini, Renata, et al., "av Integrins as Receptors for Tumor Targeting by Circulating Ligands", *Nature Biotechnology*, 15, (1997),542-546.

Payne, Gillian, "Progress in Immunoconjugate Cancer Therapeutics", *Cancer Cell*, 3, (Mar. 2003),207-212.

Perez, Pilar, et al., "Specific Lysis of Human Tumor Cells by T Cells Coated with Anti-T3 Cross-linked to Anti-Tumor Antibody", *Journal of Immunology*, 137, (1986),2069-2072.

Perez, Pilar, et al., "Specific Targeting of Cytotoxic T Cells by Anti-T3 Linked to Anti-Target Cell Antibody ", *Nature*, 316, (1985),354-356.

Perez, Pilar, et al., "Specific Targeting of Human Peripheral Blood T Cells by Heteroaggregates Containing Anti-T3 Crosslinked to Anti-Target Cell Antibodies", *Journal of Experimental Medicine*, 163, (1986),166-178.

Pietersz, Geoffrey A., et al., "Preclinical and Clinical Studies with a Variety of Immunoconjugates", *Antibody, Immunoconjugates, and Radiopharmaceuticals*, 1, (1988),79-103.

Pimm, M. V., et al., "Capture of Recombinant Ricin A Chain by a Bispecific Anti-RTA: Anti-CEA Monoclonal Antibody Pre-Targeted to a Human Gastric Carcinoma Xenograft in Nude Mice", *Journal of Cancer Research and Clinical Oncology*, 118, (1992),367-370.

Pober, Jordan S., et al., "Ia Expression by Vascular Endothelium is Inducible by Activated T Cells and by Human y Interferon", *Journal of Experimental Medicine*, 157, (1983),1339-1353.

Pukrittayakamee, Sasithon, et al., "Purification and Inactivation of the Factor X Activator of Russell's Viper Venom with Monoclonal Antibodies", *Mol. Biol. Medicine*, 1, (1983),123-135.

Rehemtulla, Alnawaz, et al., "High Level Expression of Recombinant Human Tissue Factor in Chinese Hamster Ovary Cells as a Human Thromboplastin", *Thrombosis and Haemostasis*, 65, (1991),521-527.

Reisfeld, R. A., et al., "Molecular and Immunological Characterization of Human Melanoma-Associated Antigens", *In: Melanoma Antigens and Antibodies*, (1982),317-337.

Rettig, Wolfgang J., et al., "Identification of Endosialin, a Cell Surface Glycoprotein of Vascular Endothelial Cells in Human Cancer", *Proceedings of the National Academy of Sciences*, 89, (1992),10832-10836.

Rhee, Myung S., et al., "Acquistion of Resistance to Antifolates Caused by Enhanced y-Glutamyl Hydrolase Activity", *Cancer Research*, 53, (1993),2227-2230.

Ruco, Luigi P., et al., "Cytokine Production (IL-1a, IL-1B, and TNFa) and Endothelial Cell Activation (ELAM-1 and HLA-DR) in Reactive Lymphadenitis, Hodgkin's Disease, and in Non-Hodgkin's Lymphomas", *American Journal of Pathology*, 137, (1990),1163-1171.

Ruf, Wolfram, et al., "An Anti-Tissue Factor Monoclonal Antibody which Inhibits TF-VIIa Complex is a Potent Anticoagulant in Plasma", *Thrombosis and Haemostasis*, 66, (1991),529-533.

Ruf, Wolfram, et al., "Cofactor Residues Lysine 165 and 166 Are Critical for Protein Substrate Recognition by the Tissue Factor-Factor VIIa Protease Complex", *Journal of Biological Chemistry*, 267, (1992),6375-6381.

Ruf, Wolfram, et al., "Phospholipid-independent and -dependent Interactions Required for Tissue Factor Receptor and Cofactor Function", *Journal of Biological Chemistry*, 266, (1991),2158-2166.

Ruf, Wolfram, et al., "Structural Biology of Tissue Factor, the Initiator of Thrombogenesis in Vivo", *FASEB Journal*, 8, (1994),385-390.

Ruf, Wolfram, et al., "Tissue Factor Residues 157-167 Are Required for Efficient Proteolytic Activation of Factor X and Factor VII", *Journal of Biological Chemistry*, 267,22206-22210.

Ruf, Wolfram, et al., "Two Sites in the Tissue Factor Extracellular Domain Mediate the Recognition of the Ligand Factor VIIa", *Proceedings of the National Academy of Sciences*, 88, (1991),8430-8434.

Sakai, Toshiyuki, et al., "Formation of Tissue Factor Activity Following Incubation of Recombinant Human Tissue Factor Apoprotein with Plasma Lipoproteins", *Thrombosis Research*, 60, (1990),213-222.

Sands, Howard, "Radioimmunoconjugates: An Overview of Problems and Promises", *Antibody, Immunoconjugates, and Radiopharmaceuticals*, 1, (1988),213-226.

Schutt, C., et al., "Human Monocyte Activation Induced by an Anti-CD14 Monoclonal Antibody", *Immunology Letters*, 19, (1988),321-328.

Segal, David M., et al., "Targeted Cytokine Production", *International Journal of Cancer*, Supp. 7, (1992),36-38.

Serval, V., et al., "Competitive Inhibition of N-Acetylated-a-Linked Acidic Dipeptidase Activity by N-Acetyl-L-Aspartyl-B-Linked L-Glutamate", *Journal of Neurochemistry*, 55, (1990),39-46.

Serval, V., et al., "In Vitro and in Vivo Inhibition of N-Acetyl-L-Aspartyl-L-Glutamate Catabolism by N-Acylated L-Glutamate Analogs", *Journal of Pharmacology and Experimental Therapeutics*, 260, (1992),1093-1100.

Shankar, Ravi, et al., "Thrombin Receptor-Activating Peptides Differentially Stimulate Platelet-Derived Growth Factor Production, Moncytic Cell Adhesion, and E-selectin Expression in Human Umbilical Vein Endothelial Cells", *Journal of Biological Chemistry*, 269, (1994),13936-13941.

Shen, Rong-Fong, et al., "Monoclonal Antibodies to Thromboxane Synthase from Porcine Lung", *Journal of Biological Chemistry*, 261, (1986),11585-11591.

Shepard, H. M., et al., "Monoclonal Antibody Therapy of Human Cancer: Taking the HER2 Protooncogene to the Clinic", *Journal of Clinical Immunology*, 11, (1991),117-127.

Shockley, Ty R., et al., "Penetration of Tumor Tissue by Antibodies and Other Immunoproteins", *Annals of the New York Academy of Sciences*, 618, (1991),367-383.

Silver, David A., et al., "Prostate-specific Membrane Antigen Expression in Normal and Malignant Human Tissues", *Clinical Cancer Research*, 3, (1997),81-85.

Smith, A., et al., "Immunolocalisation and Imaging of Small Cell Cancer Xenografts by the IgG2a Monoclonal Antibody SWA11", *British Journal of Cancer*, 59, (1989),174-178.

Spiegelberg, Hans L., et al., "The Catabolism of Homologous and Heterologous 7S Gamma Globulin Fragments", *Journal of Experimental Medicine*, 121, (1965),323-338.

Staerz, Uwe D., et al., "Hybrid Antibodies Can Target Sites For Attack by T Cells", *Nature*, 314, (1985),628-631.

Stevenson, Freda K., et al., "Anti-Idiotypic Therapy of Leukemias and Lymphomas", *Chemical Immunology*, 48, (1990),126-166.

Stone, Martin J., et al., "Recombinant Soluble Human Tissue Factor Secreted by *Saccharomyces cerevisiae* and Refolded from *Escherichia coli* Inclusion Bodies: Glycosylation of Mutants, Activity and Physical Characterization", *Biochemical Journal*, 310, (1995),605-614.

Street, Nancy E., et al., "In Vivo Administration of Fab Fragments of Anti-L3T4 (GK1.5) Antibody Inhibits the T Helper Celll Function of Murine Lymph Node Cells", *Cellular Immunology*, 120, (1989),75-81.

Su, Sai L., et al., "Alternativelly Spliced Variants of Prostate-Specific Membrane Antigen RNA: Ratio of Expression as a Potential Measurement of Progression", *Cancer Research*, 55, (1995),1441-1443.

Sugama, Kazushige, et al., "Functional Expression of H1-Histaminergic Receptors in *Xenopus laevis* Oocytes Injected with Bovine Adrenal Medullary mRNA", *Japanese Journal of Pharmacology*, 55, (1991),287-290.

Sugama, Yasuo, et al., "Thrombin-induced Expression of Endothelial P-Selection and Intercellular Adhesion Molecule-1: A Mechanism for Stabilizing Neutrophil Adhesion", *Journal of Cell Biology*, 119, (1992),935-944.

Ten Cate, Hugo, et al., "The Activation of Factor X and Prothrombin by Recombinant Factor VIIa In Vivo is Mediated by Tissue Factor", *Journal of Clinical Investigation*, 92, (1993),1207-1212.

Thieme, Hagen, et al., "Comparative Analysis of Vascular Endothelial Growth Factor Receptors on Retinal and Aortic Vascular Endothelial Cells", *Diabetes*, 44, (1995),98-103.

Thor, Ann, et al., "Distribution of Oncofetal Antigen Tumor-associated Glycoprotein-72 Defined by Monoclonal Antibody B72.3", *Cancer Research*, 46, (1986),3118-3124.

Tiffany, Carol W., et al., "Characterization of the Enzymatic Activity of PSM: Comparison with Brain NAALADase", *The Prostate*, 39, (1999),28-35.

Ting, Chou-Chik, et al., "Augmentation By Anti-T3 Antibody of the Lymphokine-Activated Killer Cell-Mediated Cytotoxicity", *Journal of Immunology*, 141, (1988),741-748.

Titus, Julie A., et al., "Human T Cells Targeted with Anti-T3 Crosslinked to Antitumor Antibody Prevent Tumor Growth in Nude Mice", *Journal of Immunology*, 138, (1987),4018-4022.

Tomiyama, Yoshiaki, et al., "The Arg-Gly-Asp (RGD) Recognition Site of Platelet Glycoprotein IIb-IIIa on Nonactivated Platelets Is Accessible to High-Affinity Macromolecules", *Blood*, 79, (1992),2303-2312.

Tutt, Alison, et al., "Bispecific F(ab'y)3 Antibody Derivatives for Redirecting Unprimed Cytotoxic T Cells", *European Journal of Immunology*, 21, (1991),1351-1358.

Ugarova, Tatiana P., et al., "Conformational Changes in Fibrinogen Elicited by Its Interaction with Platelet Membrane Glycoprotein GPIIb-IIIa", *Journal of Biological Chemistry*, 268, (1993),21080-21087.

Vaickus, Louis, et al., "Overview of Monoclonal Antibodies in the Diagnosis and Therapy of Cancer", *Cancer Investigation*, 9, (1991),195-209.

Van Dijk, J., et al., "Induction of Tumor-Cell Lysis by Bi-Specific Monoclonal Antibodies Recognizing Renal-Cell Carcinoma And CD3 Antigen", *International Journal of Cancer*, 43, (1989), 344-349

Venkateswaran, Subrananiam, et al., "Production of Anti-Fibroblast Growth Factor Receptor Monoclonal Antibodies by In Vitro Immunization", *Hybridoma*, 11, (1992),729-739.

Vitetta, Ellen S., et al., "Phase I Immunotoxin Trial in Patients with B-Cell Lymphoma", *Cancer Research*, 51, (1991),4052-4058.

Wang, J. M., et al., "A Monoclonal Antibody Detects Heterogeneity in Vascular Endothelium of Tumours and Normal Tissues", *International Journal of Cancer*, 54, (1993),363-370.

Wang, Lee-Ho, et al., "Isolation of Partial Complementary DNA Encoding Human Thromboxane Synthase", *Biochemical and Biophysical Research Communications*, 177, (1991),286-291.

Wang, Ying, et al., "Two Novel HPLC Methods Which Rapidly Detect the Substrates and Cleavage Products of y-Glutamyl Hydrolase", *In: Chemistry and Biology of Pteridines and Folates*, Ed. Ayling, June E, et al., Plenum Press: New York,(1993),655-658.

Warr, Thomas A., et al., "Disseminated Intravascular Coagulation in Rabbits Induced by Administration of Endotoxin or Tissue Factor: Effect of Anti-Tissue Factor Antibodies and Measurement of Plasma Pathway Inhibitor Activity", *Blood*, 75, (1990),1481-1489.

Watanabe, Yoshihiko, et al., "Exogenous Expression of Mouse Interferon y cDNA in Mouse Neuroblastoma C1300 Cells Results in Reduced Tumorigenicity by Augmented Anti-Tumor Immunity", *Proceedings of the National Academy of Sciences*, 86, (1989),9456-9460.

Wawrzynczak, Edward J., et al., "Methods for Preparing Immunotoxins: Effect of the Linkage on Activity and Stability", *In: Immunoconjugates: Antibody Conjugates in Radioimaging and Therapy of Cancer*, Vogel, Carl-Wilhelm, ed., Oxford University Press: New York,(1987),28-55.

Weiss, Harvey J., et al., "Evidence for the Presence of Tissue Factor Activity on Subendothelium", *Blood*, 73, (1989),968-975.

Whittle, B., et al., "Vasoconstriction with Thromboxane A2 Induces Ulceration of the Gastric Mucosa", *Nature*, 292, (1981),472-474.

Wildgoose, Peter, et al., "Measurement of Basal Levels of Factor VIIa in Hemophilia A and B Patients", *Blood*, 80, (1992),25-28.

Williams W. J., et al., "The Fractionation of Russell's-Viper (*Vipera russellii*) Venom with Special Reference to the Coagulant Protein", *Biochemical Journal*, 84, (1962),52-62.

Wiman, Bjorn, "Affinity-Chromatographic Purification of Human x2-Antiplasmin", *Biochemical Journal*, 191, (1980),229-232.

Wiman, Bjorn, et al., "Purification and Characterization of Human Antiplasmin, the Fast-Acting Plasmin Inhibitor in Plasma", *European Journal of Biochemistry*, 78, (1977),19-26.

Winter, Greg, et al., "Man-Made Antibodies", *Nature*, 349, (1991),293-299.

Xu, Jianming, et al., "Expression and Immunochemical Analysis of Rat and Human Fibroblast Growth Factor Receptor (flg) Isoforms", *Journal of Biological Chemistry*, 267, (1992),17792-17803.

Yamaue, Hiroki, et al., "Functional and Phenotypic Analyses of Interleukin 2-Activated Tumor-Infiltrating Lymphocytes", *Biotherapy*, 2, (1990),247-259.

Yao, Rong : et al., "Human y-Glutamyl Hydrolase: Cloning and Characterization of the Enzyme Expressed in vitro", *Proceedings of the National Academy of Sciences*, 93, (1996),10134-10138.

Yao, Rong, et al., "Identification, Cloning, and Sequencing of a cDNA Coding for Rat y-Glutamyl Hydrolase", *Journal of Biological Chemistry*, 271, (1996),8525-8528.

Zamarron, Concepcion, et al., "A Receptor-induced Binding Site in Fibrinogen Elicited by Its Interaction with Platelet Membrane Glycoprotein IIb-IIIa", *Journal of Biological Chemistry*, 266, (1991),16193-16199.

Zhang, Lianshan, et al., "Preparation of Functionally Active Cell-Permeable Peptides by Single-Step Ligation of Two Peptide Modules", *Proceedings of the National Academy of Sciences*, 95, (1998),9184-9189.

* cited by examiner

Fig. 1A                Fig. 1B
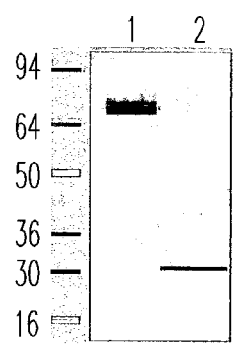  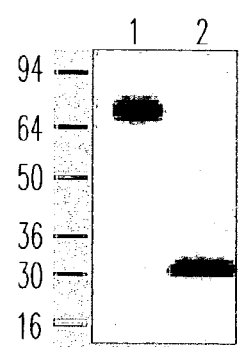
Fig. 2A                Fig. 2B

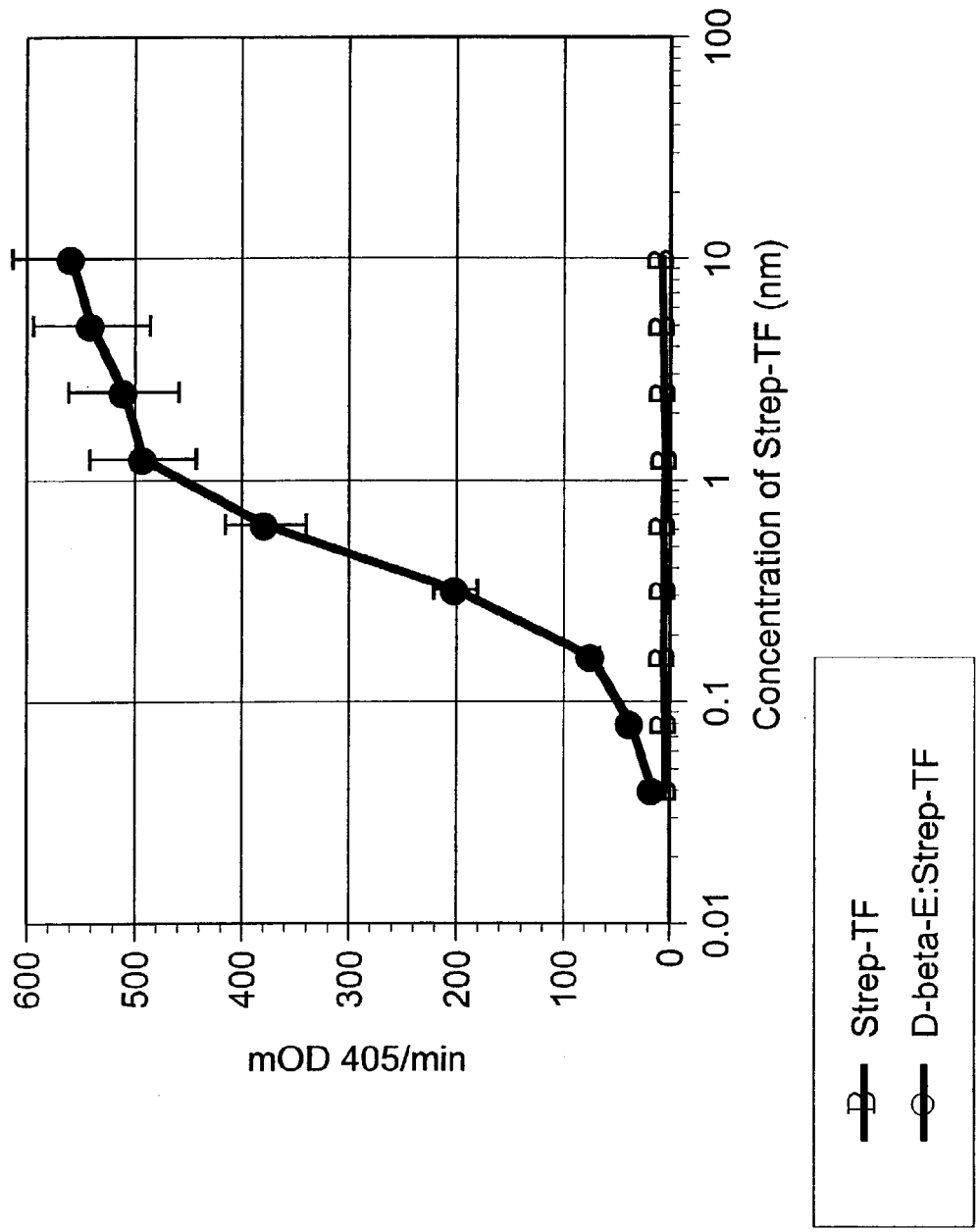
Fig. 9B
Fig. 9A

—— MOCK TREATMENT
—— DOX
- - - STVT
— — DOX + STVT

TARGETED THROMBOSIS

CROSS REFERENCE TO RELATED APPLICATIONS

This application is a non-provisional application which claims priority to provisional application entitled "Targeted Thrombosis" filed Sep. 20, 2002, U.S. Serial No. 60/412,194 and provisional application entitled "Targeted Thrombosis" filed Oct. 26, 2001, U.S. Ser. No. 60/336,331, the specifications of which are incorporated herein by reference.

This invention was made with Government support under Grant No. PO1 HL16411 awarded by the National Institutes of Health. The Government has certain rights in this invention.

FIELD OF THE INVENTION

The present invention relates to the fields of blood coagulation, thrombosis, tumor angiogenesis, and cancer therapy. The present invention provides various compositions and methods to treat solid tumors by inducing site-selective thrombosis in tumor blood vessels.

BACKGROUND OF THE INVENTION

Although many advances in cancer therapy have been made during the last thirty years, many prevalent forms of human cancer currently resist chemotherapeutic intervention. For example, prostate cancer is the second leading cause of cancer death in men. The incidence of prostate cancer has increased 141.8% between 1973 and 1994. In 1998, new prostate cancer cases totaled 184,500, representing about one new case every three minutes, and 29% of all new cancer cases in American men. In 1998, an estimated 39,200 men died of prostate cancer. A life is lost to prostate cancer in this country every 13 minutes. According to the National Cancer Institute, the annual cost of prostate cancer to the country, including medical care, lost wages and lost productivity, may be as high as $15 billion.

Certain types of tumors are more amenable to therapy than others because they are more accessible to therapeutic agents. For example, soft tissue tumors such as lymphomas, and tumors of the blood and blood-forming organs such as leukemia, have generally been more responsive to chemotherapeutic therapy than have solid tumors such as carcinomas. One reason for the susceptibility of soft and blood-based tumors to chemotherapy is that they are physically more accessible to chemotherapeutic intervention. It is simply more difficult for most chemotherapeutic agents to reach all of the cells of a solid tumor mass than it is for such agents to reach the cells of soft tumors and blood-based tumors. While it is possible to increase dosages, chemotherapeutic agents are toxic at higher doses. Hence, conventional anti-tumor agents generally have a limited range of effectiveness against solid tumors and a need exists for the development of novel strategies for the treatment of solid tumors.

One strategy for treating solid tumors is to use anti-tumor cell antibodies to deliver a toxin to the tumor cells. However, this method suffers from certain drawbacks. For example, antigen-negative or antigen-deficient cells can survive to repopulate the tumor or lead to further metastasis. Also, a solid tumor is generally impermeable to large molecules like antibodies, especially when linked to a toxin molecule.

Recently, there is increasing interest in developing methods to induce site-selective thrombosis within blood vessels of a selected tissue and thereby infarct and destroy that tissue. This approach derived from the notion that in order for a tumor to grow beyond a critical size, it must recruit and activate endothelial cells to form its own new microvasculature (Denekamp 1990; Folkman 1992). Some investigators have therefore targeted tumor blood vessels for destruction in order to destroy the supply of oxygen and nutrients needed for local tumor cells to proliferate and survive (Huang, Molema et al. 1997).

WO 96/01653 discloses antibodies against tumor vasculature markers to deliver thrombogens to the vasculature of solid tumors. Vascular targeting strategies are also described in Burrows et al. (1992), in Burrows and Thorpe (1993) and in WO 93/17715. U.S. Pat. No. 6,156,321 discloses that a truncated form of Tissue Factor can bind to A20 lymphoma cells when co-administered with a bispecific non-neutralizing antibody that binds to Tissue Factor and to an antigen on the A20 lymphoma cells.

SUMMARY OF THE INVENTION

The invention provides Selective Tissue Vascular Thrombogens (STVTs) that can induce targeted thrombosis, infarction and destruction of selected tissues, for example, tumors. Targeting the blood vessels of tumors has certain advantages in that it is not likely to lead to the development of resistant tumor cells or populations thereof. Delivery of Selective Tissue Vascular Thrombogens to blood vessels avoids the accessibility problems associated with targeting cells that are deep within a solid tumor. Moreover, destruction of the blood vessels may have an amplified anti-tumor effect because many tumor cells rely on a single vessel for their oxygen and nutrient supply.

The Selective Tissue Vascular Thrombogens (STVTs) of the invention are novel proteins having at least two functional domains. The first functional domain is a Tissue Factor polypeptide that can induce thrombogenesis, for example, the extracellular domain of Tissue Factor. The second functional domain is a Selective Binding Domain that can selectively bind to a cell-specific or tissue-specific molecule. Preferably, the Selective Binding Domain can bind to a molecule within a tumor, for example, a molecule on the luminal surface of a tumor blood channel. Upon binding, the Tissue Factor polypeptide can induce thrombosis.

Additional domains may be incorporated into the Selective Tissue Vascular Thrombogens of the invention. For example, Selective Tissue Vascular Thrombogens can include membrane associating domains or transmembrane domains of any protein known to one of skill in the art. Other domains that can be incorporated into the Selective Tissue Vascular Thrombogens of the invention include spacer domains to optimize spacing and/or interaction or non-interaction between elements of the domains.

Selective Binding Domains selectively localize the Selective Tissue Vascular Thrombogens, for example, a thrombogenic Tissue Factor domain, to a particular cell type, a particular tissue or a particular tumor type. However, to efficiently induce thrombosis, the Selective Binding Domain is selected to bind to a component within a blood channel. More than one Selective Binding Domain can be incorporated into the Selective Tissue Vascular Thrombogens of the invention, for example, to enhance thrombogenic function, and to increase the selectivity of localization or the selectivity of action.

According to the invention, certain tumor cells can form channels that mimic the function of blood vessels. The channels formed by such tumor cells are deep within the solid tumor and join with the normal circulatory system of the animal at the periphery of the tumor. Hence, Selective Binding Domains are preferably tumor cell membrane proteins that allow the Selective Tissue Vascular Thrombogens of the invention to bind with specificity to a selected tumor cell type.

Accordingly, the invention provides a Selective Tissue Vascular Thrombogen comprising a Selective Binding Domain associated with a Tissue Factor polypeptide. The Selective Binding Domain can bind to a channel for blood within a tissue and the human tissue factor can initiate thrombosis within the channel. The Selective Tissue Vascular Thrombogen can be made by covalent or non-covalent association of the Tissue Factor polypeptide with the Selective Binding Domain.

Such Selective Tissue Vascular Thrombogens can bind to channels within any tissue, for example, within a solid tumor. Such tissues can be lung, breast, ovary, stomach, pancreas, larynx, esophagus, testes, liver, parotid, biliary tract, colon, rectum, cervix, uterus, endometrium, kidney, bladder, prostate, thyroid, benign prostate hyperplasia, squamous cell carcinoma, adenocarcinoma, small cell carcinoma, melanoma, glioma, or neuroblastoma tissues or tumors. In one embodiment, the tissue is a prostate tumor. The Tissue Factor polypeptide is preferably a human Tissue Factor polypeptide, for example, a polypeptide comprising SEQ ID NO:3, SEQ ID NO:4, SEQ ID NO:5 or SEQ ID NO:6.

The Selective Binding Domain can be any molecule, peptide or polypeptide that can selectively bind or associate with a selected cell or tissue type. For example, the Selective Binding Domain can be a ligand for a cellular receptor, a receptor for a cellular ligand, or an inhibitor for a membrane-associated protein. The selective binding domain can, for example, bind selectively to endoglin, integrin, VEGF receptor, a glycosaminoglycan or Prostate Specific Membrane Antigen. In one embodiment, the selective binding domain is an integrin binding site from fibronectin. In another embodiment, the selective binding domain is an inhibitor of prostate specific membrane antigen, for example, Asp-β-Glu, N-succinyl-glutamic acid or quisqalic acid.

In certain embodiments, the Selective Tissue Vascular Thrombogen has SEQ ID NO:9 or SEQ ID NO:10.

The invention also provides therapeutic compositions comprising a therapeutically effective amount of at least one Selective Tissue Vascular Thrombogen of the invention and a pharmaceutically acceptable carrier, wherein the Selective Tissue Vascular Thrombogen comprises a Selective Binding Domain associated, fused or attached to a Tissue Factor polypeptide, wherein the Selective Binding Domain can bind to a channel for blood within a tissue and the Tissue Factor polypeptide can initiate a coagulation protease cascade within the channel. The Selective Tissue Vascular Thrombogen composition can also include a chemotherapeutic agent, a Factor VII polypeptide or a Factor VIIa polypeptide. Liposomes are one example of pharmaceutically acceptable carrier for the present compositions. In general, the therapeutic compositions are administered intravenously.

The invention further provides a method of treating a solid tumor in an animal that comprises administering a therapeutically effective amount of a Selective Tissue Vascular Thrombogen comprising a Selective Binding Domain fused or attached to a Tissue Factor polypeptide, wherein the Selective Binding Domain can bind to a channel for blood within a tumor and the human tissue factor can induce coagulation within the channel. The compositions of the invention can also be used in such therapeutic methods.

DESCRIPTION OF THE FIGURES

FIG. 1A provides a structural model of the ternary complex of Tissue Factor (blue molecule in the middle that projects through the cell membrane) with Factor VIIa (red molecule to the left) and Factor X (yellow molecule to the right that extends down to become) associated with a cell surface. The transmembrane domain of native Tissue Factor spans the cell membrane and ensures proper positioning of both Factor VIIa and Factor X (or Factor IX) on the cell surface. The interaction of the N-terminal Gla domain of both Factor VIIa and Factor X with the cell membrane is critical for the full thrombogenic activity of this complex.

FIG. 1B shows a structural model of a ternary complex of a Tissue-Selective Vascular Thrombogen of the invention where the Tissue Factor polypeptide (in the middle) is associated with Factor VIIa (on the left) and Factor X (on the right). The N-terminal extracellular domain of Tissue Factor is fused with a Selective Binding Domain (arrow in the upper left corner of the right panel (FIG. 1B)) to form a novel Tissue-Selective Vascular Thrombogen. The extreme portion of the N-terminus of Tissue Factor is not involved in its function. Hence, addition to the N-terminus of a Tissue Factor polypeptide of another molecule or domain is possible. In this invention, a Selective Binding Domain can be added to properly associate and physically align the Tissue Factor polypeptide with the cell surface. Attachment of such a Selective Binding Domain to its N-terminus does not adversely affect the conformation or the function of the selected Tissue Factor polypeptide. Factor VII, or its activated form, Factor VIIa, and Factor X, or Factor IX, can therefore interact with the Tissue Factor domain when aligned on a functionally supportive region of an anionic cell surface. Such interaction permits formation of a complex that has a conformation very similar to the structure of a native Tissue Factor:Factor VIIa:Factor Xa complex. The thrombogenic activity of this complex is substantially unaffected by the incorporated Selective Binding Domain.

FIG. 2A is a silver-stained SDS polyacrylamide gel of an electrophoretically purified fibronectin-Tissue Factor (Fn-TF) construct (lane 1) and a polypeptide encoding the extracellular domain of Tissue Factor (TF1-218) (lane 2). Only a single band was observed for each sample, indicative of the homogeneity and the purity of each protein preparation.

FIG. 2B is an anti-Tissue Factor western blot analysis of a replica gel of FIG. 2A, in which purified Fn-TF and TF1-218 proteins are present in lanes 1 and lane 2, respectively.

FIG. 3 graphically illustrates the ability of a fibronectin-Tissue Factor (Fn-TF) Tissue-Selective Vascular Thrombogen to act as cofactor for enhancement of Factor VIIa amidolytic activity. The amidolytic activity of Factor VIIa was measured as a function of the concentration of Tissue Factor (1-218) (•) or of the Fn-TF protein (O). These results indicate that the affinity of the Tissue Factor domain for Factor VIIa is not adversely affected by the incorporation of the fibronectin domain. Accordingly, the subtle protein-protein interactions between the Tissue Factor domain and the protease domain of Factor VIIa that are responsible for allosteric induction of Factor VIIa amidolytic function are not adversely affected.

FIG. 4 graphically illustrates the proteolytic activity of a complex between the Fn-TF protein and Factor VIIa (O), as compared with a complex between a Tissue Factor extracellular polypeptide (TF 1-218) and Factor VIIa (•). Increased proteolytic activity is observed with increasing concentrations of both Fn-TF and Tissue Factor. The activity curves for the two are very similar, suggesting that the incorporated fibronectin domain does not affect the recognition of factor X by the Fn-TF:VIIa protease complex.

Together, FIGS. 8A-8D indicate that PSMA-positive cells are tumor cells undergoing vasculogenic mimicry and forming channels that constitute part of the tumor vasculature.

FIG. 9A a silver-stained gel of purified Streptavidin-Tissue Factor.

FIG. 9B illustrates the activity of the D-β-E-biotin:streptavidin-Tissue Factor complex in a Factor X generation assay. The D-β-E-biotin:streptavidin-Tissue Factor construct (filled circle) has much more activity than the streptavidin-Tissue Factor construct (B symbols) that lacks the D-β-E Selective Binding Domain.

FIG. 10A illustrates that the treated tumor (left) was extensively necrotic compared to an untreated tumor (right). The center of the treated tumor was liquefied. However, there was still a rim of surviving tumor cells in the treated tumor.

FIG. 10B is a photomicrograph of a section of an untreated Mat Lu tumor. The tumor is undifferentiated and the majority of the tumor blood vessels are not visible.

FIG. 10C is a photomicrograph of a section of a Mat Lu tumor after repeated treatment with the D-β-E-streptavidin-Tissue Factor protein. The center of the tumor is necrotic and has collapsed into amorphous debris. Extensive vessel occlusion is visible.

FIG. 10D is a photomicrograph of a thrombotic vessel containing occlusive platelet aggregates, packed red blood cells, and fibrin. There are also large numbers of inflammatory cells that have infiltrated into the tumor.

DETAILED DESCRIPTION OF THE INVENTION

Figure 3:
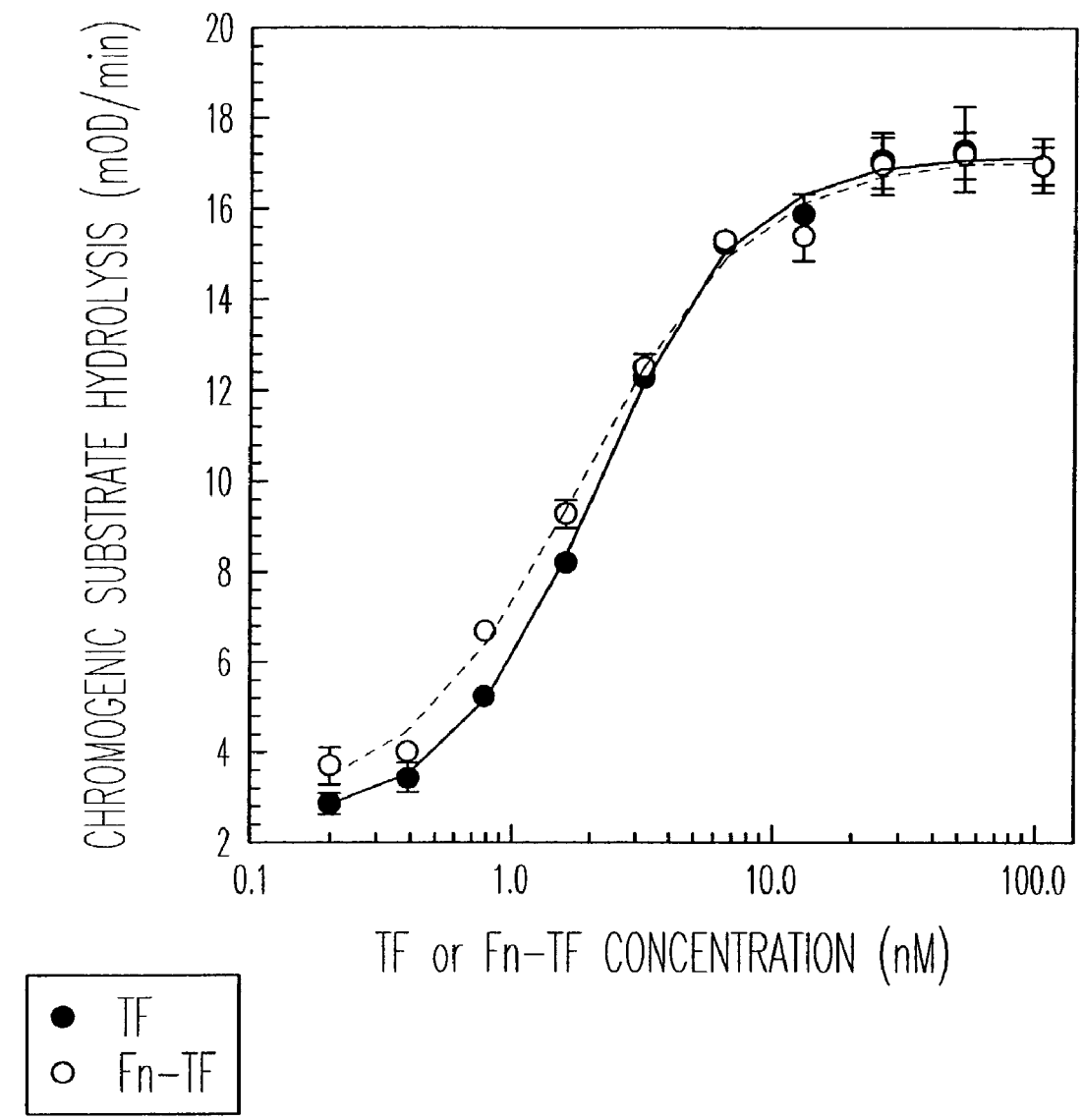

The present invention provides new compositions and methods for targeted thrombosis at selected vascular sites within an animal, for example, within tumors. Such targeted thrombosis is achieved by administering novel Tissue-Selective Vascular Thrombogens and compositions thereof. Such Tissue-Selective Vascular Thrombogens contain at least two domains. The first domain comprises a coagulation-activating Tissue Factor polypeptide. The second domain is a Selective Binding Domain. The Selective Binding Domain can recognize and bind to a selected cell type, for example, a specific tumor cell type. More than one Tissue Factor polypeptide and/or more than one Selective Binding Domain can be included in the Tissue-Selective Vascular Thrombogens of the invention.

Other domains can be incorporated into the Tissue-Selective Vascular Thrombogens of the invention. Such additional domains can be used, for example, to help spatially orient one or more of the other domains, to add additional Selective Binding Domains, to facilitate insertion of the Tissue-Selective Vascular Thrombogen into a cell membrane, to orient the Tissue-Selective Vascular Thrombogen with the cell surface or to enhance, or prevent neutralization of, the activity of the Tissue-Selective Vascular Thrombogen.

These compositions and methods can be used to activate the thrombogenic cascade in the tumor blood vessels, thereby blocking blood flow to the tumor and killing tumor cells within the tumor. The present invention provides that such compositions may be administered alone, in combination with conventional chemotherapeutics, in combination with Factor VIIa or other factors involved in the cascade of events leading to localized thrombogenesis.

Target Diseases

Angiogenesis in undesired locations is involved in wide range of diseases. The concepts, compositions and methods provided by this invention are broadly applicable to the treatment of any disease that has a vascular component, including benign or malignant tumors. Such vasculature-associated diseases include benign prostate hyperplasia (BPH), diabetic retinopathy, vascular restenosis, arteriovenous malformations (AVM), meningioma, hemangioma, neovascular glaucoma and psoriasis; and also angiofibroma, arthritis, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis and even endometriosis.

An important application of the present compositions and methods is to treat solid tumors. Typical vascularized tumors are the solid tumors, particularly carcinomas, which require a vascular component for the provision of oxygen and nutrients via the blood. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, neuroblastomas, and the like.

Table 1 is provided for the purpose of exemplifying human tumor cell lines that are publicly available. The information presented in Table 1 is provides by means of an example, and not intended to be limiting either by year or by scope. One of skill in the art may consult the ATCC Catalogue of any subsequent year to identify other appropriate cell lines. Also, if a particular cell type is desired, the means for obtaining such cells, and/or their instantly available source, will be known to those of skill in the particular art. An analysis of the scientific literature can thus readily reveal an appropriate choice of cell for any tumor cell type to be targeted.

TABLE 1

HUMAN TUMOR CELL LINES AND SOURCES

| ATTC/HTB NUMBER | CELL LINE | TUMOR TYPE |
|---|---|---|
| 1 | J82 | Transitional-cell carcinoma, bladder |
| 2 | RT4 | Transitional-cell papilioma, bladder |
| 3 | ScaBER | Squamous carcinoma, bladder |
| 4 | T24 | Transitional-cell carcinoma, bladder |
| 5 | TCCSUP | Transitional-cell carcinoma, bladder, primary grade IV |
| 9 | 5637 | Carcinoma, bladder, primary |
| 10 | SK-N-MC | Neuroblastoma, metastasis to supra-orbital area |
| 11 | SK-N-SH | Neuroblastoma, metastasis to bone marrow |
| 12 | SW 1088 | Astrocytoma |
| 13 | SW 1783 | Astrocytoma |
| 14 | U-87 MG | Glioblastoma, astrocytoma, grade III |
| 15 | U-118 MG | Glioblastoma |
| 16 | U-138 MG | Glioblastoma |
| 17 | U-373 MG | Glioblastoma, astrocytoma, grade III |
| 18 | Y79 | Retinoblastoma |
| 19 | BT-20 | Carcinoma, breast |
| 20 | BT-474 | Ductal carcinoma, breast |
| 22 | MCF7 | Breast adenocarcinoma, pleural effusion |
| 23 | MDA-MB-134-VI | Breast, ductal carcinoma, pleural effusion |
| 24 | MDA-MU-157 | Breast medulla, carcinoma, pleural effusion |
| 25 | MDA-MB-175-VII | Breast, ductal carcinoma, pleural effusion |

TABLE 1-continued

HUMAN TUMOR CELL LINES AND SOURCES

| ATTC/HTB NUMBER | CELL LINE | TUMOR TYPE |
|---|---|---|
| 27 | MDA-MB-361 | Adenocarcinoma, breast, metastasis to brain |
| 30 | SK-BR-3 | Adenocarcinoma, breast, malignant pleural effusion |
| 31 | C-33 A | Carcinoma, cervix |
| 32 | HT-3 | Carcinoma, cervix, metastasis to lymph node |
| 33 | ME-180 | Epidermoid carcinoma, cervix, metastasis to omentum |
| 34 | MS751 | Epidermoid carcinoma, cervix, metastasis to lymph node |
| 35 | SiHa | Squamous carcinoma, cervix |
| 36 | JEG-3 | Choriocarcinoma |
| 37 | Caco-2 | Adenocarcinoma, colon |
| 38 | HT-29 | Adenocarcinoma, colon, moderately well-differentiated grade II |
| 39 | SK-CO-1 | Adenocarcinoma, colon, ascites |
| 40 | HuTu 80 | Adenocarcinoma, duodenum |
| 41 | A-253 | Epidermoid carcinoma, submaxillary gland |
| 43 | FaDu | Squamous cell carcinoma, pharynx |
| 44 | A-498 | Carcinoma, kidney |
| 45 | A-704 | Adenocarcinoma, kidney |
| 46 | Caki-1 | Clear cell carcinoma, consistent with renal primary, skin metastasis |
| 47 | Caki-2 | Clear cell carcinoma, consistent with renal primary |
| 48 | SK-NEP-1 | Wilms' tumor, pleural effusion |
| 49 | SW 839 | Adenocarcinoma, kidney |
| 52 | SK-HEP-1 | Adenocarcinoma, liver, ascites |
| 53 | A-427 | Carcinoma, lung |
| 54 | Calu-1 | Epidermoid carcinoma grade III, lung, metastasis to pleura |
| 55 | Calu-3 | Adenocarcinoma, lung, pleural effusion |
| 56 | Calu-6 | Anaplastic carcinoma, probably lung |
| 57 | SK-LU-1 | Adenocarcinoma, lung consistent with poorly differentiated, grade III |
| 58 | SK-MES-1 | Squamous carcinoma, lung, pleural effusion |
| 59 | SW 900 | Squamous cell carcinoma, lung |
| 60 | EB1 | Burkitt lymphoma, upper maxilla |
| 61 | EB2 | Burkitt lymphoma, ovary |
| 62 | P3HR-1 | Burkitt lymphoma, ascites |
| 63 | HT-144 | Malignant melanoma, metastasis to subcutaneous tissue |
| 64 | Malme-3M | Malignant melanoma, metastasis to lung |
| 66 | RPMI-7951 | Malignant melanoma, metastasis to lymph node |
| 67 | SK-MEL-1 | Malignant melanoma, metastasis to lymphatic system |
| 68 | SK-MEL-2 | Malignant melanoma, metastasis to skin of thigh |
| 69 | SK-MEL-3 | Malignant melanoma, metastasis to lymph node |
| 70 | SK-MEL-S | Malignant melanoma, metastasis to auxiliary node |
| 71 | SK-MEL-24 | Malignant melanoma, metastasis to node |
| 72 | SK-MEL-28 | Malignant melanoma |
| 73 | SK-MEL-31 | Malignant melanoma |
| 75 | Caov-3 | Adenocarcinoma, ovary, consistent with primary |
| 76 | Caov-4 | Adenocarcinoma, ovary, metastasis to subserosa of fallopian tube |
| 77 | SK-OV-3 | Adenocarcinoma, ovary, malignant ascites |
| 78 | SW 626 | Adenocarcinoma, ovary |
| 79 | Capan-1 | Adenocarcinoma, pancreas, metastasis to liver |
| 80 | Capan-2 | Adenocarcinoma, pancreas |
| 81 | DU 145 | Carcinoma, prostate, metastasis to brain |
| 82 | A-204 | Rhabdomyosarcoma |
| 85 | Saos-2 | Osteogenic sarcoma, primary |
| 86 | SK-ES-1 | Anaplastic osteosarcoma versus Ewing sarcoma, bone |
| 88 | SK-LMS-1 | Leiomyosarcoma, vulva, primary |
| 91 | SW 684 | Fibrosarcoma |
| 92 | SW 872 | Liposarcoma |
| 93 | SW 982 | Axilla synovial sarcoma |
| 94 | SW 1353 | Chondrosarcoma, humerus |
| 96 | U-2 OS | Osteogenic sarcoma, bone primary |
| 102 | Malme-3 | Skin fibroblast |
| 103 | KATO III | Gastric carcinoma |
| 104 | Cate-1B | Embryonal carcinoma, testis, metastasis to lymph node |
| 105 | Tera-1 | Embryonal carcinoma, malignancy consistent with metastasis to lung |
| 106 | Tera-2 | Embryonal carcinoma, malignancy consistent with, metastasis to lung |
| 107 | SW579 | Thyroid carcinoma |
| 111 | AN3 CA | Endometrial adenocarcinoma, metastatic |
| 112 | HEC-1-A | Endometrial adenocarcinoma |
| 113 | HEC-1-B | Endometrial adenocarcinoma |
| 114 | SK-UT-1 | Uterine, mixed mesodermal tumor, consistent with leiomyosarcoma grade III |
| 115 | SK-UT-1B | Uterine, mixed mesodermal tumor, consistent with lelomyosarcoma grade III |
| 117 | SW 954 | Squamous cell carcinoma, vulva |
| 118 | SW 962 | Carcinoma, vulva, lymph node metastasis |
| 119 | NCI-H69 | Small cell carcinoma, lung |
| 120 | NCI-H128 | Small cell carcinoma, lung |
| 121 | BT-483 | Ductal carcinoma, breast |
| 122 | BT-549 | Ductal carcinoma, breast |
| 123 | DU4475 | Metastatic cutaneous nodule, breast carcinoma |
| 124 | HBL-100 | Breast |
| 125 | Hs 578Bst | Breast, normal |
| 126 | Hs 578T | Ductal carcinoma, breast |
| 127 | MDA-MB-330 | Carcinoma, breast |
| 128 | MDA-MB-415 | Adenocarcinoma, breast |
| 129 | MDA-MB-435S | Ductal carcinoma, breast |
| 130 | MDA-MB-436 | Adenocarcinoma, breast |
| 131 | MDA-MB-453 | Carcinoma, breast |
| 132 | MDA-MB-468 | Adenocarcinoma, breast |
| 133 | T-47D | Ductal carcinoma, breast, pleural effusion |
| 134 | Hs 766T | Carcinoma, pancreas, metastatic to lymph node |
| 135 | Hs 746T | Carcinoma, stomach, metastatic to left leg |
| 137 | Hs 695T | Amelanotic melanoma, metastatic to lymph node |
| 138 | Hs 683 | Glioma |
| 140 | Hs 294T | Melanoma, metastatic to lymph node |
| 142 | Hs 602 | Lymphoma, cervical |
| 144 | JAR | Choriocarcinoma, placenta |
| 146 | Hs 445 | Lymphoid, Hodgkin's disease |
| 147 | Ha 700T | Adenocarcinoma, metastatic to pelvis |
| 148 | H4 | Neuroglioma, brain |
| 151 | Hs 696 | Adenocarcinoma primary, unknown, metastatic to bone-sacrum |
| 152 | Hs 913T | Fibrosarcoma, metastatic to lung |
| 153 | Hs 729 | Rhabdomyosarcoma, left leg |
| 157 | FHs 738Lu | Lung, normal fetus |

TABLE 1-continued

HUMAN TUMOR CELL LINES AND SOURCES

| ATTC/HTB NUMBER | CELL LINE | TUMOR TYPE |
|---|---|---|
| 158 | FHs 173We | Whole embryo, normal |
| 160 | FHs 738B1 | Bladder, normal fetus |
| 161 | NIH:OVCAR-3 | Ovary, adenocarcinoma |
| 163 | Hs 67 | Thymus, normal |
| 166 | RD-ES | Ewing's sarcoma |
| 168 | ChaGo K-1 | Bronchogenic carcinoma, subcutaneous metastasis, human |
| 169 | WERI-Rb-1 | Retinoblastoma |
| 171 | NCI-H446 | Small cell carcinoma, lung |
| 172 | NCI-H209 | Small cell carcinoma, lung |
| 173 | NCI-H146 | Small cell carcinoma, lung |
| 174 | NCI-H441 | Papillary adenocarcinoma, lung |
| 175 | NCI-H82 | Small cell carcinoma, lung |
| 176 | H9 | T-cell lymphoma |
| 177 | NCI-H460 | Large cell carcinoma, lung. |
| 178 | NCI-H596 | Adenosquamous carcinoma, lung |
| 179 | NCI-H676B | Adenocarcinoma, lung |
| 180 | NCI-H345 | Small cell carcinoma, lung |
| 181 | NCI-H820 | Papillary adenocarcinoma, lung |
| 182 | NCI-H520 | Squamous cell carcinoma, lung |
| 183 | NCI-H661 | Large cell carcinoma, lung |
| 184 | NCI-H510A | Small cell carcinoma, extra-pulmonary origin, metastatic |
| 185 | D283 Med | Medulloblastoma |
| 186 | Daoy | Medulloblastoma |
| 187 | D341 Med | Medulloblastoma |
| 188 | AML-193 | Acute monocyte leukemia |
| 189 | MV4-11 | Leukemia biphenotype |

Tissue Factor

According to the invention, any Tissue Factor polypeptide that can initiate thrombosis and that includes the extracellular domain of Tissue factor can be used as the Tissue Factor domain of the present Selective Tissue Vascular Thrombogens. The Tissue Factor polypeptide can be mutant or wild type. The Tissue Factor polypeptide can include all of the extracellular domain or part of it. Preferably, the Tissue Factor polypeptide is not the full-length native Tissue Factor. For example, the Tissue Factor polypeptide generally lacks the cytoplasmic domain, and may have none or only a part of the transmembrane domain.

Tissue Factor is the major receptor for initiating thrombogenic (blood coagulation) cascades (Davie, et al. 1991). Human Tissue Factor has been cloned and is available to those of skill in the art (Morrissey et al., 1987; Edgington et al., 1991; U.S. Pat. No. 5,110,730). In certain early studies, the same protein currently identified as human Tissue Factor may be referred to as human Tissue Factor heavy chain protein or the heavy chain of Tissue Factor. The gene encodes a polypeptide precursor of 295 amino acids in length, which includes a peptide leader with alternative cleavage sites, which is lead to the formation of a protein of 263 amino acids in length. Mature Tissue Factor is a single chain, 263 amino acid membrane glycoprotein (SEQ ID NO:2), and its primary sequence has structural similarity with the cytokine receptor family (Edgington et al., 1991). The recombinant expression of human Tissue Factor in CHO cells has been reported to lead to the production of Tissue Factor at a level that is described as being one of the highest expression levels reported for a recombinant transmembrane receptor following production in mammalian cells (Rehemtulla et al., 1991).

The amino acid sequence of the precursor form of human Tissue Factor (SEQ ID NO:1) is provided below:

```
-32  METPAWPRVP RPETAVARTL LLGWVFAQVA GA

1  SGTTNTVAAY NLTWKSTNFK TILEWEPKPV NQVYTVQIST

41  KSGDWKSKCF YTTDTECDLT DEIVKDVKQT YLARVFSYPA

81  GNVESTGSAG EPLYENSPEF TPYLETNLGQ PTIQSFEQVG

121  TKVNVTVEDE RTLVRRNNTF LSLRDVFGKD LIYTLYYWKS

161  SSSGKKTAKT NTNEFLIDVD KGENYCFSVQ AVIPSRTVNR

201  KSTDSPVECM GQEKGEFREI FYIIGAVVFV VIILVIILAI

241  SLHKCRKAGV GQSWKENSPL NVS
```

The amino acid sequence of the mature form of human Tissue Factor (SEQ ID NO:2) is provided below:

```
  1  SGTTNTVAAY NLTWKSTNFK TILEWEPKPV NQVYTVQIST

41  KSGDWKSKCF YTTDTECDLT DEIVKDVKQT YLARVFSYPA

81  GNVESTGSAG EPLYENSPEF TPYLETNLGQ PTIQSFEQVG

121  TKVNVTVEDE RTLVRRNNTF LSLRDVFGKD LIYTLYYWKS

161  SSSGKKTAKT NTNEFLIDVD KGENYCFSVQ AVIPSRTVNR

201  KSTDSPVECM GQEKGEFREI FYIIGAVVFV VIILVIILAI

241  SLHKCRKAGV GQSWKENSPL NVS
```

The amino acid sequence of the extracellular domain of human Tissue Factor (SEQ ID NO:3), which is sometimes called TF1-219, is provided below:

```
  1  SGTTNTVAAY NLTWKSTNFK TILEWEPKPV NQVYTVQIST

41  KSGDWKSKCF YTTDTECDLT DEIVKDVKQT YLARVFSYPA

81  GNVESTGSAG EPLYENSPEF TPYLETNLGQ PTIQSFEQVG

121  TKVNVTVEDE RTLVRRNNTF LSLRDVFGKD LIYTLYYWKS

161  SSSGKKTAKT NTNEFLIDVD KGENYCFSVQ AVIPSRTVNR

201  KSTDSPVECM GQEKGEFRE
```

The amino acid sequence of a slightly shorter extracellular domain of human Tissue Factor (SEQ ID NO:4), which is sometimes called TF1-218, is provided below:

```
  1  SGTTNTVAAY NLTWKSTNFK TILEWEPKPV NQVYTVQIST

41  KSGDWKSKCF YTTDTECDLT DEIVKDVKQT YLARVFSYPA

81  GNVESTGSAG EPLYENSPEF TPYLETNLGQ PTIQSFEQVG

121  TKVNVTVEDE RTLVRRNNTF LSLRDVFGKD LIYTLYYWKS

161  SSSGKKTAKT NTNEFLIDVD KGENYCFSVQ AVIPSRTVNR

201  KSTDSPVECM GQEKGEFR
```

A slightly truncated extracellular domain of human Tissue Factor that is sometimes called TF3-219 (SEQ ID NO:5), because it does not have the first two amino acids of SEQ ID NO:3, can also be used as a Tissue Factor polypeptide in the Tissue-Selective Vascular Thrombogens of the invention. This TF3-219 polypeptide has SEQ ID NO:5, provided below:

```
  1  TTNTVAAYNL  TWKSTNFKTI  LEWEPKPVNQ  VYTVQISTKS
 41  GDWKSKCFYT  TDTECDLTDE  IVKDVKQTYL  ARVFSYPAGN
 81  VESTGSAGEP  LYENSPEFTP  YLETNLGQPT  IQSFEQVGTK
121  VNVTVEDERT  LVRRNNTFLS  LRDVFGKDLI  YTLYYWKSSS
161  SGKKTAKTNT  NEFLIDVDKG  ENYCFSVQAV  IPSRTVNRKS
201  TDSPVECMGQ  EKGEFRE
```

A similar amino acid sequence of a slightly truncated extracellular domain of human Tissue Factor that is sometimes called TF3-218 (SEQ ID NO:6), because it does not have the first two amino acids of SEQ ID NO:3, can also be used as a Tissue Factor polypeptide in the Tissue-Selective Vascular Thrombogens of the invention. This TF3-218 polypeptide has SEQ ID NO:6, provided below:

```
  1  TTNTVAAYNL TWKSTNFKTI LEWEPKPVNQ VYTVQISTKS
 41  GDWKSKCFYT TDTECDLTDE IVKDVKQTYL ARVFSYPAGN
 81  VESTGSAGEP LYENSPEFTP YLETNLGQPT IQSFEQVGTK
121  VNVTVEDERT LVRRNNTFLS LRDVFGKDLI YTLYYWKSSS
161  SGKKTAKTNT NEFLIDVDKG ENYCFSVQAV IPSRTVNRKS
201  TDSPVECMGQ EKGEFR
```

Moreover, the C-terminal end of the Tissue Factor polypeptide can be manipulated as desired by one of skill in the art. For example, the transmembrane domain of Tissue Factor starts at about amino acid 220 and ends at about amino position 241. This domain and the cytoplasmic sequences that lie C-terminal to this domain can be removed and replaced with other polypeptide sequences, for example, other tranmembrane domains. In addition, a peptide comprising approximate amino acid position 211 to approximate amino acid position 219 can be removed and replaced with any convenient peptide sequence that can link a transmembrane domain to the active portion of Tissue Factor. Any such manipulations can be performed to modify or enhance the activity or membrane association propertied of the STVT, so long as the Tissue Factor domain retains activity and is capable of initiated a thrombogenic response.

A number of domains can be used to facilitate association of Tissue Factor with a selected cellular membrane. For example, a membrane association domain can be provided by the Selective Binding Domain or by any membrane protein or member of the Superfamily of Hematopoietic-Cytokine Receptors selected by one of skill in the art. In one embodiment, the Selective Tissue Vascular Thrombogens of the invention includes the entire transmembrane domain of human Tissue Factor, or a portion thereof. The amino acid sequence of the transmembrane domain of human Tissue Factor (SEQ ID NO:7) is provided below:

```
FYIIGAVVFV VIILVIILAI SL
```

Tissue Factor is a transmembrane cell surface receptor. Tissue Factor functions as the receptor and requisite cofactor for Factors VII and VIIa. Tissue Factor binds Factor VIIa to form a proteolytically active binary complex on the cell surface (Ruf and Edgington, 1991 b, 1994; Ruf et al., 1991, 1992a, 1992b). This complex rapidly activates the serine protease zymogens Factors IX and X by limited proteolysis, leading to the formation of thrombin and, then to the conversion of plasma fibrinogen to fibrin resulting in gelation of plasma and blood.

FIG. 1A provides a structural model of the ternary complex of Tissue Factor (having a transmembrane and a cytoplasmic domain) with Factor VIIa (red molecule to the left) and Factor X (yellow molecule to the right that extends down to become) as this complex becomes associated with a cell surface. The transmembrane domain of native Tissue Factor spans the cell membrane and ensures proper positioning of both Factor VIIa and Factor X (or Factor IX) on the cell surface. The interaction of the N-terminal Gla domain of both Factor VIIa and Factor X with the cell membrane is critical for the full thrombogenic activity of this complex.

A limited number of cells constitutively express Tissue Factor. Lung and central nervous system tissues contain high levels of Tissue Factor activity, with Tissue Factor being found in bronchial mucosa and alveolar epithelial cells in the lung and in glial cells and astrocytes in the nervous system. Expression of Tissue Factor has also been reported in cardiac myocytes, renal glomeruli, and in certain epithelial or mucosal tissues of the intestine, bladder and respiratory tract. Over expression of Tissue Factor has been linked to thrombotic diseases and sepsis (Drake, Morrissey et al. 1989; Levi, ten Cate et al. 1994). Tissue Factor expression on endothelial cells and monocytes is induced by exposure to inflammatory cytokines and bacterial lipopolysaccaride (Drake and Pang 1989; Oeth, Pany et al. 1994). There can also be very small amounts of Tissue Factor associated with membrane vesicles shed by cells into the blood. Tissue Factor is generally constitutively expressed at tissue barriers between body tissues and the external environment (Drake et al., 1989; Ruf and Edgington, 1994). The expression of Tissue Factor in this manner acts as an envelope that allows Tissue Factor to arrest bleeding.

The disruption of the Tissue Factor gene in mice revealed an unexpected role for Tissue Factor in supporting vascular development (Carmeliet, Mackman et al. 1996). Beside the roles it has in hemostasis and thrombosis, Tissue Factor is also implicated in signal transduction (Zioncheck, Roy et al. 1992), cellular adhesion (Ott, Fischer et al. 1998), and the tumor metastasis and angiogenesis (Mueller and Ruf 1998).

Tissue Factor is typically not expressed to any significant degree on blood cells or on the surface of endothelial cells that form the vasculature, but such expression can be induced in endothelial cells and monocytes within the vasculature by infectious agents and certain inflammatory processes. Monocytes, for example, are induced to express Tissue Factor by cytokines and T cells. Expression of Tissue Factor in the vasculature can result in disseminated intravascular coagulation or localized initiation of blood clots or thrombogenesis. In this context, it is important to note that Tissue Factor must be available at all sites of the body where hemostasis would be necessary following tissue damage, infection or other insults.

Tissue Factor is the major initiator of the blood coagulation protease cascades and is generally not in direct contact with the blood under physiologically normal conditions (Osterud et al., 1986; Nemerson, 1988; Broze, 1992; Ruf and Edgington, 1994). After vascular damage or activation by certain cytokines or endotoxin, however, Tissue Factor is exposed to the blood by the exposure of (sub)endothelial tissue and cells (Weiss et al., 1989), by induction within the endothelium, or by certain blood cells (Warr et al., 1990). Tissue Factor then complexes with Factor VII and VIIa, which under normal conditions circulate at low concentrations in the blood (Wildgoose et al., 1992). The Tissue Factor:Factor VII complex is converted to a Tissue Factor:Factor VIIa complex. The Tissue Factor/Factor VIIa complex starts the coagulation cascade through the activation of Factor X to Factor Xa. Ultimately, the cascade results in formation of thrombin that produces fibrin.

For this sequence of events to occur, the Tissue Factor: Factor VIIa complex must be associated with a supportive phospholipid membrane surface in order for efficient assembly of the coagulation-initiation complexes with Factors IX or X (Ruf and Edgington, 1991a; Ruf et al., 1992c; Paborsky et al., 1991; Bach et al., 1986; Krishnaswamy et al., 1992; ten Cate et al., 1993). The association of Tissue Factor with an anionic phospholipid membrane increases the coagulative activity of this complex by promoting the proper orientation of Factor VIIa relative to Tissue Factor through the interaction of Gla domain of Factor VIIa with phospholipid. This enhances the binding of Factor VIIa to Tissue Factor, facilitates the catalytic conversion of Factor VII to Factor VIIa, and enhances the activity of Tissue Factor:Factor VIIa toward its substrates, Factor X and Factor IX. It also provides a cellular membrane binding for Factor X and Factor IX.

A recombinant form of Tissue Factor has been constructed that contains only the cell surface or extracellular domain (Ruf et al., 1991b; Stone, et al., 1995) and that lacks the transmembrane and cytoplasmic regions of Tissue Factor. This truncated Tissue Factor is 219 amino acids in length and is a soluble protein with approximately $10^5$ times less factor X-activating activity than native Tissue Factor in an appropriate phospholipid membrane environment (Ruf, et al., 1991b). This difference in activity is related to the association of Tissue Factor and the lack of membrane-association by truncated Tissue Factor. The Tissue Factor:VIIa complex binds and activates Factors IX and X far more efficiently when associated with a negatively charged phospholipid surface (Ruf, et al., 1991b; Paborsky, et al., 1991). Consequently, the native transmembrane Tissue Factor is 100,000 fold more active than the soluble Tissue Factor extracellular domain. In order to achieve site-selective induction of thrombosis to occlude undesired vessels under pathologic conditions using Tissue Factor, a soluble Tissue Factor molecule that retains coagulative function upon proper positioning onto a cell surface structure is desirable.

However, according to the present invention, the extracellular domain of Tissue Factor, without the natural transmembrane and cytoplasmic regions of Tissue Factor, can promote blood coagulation when properly associated with a cellular membrane by any "Selective Binding Domain."

Selective Binding Domains

A Selective Binding Domain is a peptide, peptidyl analogue or polypeptide that can associate with a cellular membrane, through direct interaction with the membrane or through interaction with a protein present on the membrane, or both. Association with the cellular membrane by the Selective Binding Domain need only be transient, however, it must be selective so that the Selective Tissue Vascular Thrombogen can provide targeted, localized thrombosis.

One or more Selective Binding Domains are associated or integrated with one or more Tissue Factor polypeptides to form a Selective Tissue Vascular Thrombogen. Association between the Tissue Factor polypeptide(s) and the Selective Binding Domain(s) can be via a covalent bond, or via any other stable interaction, such as by hydrogen bonding.

FIG. 1B shows a structural model of a ternary complex of a Tissue-Selective Vascular Thrombogen of the invention where the Tissue Factor polypeptide (in the middle) is associated with Factor VIIa (on the left) and Factor X (on the right). The N-terminal extracellular domain of Tissue Factor is fused with a Selective Binding Domain (arrow in the upper left corner of FIG. 1B) to form a novel Tissue-Selective Vascular Thrombogen. The extreme portion of the N-terminus of Tissue Factor is not involved in its function. Hence, addition of another molecule or domain to the N-terminus of a Tissue Factor polypeptide is possible. In this invention, a Selective Binding Domain can be added to properly associate and physically align the Tissue Factor polypeptide with the cell surface. Attachment of such a Selective Binding Domain to its N-terminus does not adversely affect the conformation or the function of the selected Tissue Factor polypeptide. Factor VII, or its activated form, Factor VIIa, and Factor X, or Factor IX, can therefore interact with the Tissue Factor domain when aligned on a functionally supportive region of an anionic cell surface. Such interaction permits formation of a complex that has a conformation very similar to the structure of a native Tissue Factor:Factor VIIa:Factor Xa complex. The thrombogenic activity of this complex is substantially unaffected by the incorporated Selective Binding Domain.

A Selective Binding domain can be a ligand for a cellular receptor, a membrane-associated domain for any cell membrane protein known to one of skill in the art, an inhibitor for a membrane-associated protein, a component of tumor vasculature, a component that binds to, or is generally associated with, tumor cells, a component that binds to, or is generally associated with, tumor vasculature, a component of the tumor extracellular matrix or stroma, a cell found within the tumor vasculature or any peptide or polypeptide that preferentially interacts with a cellular membrane. In general the Selective Binding domain is preferably not an antibody.

Selective Binding domains can be made to bind to any relatively specific marker on the tumor cell, for example, endoglin, integrin, VEGF receptor, PSMA and the like. Many so-called "tumor antigens" have been described, any one which could be employed as a target to which the Selective Binding domain may bind. A large number of exemplary solid tumor-associated antigens are listed herein in Table 2.

TABLE 2

| | Marker Antigens of Solid Tumors | | |
|---|---|---|---|
| Tumor Site | Antigen Identity/ Characteristics | Monoclonal Antibodies | Reference |
| GYNECOLOGICAL | | | |
| GY | CA 125 > 200 kD mucin GP | OC 125 | Kabawat et al., 1983; Szymendera, 1986 |

TABLE 2-continued Marker Antigens of Solid Tumors

| Tumor Site | Antigen Identity/ Characteristics | Monoclonal Antibodies | Reference |
|---|---|---|---|
| Ovarian | 80 Kd GP | OC 133 | Masuko et al, Cancer Res., 1984 |
| Ovarian | SGA 360 Kd GP | OMI | de Krester et al., 1986 |
| Ovarian | High $M_r$ mucin | MO v1 | Miotti et al, Cancer Res., 1985 |
| Ovarian | High $M_r$ mucin/ glycolipid | MO v2 | Miotti et al, Cancer Res., 1985 |
| Ovarian | NS | 3C2 | Tsuji et al., Cancer Res., 1985 |
| Ovarian | NS | 4C7 | Tsuji et at., Cancer Res., 1985 |
| Ovarian | High $M_r$ mucin | $ID_3$ | Gangopadhyay et al., 1985 |
| Ovarian | High $M_r$ mucin | DU-PAN-2 | Lan et al., 1985 |
| GY | 7700 Kd GP | F 36/22 | Croghan Ct at., 1984 |
| Ovarian | 'gp 68' 48 Kd | $4F_7/A_{10}$ | Bhattacharya et al., 1984 |
| GY | 40, 42 kD GP | OV-TL3 | Poels et al., 1986 |
| GY | 'TAG-72' High $M_r$ mucin | B72.3 | Thor et al., 1986 |
| Ovarian | 300-400 Kd GP | $DF_3$ | Kufe et al., 1984 |
| Ovarian | 60 Kd GP | $2C_8/2F_7$ | Bhattacharya et al., 1985 |
| GY | 105 Kd GP | MF 116 | Mattes et al., 1984 |
| Ovarian | 38-40 kD GP | MOv18 | Miotti et al., 1987 |
| GY | CEA 180 Kd GP | CEA 11-H5 | Wagener et al., 1984 |
| Ovarian | CA 19-9 or GICA | CA 19-9 (1116NS 19-9) | Atkinson et al., 1982 |
| Ovarian | 'PLAP' 67 Kd GP | H17-E2 | McDicken et al., 1985 |
| Ovarian | 72 Kd | 791T/36 | Perkins et al., 1985 |
| Ovarian | 69 Kd PLAP | $NDOG_2$ | Sunderland et al., 1984 |
| Ovarian | unknown $M_r$ PLAP | H317 | Johnson et al., 1981 |
| Ovarian | p185$^{HER2}$ | 4D5, 3H4, 7C2, 6E9, 2C4, 7F3, 2H11, 3E8, 5B8, 7D3, SB8 | Shepard et al., 1991 |
| uterus ovary | HMFG-2 | HMFG2 | Epenetos et al., 1982 |
| GY | HMFG-2 | 3.14.A3 | Butchell et al., 1983 |
| BREAST | 330-450 Kd GP | DF3 | Hayes et al., 1985 |
| | NS | NCRC-11 | Ellis et al., 1984 |
| | 37 kD | 3C6F9 | Mandeville et al., 1987 |
| | NS | MBE6 | Teramoto et al., 1982 |
| | NS | CLNH5 | Glassy et al., 1983 |
| | 47 Kd GP | MAC 40/43 | Kjeldsen et al., 1986 |
| | High $M_r$ GP | EMA | Sloane et al., 1981 |
| | High $M_r$ GP | HMFG1 HFMG2 | Arklie et al., 1981 |
| | NS | 3.15.C3 | Arklie et al., 1981 |

TABLE 2-continued

Marker Antigens of Solid Tumors

| Tumor Site | Antigen Identity/ Characteristics | Monoclonal Antibodies | Reference |
|---|---|---|---|
| | NS | M3, M8, M24 | Foster et al., 1982 |
| | 1 (Ma) blood group Ags | M18 | Foster et al., 1984 |
| | NS | 67-D-11 | Rasmussen et al., 1982 |
| | oestrogen receptor | D547Sp, D75P3, H222 | Kinsel et al., 1989 |
| | EGF Receptor | Anti-EGF | Sainsbury et al., 1985 |
| | Laminin Receptor | LR-3 | Horan Hand et al., 1985 |
| | Erb B-2 p185 | TA1 | Gusterson et al., 1988 |
| | NS | H59 | Hendler et al., 1981 |
| | 126 Kd GP | 10-3D-2 | Soule et al., 1983 |
| | NS | HmAB1,2 | Imam et al., 1984; Schlom et al., 1985 |
| | NS | MBR 1,2,3 | Menard et al., 1983 |
| | 95 Kd | 24.17.1 | Thompson et al., 1983 |
| | 100 Kd | 24.17.2 (3E1.2) | Croghan et al., 1983 |
| | NS | F36/22.M7/ 105 | Croghan et al., 1984 |
| | 24 Kd | C11, G3, H7 | Adams et al., 1983 |
| | 90 Kd GP | B6.2 | Colcher Ct al., 1981 |
| | CEA & 180 Kd GP | B1.1. | Colcher et al., 1983 |
| | Colonic & pancreatic mucin similar to Ca 19-9 | Cam 17.1 | Imperial Cancer Research Technology MAb listing |
| | milk mucin core protein | SM3 | Imperial Cancer Research Technology MAb listing |
| | milk mucin core protein | SM4 | Imperial Cancer Research Technology MAb listing |
| | Affinity-purified milk mucin | C-Mul (566) | Imperial Cancer Research Technology MAb listing |
| | $p185^{HER2}$ | 4D5, 3H4, 7C2, 6E9, 2C4, 7F3, 2H11, 3E8, 5B8, 7D3, SB8 | Shepard et al., 1991 |
| | CA 125 > 200 Kd GP | OC 125 | Kabawat et al., 1985 |
| | High $M_r$ mucin/ glycoprotein | MO v2 | Miotti et al., 1985 |
| | High $M_r$ mucin | DU-PAN-2 | Lan et al., 1984 |
| | 'gp48' 48 Kd GP | $4F_7/7A_{10}$ | Bhattacharya et al., 1984 |
| | 300-400 Kd GP | $DF_3$ | Kufe et al., 1984 |
| | 'TAG-72' high $M_r$ mucin | B72.3 | Thor et al., 1986 |
| | 'CEA' 180 Kd GP | cccccCEA 11 | Wagener et al., 1984 |
| | 'PLAP' 67 Kd GP | H17-E2 | McDicken et al., 1985 |

TABLE 2-continued

Marker Antigens of Solid Tumors

| Tumor Site | Antigen Identity/ Characteristics | Monoclonal Antibodies | Reference |
|---|---|---|---|
| | HMFG-2 > 400 Kd GP | 3.14.A3 | Burchell et al., 1983 |
| | NS | FO23C5 | Riva et al., 1988 |
| COLORECTAL | | | |
| | TAG-72 High $M_r$ mucin | B72.3 | Colcher et al., 1987 |
| | GP37 | (17-1A) 1083-17-1A | Paul et al., 1986 |
| | Surface GP | CO17-1A | LoBuglio et al., 1988 |
| | CEA | ZCE-025 | Patt et al., 1988 |
| | CEA | AB2 | Griffin et al., 1988a |
| | Cell surface AG secretory epithelium | HT-29-15 250-30.6 | Cohn et al., 1987 Leydem et al., 1986 |
| | Surface glycoprotein | 44 × 14 | Gallagher et al., 1986 |
| | NS | A7 | Takahashi et al., 1988 |
| | NS | GA73.3 | Munz et al., 1986 |
| | NS | 791T/36 | Farrans et al., 1982 |
| | cell membrane & cytoplasmic Ag | 28A32 | Smith et al., 1987 |
| | CEA & vindesine gp72 | 28.19.8 x MMCO-791 | Corvalen, 1987 Byers et al., 1987 |
| | High $M_r$ mucin | DU-PAN-2 | Lan et al., 1985 |
| | High $M_r$ mucin | $ID_3$ | Gangopadhyay et al., 1985 |
| | CEA 180 Kd GP | CEA 11-H5 | Wagener et al., 1984 |
| | 60 Kd GP | $2C_8/2F_7$ | Bhattacharya et al., 1985 |
| | CA-19-9 (or GICA) | C-19-9 (1116NS 19-9) | Atkinson et al., 1982 |
| | Lewis a | PR5C5 | Imperial Cancer Research Technology Mab Listing |
| | Lewis a | PR4D2 | Imperial Cancer Research Technology Mab Listing |
| | Colonic mucus | PR4D1 | Imperial Cancer Research Technology Mab Listing |
| MELANOMA | | | |
| | $p97^a$ | 4.1 | Woodbury et al., 1980 |
| | $p97^a$ | $8.2\ M_{17}$ | Brown, et al., 1981a |
| | $p97^b$ | 96.5 | Brown, et al., 1981a |
| | $p97^c$ | 118.1, 133.2, (113.2) | Brown, et al., 1981a |
| | $p97^c$ | $L_1, L_{10}, R_{10\ (R19)}$ | Brown, et al., 1981b |
| | $p97^d$ | $I_{12}$ | Brown, et al., 1981b |
| | $p97^e$ | $K_5$ | Brown et al., 1981b |
| | p155 | 6.1 | Loop et al., 1981 |
| | $G_{D3}$ disialoganglioside | R24 | Dippold et al., 1980 |
| | p210, p60, p250 | 5.1 | Loop et. al., 1981 |

TABLE 2-continued

Marker Antigens of Solid Tumors

| Tumor Site | Antigen Identity/ Characteristics | Monoclonal Antibodies | Reference |
|---|---|---|---|
| | p280 p440 | 225.28S | Wilson et al., 1981 |
| | GP 94, 75, 70 & 25 | 465.12S | Wilson et al., 1981 |
| | P240-P250, P450 | 9.2.27 | Reisfeld et al., 1982 |
| | 100, 77, 75 Kd | F11 | Chee et al., 1982 |
| | 94 Kd | 376.96S | Imai et al., 1982 |
| | 4 GP chains | 465.12S | Imai et al., 1982; Wilson et al., 1981 |
| | GP 74 | 15.75 | Johnson & Reithmuller, 1982 |
| | GP49 | 15.95 | Johnson & Reithmuller, 1982 |
| | 230 Kd | Mel-14 | Carrel et al., 1982 |
| | 92 Kd | Mel-12 | Carrel et al., 1982 |
| | 70 Kd | Me3-TB7 | Carrel et al. 1982 |
| | HMW MAA similar to 9.2.27 AG | 225.28SD | Kantor et al., 1982 |
| | HMW MAA similar to 9.2.27 AG | 763.24TS | Kantor et al., 1982 |
| | GP95 similar to 376.96S 465.125 | 705F6 | Stuhlmiller et al., 1982 |
| | GP12S | 436910 | Saxton et al., 1982 |
| | CD41 | M148 | Imperial Cancer Research Technology Mab listing |
| GASTROINTESTINAL | | | |
| | High $M_r$ mucin | ID3 | Gangopadhyay et al., 1985 |
| gall bladder, pancreas, stomach | High $M_r$ mucin | DU-PAN-2 | Lan et al., 1985 |
| pancreas | NS | OV-TL3 | Poels et al., 1984 |
| pancreas, stomach, oesophagus | 'TAG-72' high $M_r$ mucin | B72.3 | Thor et al., 1986 |
| stomach | 'CEA' 180 Kd GP | CEA 11-H5 | Wagener et al., 1984 |
| pancreas | HMFG-2 > 400 Kd GP | 3.14.A3 | Burchell et al., 1983 |
| G.I. | NS | C COLI | Lemkin et al., 1984 |
| pancreas, stomach | CA 19-9 (or GICA) | CA-19-9 (1116NS 19-9) and CA50 | Szymendera, 1986 |
| pancreas | CA125 | GP OC125 | Szymendera, 1986 |
| LUNG | | | |
| non-small cell lung carcinoma | p185$^{HER2}$ | 4D5, 3H4, 7C2, 6E9, 2C4, 7F3, 2H11, 3E8, 5B8, 7D3, SB8 | Shepard et al., 1991 |
| | high $M_r$ mucin/ glycolipid | MO v2 | Miotti et al., 1985 |
| | 'TAG-72' high $M_r$ mucin | B72.3 | Thor et al., 1986 |
| | high $M_r$ mucin | DU-PAN-2 | Lan et al., 1985 |
| | 'CEA' 180 kD GP | CEA 11-H5 | Wagener et al., 1984 |

TABLE 2-continued

Marker Antigens of Solid Tumors

| Tumor Site | Antigen Identity/ Characteristics | Monoclonal Antibodies | Reference |
|---|---|---|---|
| Malignant Gliomas | cytoplasmic antigen from 85HG-22 cells | MUC 8-22 | Stavrou, 1990 |
| | cell surface Ag from 85HG-63 cells | MUC 2-63 | Stavrou, 1990 |
| | cell surface Ag from 85HG-63 cells | MUC 2-39 | Stavrou, 1990 |
| | cell surface Ag from 85HG-63 cells | MUC 7-39 | Stavrou, 1990 |
| MISCELLANEOUS | | | |
| | p53 | PAb 240, PAb 246, PAb 1801 | Imperial Cancer Research Technology MaB Listing |
| small round cell tumors | neural cell adhesion molecule | ERIC.1 | Imperial Cancer Research Technology MaB Listing |
| medulloblastoma neuroblastoma rhabdomyosarcoma | | M148 | Imperial Cancer Research Technology MaB Listing |
| neuroblastoma | | FMH25 | Imperial Cancer Research Technology MaB Listing |
| renal cancer & glioblastomas | p155 | 6.1 | Loop et al., 1981 |
| Bladder & laryngeal cancers | "Ca Antigen"350-390 kD | CA1 | Ashall et al., 1982 |
| neuroblastoma | GD2 | 3F8 | Cheung et al., 1986 |
| Prostate | gp48 48 kD GP | $4F_7/7A_{10}$ | Bhattacharya et al., 1984 |
| Prostate | 60 kD GP | $2C_8/2F_7$ | Bhattacharya et al., 1985 |
| Thyroid | 'CEA' 180 kD GP | CEA 11-H5 | Wagener et al., 1984 | abbreviations: Abs, antibodies; Ags, antigens; EGF, epidermal growth factor; GI, gastrointestinal; GICA, gastrointestinal-associated antigen; GP, glycoprotein; GY, gynecological; HMFG, human milk fat globule; Kd, kilodaltons; Mabs, monoclonal antibodies; $M_r$, molecular weight; NS, not specified; PLAP, placental alkaline phosphatase; TAG, tumor-associated glycoprotein; CEA, carcinoembryonic antigen. Note: the CA 199 Ag (GICA) is sialosylfucosyllactotetraosylceramide, also termed sialylated Lewis pentaglycosyl ceramide or sialyated lacto N-fucopentaose II; p97 Ags are believed to be chondroitin sulphate proteoglycan; antigens reactive with Mab 9.2.27 are believed to be sialylated glycoproteins associated with chondroitin sulphate proteoglycan; unless specified, GY can include cancers of the cervix, endocervix, endometrium, fallopian tube, ovary, vagina or mixed Mullerian tumor; unless specified GI can include cancers of the liver, small intestine, spleen, pancreas, stomach and oesophagus.

In one embodiment, the Selective Binding Domain is an inhibitor of prostate specific membrane antigen (PSMA) or folate glutamate hydrolase. Prostate specific membrane antigen (PSMA) is a signal marker for prostate that is overexpressed in prostate carcinoma, especially in advanced tumors. The PSMA protein is a glutamyl preferring carboxypeptidase that can release glutamate with either gamma or alpha linkages. New data indicates that PSMA is selectively expressed and apparently present on the endothelial surface of tumor microvasculature.

According to the invention, endothelial-like tumor cells that express PSMA can undergo a novel differentiation process termed "vasculogenic mimicry." Such vasculogenic mimicry occurs when such endothelial-like tumor cells form vessels within solid prostate tumors. These tumor vessels connect with the normal circulatory system and may provide blood nutrients and oxygen to the interior of solid tumors. Therefore, according to the invention, proteins that are expressed on endothelial-like solid tumor cells can serve as recognition sites or targets for the Selective Tissue Vascular Thrombogens of the invention.

PSMA is one such target for the Selective Tissue Vascular Thrombogens of the invention. According to the invention, any molecule that can bind to PSMA can be used as a Selective Binding Domain for a Selective Tissue Vascular Thrombogen that can be used to treat prostate tumors. Selective Binding Domains that can be used to target PSMA include PSMA inhibitors and modified substrates, for example, the dipeptide Asp-β, linked-Glu (DβE), and N-succinyl-glutamic acid. The Asp-β linked-Glu dipeptide is a suicidal inhibitor of the PSMA protease. According to the invention, a Asp-β linked-Glu-biotin:avidin-Tissue Factor:VIIa thrombogen complex induces tumor infarction in PSMA expressing prostate tumors without harming the animal.

In another embodiment, inhibitors of N-Acetylated α-Linked Acidic Dipeptidase (NAALADase) are used as the Selective Binding Domain to deliver the thrombogen to the selected target. Examples of such NAALADase inhibitors include phosphonate moieties, such as 2-(phosphonomethyl) pentanedioic acid. Further examples include the following:
2-Methylhydroxyphosphinyl oxypentanedioic acid;
2-Ethylhydroxyphosphinyl oxypentanedioic acid;
2-Propylhydroxyphosphinyl oxypentanedioic acid;
2-Butylhydroxyphosphinyl oxypentanedioic acid;
2-Phenylhydroxyphosphinyl oxypentanedioic acid;
2-(Phenylmethyl)hydroxyphosphinyl oxypentanedioic acid;
(2-Phenylethyl)methyl)hydroxyphosphinyl oxypentanedioic acid.

Another group of NAALADase enzyme inhibitors that can be used to deliver the present thrombogen contain phosphoramidates and related groups, for example:
Methylhydroxyphosphinyl glutamic acid;
Ethylhydroxyphosphinyl glutamic acid;
Propylhydroxyphosphinyl glutamic acid;
Butylhydroxyphosphinyl glutamic acid;
Phenylhydroxyphosphinyl glutamic acid;
(Phenylmethyl)hydroxyphosphinyl glutamic acid;
((2-Phenylethyl)methyl)hydroxyphosphinyl glutamic acid; and
Methyl-N->Phenylhydroxyphosphinyl glutamic acid.

Another group of NAALADase enzyme inhibitors that can be used to deliver thrombogens have a phosphinic acid group. Such inhibitors contain any one of the following moieties:
2-methylhydroxyphosphinyl methylpentanedioic acid;
2-ethylhydroxyphosphinyl methylpentanedioic acid;
2-propylhydroxyphosphinyl methylpentanedioic acid;
2-butylhydroxyphosphinyl methylpentanedioic acid;
2-cylobexylhydroxyphosphinyl methylpentanedioic acid;
2-phenylhydroxyphosphinyl methylpentanedioic acid;
2-(phenylmethyl) hydroxyphosphinyl methylpentanedioic acid;
2-((2-phenylethyl)methyl)hydroxyphosphinyl methylpentanedioic acid;
2-((3-phenylpropyl)methyl)hydroxyphosphinyl methylpentanedioic acid;
2-((3-phenylbutyl)methyl)hydroxyphosphinyl methylpentanedioic acid;
2-((2-phenylbutyl)methyl)hydroxyphosphinyl methylpentanedioic acid;
2-(4-phenylbutyl) hydroxyphosphinyl methylpentanedioic acid;
2-(aminomethyl) hydroxyphosphinyl methylpentanedioic acid.

Certain sulfoxide and sulfone derivatives also act as inhibitors of NAALADase enzymes and can be used to deliver the thrombogen of the invention. Such inhibitors contain any one of the following moieties:
2-(sulfinyl)methylpentanedioic acid;
2-(methylsulfinyl)methylpentanedioic acid;
2-(ethylsulfinyl)methylpentanedioic acid;
2-(propylsulfinyl)methylpentanedioic acid;
2-(butylsulfinyl)methylpentanedioic acid;
2-(phenylsulfinyl methylpentanedioic acid;
2-(2-phenylethyl)sulfinyl methylpentanedioic acid;
2-(3-phenylpropyl)sulfinyl methylpentanedioic acid;
2-(4-pyridyl)sulfinyl methylpentanedioic acid; and
2-(benzylsulfinyl)methylpentanedioic acid.
2-(sulfonyl)methylpentanedioic acid;
2-(methylsulfonyl)methylpentanedioic acid;
2-(ethylsulfonyl)methylpentanedioic acid;
2-(propylsulfonyl)methylpentanedioic acid;
2-(butylsulfonyl)methylpentanedioic acid;
2-(phenylsulfonyl)methylpentanedioic acid;
2-(2-phenylethyl)sulfonyl methylpentanedioic acid;
2-(3-phenylpropyl)sulfonyl methylpentanedioic acid;
2-(4-pyridyl)sulfonylmethylpentanedioic acid; and
2-(N-hydroxy)carbamoyl methylpentanedioic acid;

Yet another group of NAALADase inhibitors contain hydroxamic acid moieties. Examples of such moieties include the following.
2-(N-hydroxy-N-methyl)carbamoyl methylpentanedioic acid;
2-(N-butyl-N-hydroxy)carbamoyl methylpentanedioic acid;
2-(N-benzyl-N-hydroxy)carbamoyl methylpentanedioic acid;
2-(N-hydroxy-N-phenyl)carbamoyl methylpentanedioic acid;
2-(N-hydroxy-N-2-phenylethyl) carbamoylmethylpentanedioic acid;
2-(N-ethyl-N-hydroxy)carbamoyl methylpentanedioic acid;
2-(N-hydroxy-N-propyl)carbamoylmethylpentanedioic acid;
2-(N-hydroxy-N-3-phenylpropyl)carbamoyl methylpentanedioic acid; and
2-(N-hydroxy-N-4-pyridyl)carbamoyl methylpentanedioic acid
2-(benzylsulfonyl)methylpentanedioic acid.

One of skill in the art can readily prepare and integrate these types of moieties and inhibitor molecules into the Selective Tissue Vascular Thrombogens of the invention with one or more Tissue Factor polypeptides using available procedures. See, e.g., U.S. Pat. Nos. 5,795,877; 5,863,536; 5,902,817; 5,968,915; and 5,880,112.

Another Selective Binding domain contemplated by the invention is a peptide or polypeptide containing an Arg-Gly-Asp (RGD) tripeptide sequence. Any RGD-containing Selective Binding Domain that can bind to an integrin is contemplated by the invention. A number of integrins exist and, according to the invention, such integrin subtypes will all support the coagulative activity of a Tissue Factor:RGD Selective Binding Domain construct. For example, VLA is the major integrin expressed on the CHO cell surface, and the Alpha V beta III integrins are reported to be expressed on angiogenic tumor vessels. Inhibition of alpha V beta III integrin with LM609 antibody was shown to inhibit angiogenesis and tumor growth (Brooks, Montgomery et al. 1994). According to the invention, RGD Selective Binding Domain: Tissue Factor constructs can be used to occlude blood vessels within integrin-expressing tumors.

One type of RGD bearing Selective Binding Domain useful in the invention can be derived from the extra-cellular matrix glycoprotein fibronectin. Fibronectin contains a number of domains that mediate its association with integrin molecules. One region of fibronectin that mediates its interaction with integrin is the Central Cell Binding Domain (CCBD). This region contains a number of homologous repeating polypeptide modules termed Fibronectin Type III Repeats, each being about 90 amino acids residues long. An RGD sequence, located in the tenth Fibronectin type III repeat, is a key recognition site for several different integrins, including the Alpha5beta 1 integrin family.

According to the invention, synthetic peptides having the RGD sequence and the Fibronectin type III repeat domains 8-11 are a useful Selective Binding Domains that can successfully confer coagulative properties to the surface of the cells that are otherwise inactive. Alternatively, one may use only the fibronectin 10$^{th}$ type III repeat domain.

In one embodiment, the Selective Binding Domain is selected from human fibronectin, having, for example, SEQ ID NO:8.

```
   1 MVQPQSPVAV SQSKPGCYDN GKHYQINQQW ERTYLGNALV
  41 CTCYGGSRGF NCESKPEAEE TCFDKYTGNT YRVGDTYERP
  81 KDSMIWDCTC IGAGRGRISC TIANRCHEGG QSYKIGDTWR
 121 RPHETGGYML ECVCLGNGKG EWTCKPIAEK CFDHAAGTSY
 161 VVGETWEKPY QGWMMVDCTC LGEGSGRITC TSRNRCNDQD
 201 TRTSYRIGDT WSKKDNRGNL LQCICTGNGR GEWKCERHTS
 241 VQTTSSGSGP FTDVRAAVYQ PQPHPQPPPY GHCVTDSGVV
 281 YSVGMQWLKT QGNKQMLCTC LGNGVSCQET AVTQTYGGNS
 321 NGEPCVLPFT YNGRTFYSCT TEGRQDGHLW CSTTSNYEQD
 361 QKYSFCTDHT VLVQTRGGNS NGALCHFPFL YNNHNYTDCT
 401 SEGRRDNMKW CGTTQNYDAD QKFGFCPMAA HEEICTTNEG
 441 VMYRIGDQWD KQHDMGHMMR CTCVGNGRGE WTCIAYSQLR
 481 DQCIVDDITY NVNDTFHKRH EEGHMLNCTC FGQGRGRWKC
 521 DPVDQCQDSE TGTFYQIGDS WEKYVHGVRY QCYCYGRGIG
 561 EWHCQPLQTY PSSSGPVEVF ITETPSQPNS HPIQWNAPQP
 601 SHISKYILRW RPKNSVGRWK EATIPGHLNS YTIKGLKPGV
 641 VYEGQLISIQ QYGHQEVTRF DFTTTSTSTP VTSNTVTGET
 681 TPFSPLVATS ESVTEITASS FVVSWVSASD TVSGFRVEYE
 721 LSEEGDEPQY LDLPSTATSV NIPDLLPGRK YIVNVYQISE
 761 DGEQSLILST SQTTAPDAPP DTTVDQVDDT SIVVRWSRPQ
 801 APITGYRIVY SPSVEGSSTE LNLPETANSV TLSDLQPGVQ
 841 YNITIYAVEE NQESTPVVIQ QETTGTPRSD TVPSPRDLQF
 881 VEVTDVKVTI MWTPPESAVT GYRVDVIPVN LPGEHGQRLP
 921 ISRNTFAEVT GLSPGVTYYF KVFAVSHGRE SKPLTAQQTT
 961 KLDAPTNLQF VNETDSTVLV RWTPPRAQIT GYRLTVGLTR
1001 RGQPRQYNVG PSVSKYPLRN LQPASEYTVS LVAIKGNQES
1041 PKATGVFTTL QPGSSIPPYN TEVTETTIVI TWTPAPRIGF
1081 KLGVRPSQGG EAPREVTSDS GSIVVSGLTP GVEYVYTIQV
1121 LRDGQERDAP IVNKVVTPLS PPTNLHLEAN PDTGVLTVSW
1161 ERSTTPDITG YRITTTPTNG QQGNSLEEVV HADQSSCTFD
1201 NLSPGLEYNV SVYTVKDDKE SVPISDTIIP AVPPPTDLRF
1241 TNIGPDTMRV TWAPPPSIDL TNFLVRYSPV KNEEDVAELS
1281 ISPSDNAVVL TNLLPGTEYV VSVSSVYEQH ESTPLRGRQK
1321 TGLDSPTGID FSDTTANSFT VHWIAPRATI TGYRIRHHPE
```

```
                   -continued
1361 HFSGRPREDR VPHSRNSITL TNLTPGTEYV VSIVALNGRE
1401 ESPLLIGQQS TVSDVPRDLE VVAATPTSLL ISWDAPAVTV
1441 RYYRITYGET GGNSPVQEFT VPGSKSTATI SGLKPGVDYT
1481 ITVYAVTGRG DSPASSKPIS INYRTEIDKP SQMQVTDVQD
1521 NSISVKWLPS SSPVTGYRVT TTPKNGPGPT KTKTAGPDQT
1561 EMTIEGLQPT VEYVVSVYAQ NPSGESQPLV QTAVTNIDRP
1601 KGLAFTDVDV DSIKIAWESP QGQVSRYRVT YSSPEDGIHE
1641 LFPAPDGEED TAELQGLRPG SEYTVSVVAL HDDMESQPLI
1681 GTQSTAIPAP TDLKFTQVTP TSLSAQWTPP NVQLTGYRVR
1721 VTPKEKTGPM KEINLAPDSS SVVVSGLMVA TKYEVSVYAL
1761 KDTLTSRPAQ GVVTTLENVS PPRRARVTDA TETTITISWR
1801 TKTETITGFQ VDAVPANGQT PIQRTIKPDV RSYTITGLQP
1841 GTDYKIYLYT LNDNARSSPV VIDASTAIDA PSNLRFLATT
1881 PNSLLVSWQP PRARITGYII KYEKPGSPPR EVVPRPRPGV
1921 TEATITGLEP GTEYTTYVIA LKNNQKSEPL IGRKKTDELP
1961 QLVTLPHPNL HGPEILDVPS TVQKTPFVTH PGYDTGNGIQ
2001 LPGTSGQQPS VGQQNIFEEH GFRRTTPPTT ATPIRHRPRP
2041 YPPNVGQEAL SQTTISWAPF QDTSEYIISC HPVGTDEEPL
2081 QFRVPGTSTS ATLTGLTRGA TYNVIVEALK DQQRHKVREE
2121 VVTVGNSVNE GLNQPTDDSC FDPYTVSHYA VGDEWERMSE
2161 SGFKLLCQCL GFGSGHFRCD SSRWCHDNGV NYKIGEKWDR
2201 QGENGQMMSC TCLGNGKGEF KCDPHEATCY DDGKTYHVGE
2241 QWQKEYLGAI CSCTCFGGQR GWRCDNCRRP GGEPSPEGTT
2281 GQSYNQYSQR YHQRTNTNVN CPIECFMPLD VQADREDSRE
```

The selected Selective Binding Domain can be fused, attached or associated with a Tissue Factor polypeptide to generate The Selective Tissue Vascular Thrombogen by any available procedure. For example, the Tissue Factor extracellular domain (e.g., SEQ ID NO:3, 4, 5 or 6) can be made by known procedures. Such a Tissue Factor polypeptide can be modified to contain a convenient attachment site or moiety at any location that does not substantially interfere with initiation of thrombosis. One convenient attachment site is the N-terminus of the Tissue Factor polypeptide.

In one embodiment, the Selective Binding Domain is fused to the Tissue Factor polypeptide by use of recombinant technology. One of skill in the art can readily employ known cloning procedures to fuse a nucleic acid encoding the desired Selective Binding Domain to a nucleic acid encoding a Tissue Factor polypeptide. See, e.g., Sambrook et al., Molecular Cloning, A Laboratory Manual, Cold Spring Harbor Laboratory, N.Y., 1989; Sambrook et al., Molecular Cloning, A Laboratory Manual, Cold Spring Harbor Laboratory, N.Y., 2001.

The selected Selective Binding Domain can also be attached or associated to a Tissue Factor polypeptide by formation of covalent or non-covalent bonds. Such attachment or association can be done directly or indirectly to the N-terminus, or other convenient site, on the Tissue Factor polypeptide. For example, an indirect attachment or association can be achieved via a convenient reactive moiety or through a flexible linker to facilitate formation of the Selective Tissue Vascular Thrombogen and/or to promote proper association between the Tissue Factor polypeptide and the cellular membrane to which it will associate. Use of such a linker to achieve optimal integration and functioning of the domains within the Selective Tissue Vascular Thrombogen is at the discretion of one of skill in the art, who can readily ascertain whether membrane association by the Tissue Factor-Selective Binding Domain protein is improved by use of a linker.

By way of example, attachment of a Selective Binding Domain can be at the N-terminus of a Tissue Factor polypeptide that has been modified to contain a reactive moiety, for example a cysteine, at the N-terminus. A cysteine can be attached to the N-terminus of Tissue Factor, for example, by attaching a peptide containing poly His tag and a processing protease (FXa) cleavage site followed by a cysteine (MXXX-HHHHHH-XXXX-IEGR-C, SEQ ID NO:18) to the N-terminus of Tissue Factor (SEQ ID NO:6). Factor Xa digestion cleaves off the majority of this peptide but leaves a cysteine at the N-terminus of the Tissue Factor polypeptide. This Cys-Tissue Factor polypeptide can then be attached to a desired Selective Binding Domain by available protein ligation reactions (see, e.g., Erlanson, Chytil et al. 1996).

A Selective Binding Domain comprising a compound, peptide or polypeptide can therefore be linked to the N-terminus of the Tissue Factor extracellular domain (SEQ ID NO:3, 4, 5 or 6) through a disulfide bond. Alternatively, such a Selective Binding Domain can be linked to a lysine containing linker and then attached to a Cys-Tissue Factor polypeptide by a thiazolidine ring formed by reaction the cysteine and the lysine (see, e.g., Zhang, Torgerson et al. 1998). One such lysine containing linker is KSGGG (SEQ ID NO:19). In one embodiment, the D-β-E dipeptide is attached to the C-terminal glycine of SEQ ID NO:19 and this seven-amino acid peptide is linked to an N-terminal cysteine of a Tissue Factor polypeptide via a thiazolidine ring formed by reaction the cysteine and the lysine.

In another embodiment, a biotin and streptavidin can be used to associate a Selective Binding Domain with a Tissue Factor polypeptide. Because the binding of biotin to streptavidin is so stable, there is no need for covalent linkage. Instead, biotin can be linked to a Selective Binding Domain and Streptavidin can be linked to a selected Tissue Factor polypeptide. The two preparations can be incubated together to form a Selective Binding Domain-biotin:streptavidin-Tissue Factor complex that is a functional Selective Tissue Vascular Thrombogen. Of course, one of skill in the art can, alternatively, link streptavidin to a Selective Binding Domain and biotin to a Tissue Factor polypeptide to achieve a similar complex.

One such biotin:streptavidin Selective Tissue Vascular Thrombogen was made and tested for thrombogenic activity. This complex had a biotinylated PSMA inhibitor, Asp-β-linked-L-Glutamate (DβE ), as a Selective Binding Domain. A streptavidin moiety was N-terminally attached to the extracellular domain of Tissue Factor (SEQ ID NO:5). After incubation of the two domains a DβE-biotin:streptavidin-Tissue Factor complex was formed. Injection of this complex into animals leads to extensive thrombosis and necrosis of tumors within the animals.

Before use as a therapeutic agent, the Selective Tissue Vascular Thrombogens can be mixed with Factor VIIa under conditions permitting formation of the functional Selective Tissue Vascular Thrombogen:Factor VIIa thrombogenic complex.

Specific Selective Tissue Vascular Thrombogens

In one embodiment, the Selective Tissue Vascular Thrombogen has a Selective Binding Domain that is an integrin binding site comprising the Fibronectin type III repeat domains 8-11 from human fibronectin. One example of this type of Selective Tissue Vascular Thrombogen has SEQ ID NO:9:

```
  1  MRGSHHHHHH GSGSSTPPPT DLRFTNIGPD TMRVTWAPPP
 41  SIDLTNFLVR YSPVKNEEDV AELSISPSDN AVVLTNLLPG
 81  TEYVVSVSSV YEQHESTPLR GRQKTGLDSP TGIDFSDITA
121  NSFTVHWIAP RATITGYRIR HHPEHFSGRP REDRVPHSRN
161  SITLTNLTPG TEYVVSIVAL NGREESPLLI GQQSTVSDVP
201  RDLEVVAATP TSLLISWDAP AVTVRYYRIT YGETGGNSPV
241  QEFTVPGSKS TATISGLKPG VDYTITVYAV TGRGDSPASS
281  KPISINYRTE IDKPSQMQVT DVQDNSISVK WLPSSSPVTG
321  YRVTTTPKNG PGPTKTKTAG PDQTEMTIEG LQPTVEYVVS
361  VYAQNPSGES QPLVQTAVTS SSGTTNTVAA YNLTWKSTNF
401  KTILEWEPKP VNQVYTVQIS TKSGDWKSKC FYTTDTECDL
441  TDEIVKDVKQ TYLARVFSYP AGNVESTGSA GEPLYENSPE
481  FTPYLETNLG QPTIQSFEQV GTKVNVTVED ERTLVRRNNT
521  FLSLRDVFGK DLIYTLYYWK SSSSGKKTAK TNTNEFLIDV
561  DKCENYCFSV QAVIPSRTVN RKSTDSPVEC MGQEKGEFR
```

In another embodiment, the Selective Tissue Vascular Thrombogen has a Selective Binding Domain that is an integrin binding site from the Fibronectin $10^{th}$ type III repeat domain of human fibronectin fused to an extracellular domain of Tissue Factor. An example of this type of Selective Tissue Vascular Thrombogen has SEQ ID NO:10:

```
  1  MRGSHHHHHH GSGSSTVSDV PRDLEVVAAT PTSLLISWDA
 41  PAVTVRYYRI TYGETGGNSP VQEFTVPGSK STATISGLKP
 81  GVDYTITVYA VTGRGDSPAS SKPISINYRT SSSGTTNTVA
121  AYNLTWKSTN FKTILEWEPK PVNQVYTVQI STKSGDWKSK
161  CFYTTDTECD LTDEIVKDVK QTYLARVFSY PAGNVESTGS
201  AGEPLYENSP EFTPYLETNL GQPTIQSFEQ VGTKVNVTVE
241  DERTLVRRNN TFLSLRDVFG KDLIYTLYYW KSSSSGKKTA
281  KTNTNEFLID VDKGENYCFS VQAVIPSRTV NRKSTDSPVE
321  CMGQEKGEFR
```

Methods of Use

The invention provides a method of treating a solid tumor in an animal that includes administering a therapeutically effective amount of a Selective Tissue Vascular Thrombogen of the invention to the animal. Such a Selective Tissue Vascular Thrombogen has at least one Selective Binding Domain associated with one or more thrombogenically active Tissue Factor polypeptides. Additional domains can be added to achieve optimized localization and/or thrombogenic activity. As described above, the Selective Binding Domain can selectively bind to a blood channel within a tumor and the Tissue Factor Domain can induce localized thrombin production and thrombosis within the blood channel. According to the invention, such thrombosis results in tumor infarction and necrosis. In a preferred embodiment, the Selective Tissue Vascular Thrombogen, and compositions of the invention are administered intravenously in solution or, alternatively, in liposomes.

In another embodiment, the invention provides methods of inhibiting tumor vascularization by administering PSMA inhibitors. According to the invention, PSMA can influence vascularization of prostate tumors. Moreover, inhibitors of PSMA activity can exert a cytotoxic effect on prostate tumor cells that express PSMA. PSMA inhibitors can also have a synergistically beneficial effect when administered with other chemotherapeutic agents and with the Selective Tissue Vascular Thrombogens of the invention.

The balance between gamma-glutamate hydrolase and synthase activity is known to effect cancer cell susceptibility to anti-folate chemotherapy. Over-expression of gamma glutamyl hydroxylase activity, which is an activity of PSMA, can promote to cancer cell resistance to anti-folate drugs (Rhee, Wang et al. 1993). Methotrexate is the most widely used anti-folate for clinical cancer chemotherapy; its own retention in cell is also dependent on polyglutamation. PSMA can remove glutamate from folic acid and other cellular components. Prostate cancers are notoriously resistant to chemotherapy, possibly because PSMA is over-expressed in prostate tumor cells.

However, according to the invention, PSMA inhibitors have a synergistic effect on reducing cancer cell growth when combined with anti-folate chemotherapeutic agents and PSMA inhibition can enhance the sensitivity of prostate cancer to anti-folate drugs. Accordingly, PSMA inhibitors can be administered with other chemotherapeutic agent such as an anti-folate drug used to treat prostate cancer. Such anti-folate drugs include those listed herein (Table 3). PSMA inhibitors include any inhibitor available to one of skill in the art that inhibits the activity of PSMA, for example, any inhibitor of the gamma glutamyl hydrolase activity of PSMA. PSMA inhibitors contemplated by the invention include listed herein, especially, the Asp-β linked-Glu dipeptide, N-succinyl-glutamic acid, quisqalic acid (Sigma), 2-(phosphonomethyl)pentanedioic acid and related compounds. Quisqalic acid is a non-competitive inhibitor of NAALADase activity with $K_i=1.9$ uM, and D-β-E is a competitive inhibitor with $K^i=0.7$ uM. PSMA enzymatic activity can substantially reduced with such inhibitors.

Any solid tumor can be treated by the present methods. For example, the solid tumor can be any of the tumors or carcinomas listed herein. Examples of tumors and carcinomas contemplated include lung, breast, ovary, stomach, pancreas, larynx, esophagus, testes, liver, parotid, biliary tract, colon, rectum, cervix, uterus, endometrial, kidney, bladder, prostate, thyroid, squamous cell carcinoma, adenocarcinoma, small cell carcinoma, melanoma, glioma, or neuroblastoma tumor. In one embodiment the tumor is a prostate tumor.

Any chemotherapeutic agent known to one of skill in the art can also be administered in conjunction with the PSMA inhibitors and Selective Tissue Vascular Thrombogens of the invention. According to the invention, combinations of therapeutic agents that include the present Selective Tissue Vascular Thrombogens can act synergistically to provide enhanced tumor necrosis. Chemotherapeutic agents that can be co-administered with these Thrombogens and inhibitors of the invention include, for example, methotrexate, doxorubicin, paclitaxil, carboplatin and the like. Further examples of chemotherapeutic agent that can be administered with the Selective Tissue Vascular Thrombogens of the invention are provided in Table 3.

TABLE 3

Chemotherapeutic Agents

| Chemotherapeutic Agent | Median Dosage |
|---|---|
| Aldesleukin | 22 million units |
| Asparaginase | 10,000 units |
| Bleomycin Sulfate | 15 units |
| Carboplatin | 50-450 mg |
| Carmustine | 100 mg |
| Cisplatin | 10-50 mg |
| Cladribine | 10 mg |
| Cyclophosphamide (lyophulized) | 100 mg-2 gm |
| Cyclophosphamide (non-lyophilized) | 100 mg-2 gm |
| Cytarabine (lyophilized powder) | 100 mg-2 gm |
| Dacarbazine | 100 mg-200 mg |
| Dactinomycin | 0.5 mg |
| Daunorubicin | 20 mg |
| Diethyistilbestrol | 250 mg |
| Doxorubicin | 10-150 mg |
| Epoetin Alfa | 2,000-10,000 units |
| Etidronate | 300 mg |
| Etoposide | 100 mg |
| Filgrastim | 300-480 mcgm |
| Floxuridine | 500 mg |
| Fludarabine Phosphate | 50 mg |
| Fluorouracil | 500 mg-5 gm |
| Goserelin | 3.6 mg |
| Granisetron Hydrochloride | 1 mg |
| Idarubicin | 5-10 mg |
| Ifosfamide | 1-3 gm |
| Immune Globulin | 500 mg-10 gm |
| Interferon Alpha-2a | 3-36 million units |
| Interferon Alpha-2b | 3-50 million units |
| Leucovorin Calcium | 50-350 mg |
| Leuprolide | 3.75-7.5 mg |
| Levamisole | 50 mg |
| Mechiorethamine | 10 mg |
| Medroxyprogesterone | 1 gm |
| Melphalan | 50 gm |
| Methotrexate | 20 mg-1 gm |
| Mitomycin | 5-40 mg |
| Mitoxantrone | 20-30 mg |
| Octreotide | 1,000-5,000 mcgm |
| Ondansetron Hydrochloride | 40 mg |
| Paclitaxel | 30 mg |
| Pamidronate Disodium | 30-*90 mg |
| Pegaspargase | 750 units |
| Plicamycin | 2,500 mcgm |
| Sargramostim | 250-500 mcgm |
| Streptozocin | 1 gm |
| Thiotepa | 15 mg |
| Teniposide | 50 mg |
| Vinblastine | 10 mg |
| Vincristine | 1-5 mg |

The activity and pharmacological effects of the Selective Tissue Vascular Thrombogens and inhibitors of the invention can be characterized using any method available to one of skill in the art. In one embodiment, these Selective Tissue Vascular Thrombogens and inhibitors can be tested in vivo using prostate cancer model animals, for example, in Lucap58, Mat Lu and LnCaP tumors. Therapeutic regimens and dosages can also be optimized by observing the degree of in vivo infarction of Lucap58, Mat Lu and LnCaP tumors after administration of compositions contained the present Selective Tissue Vascular Thrombogens and/or inhibitors. Inhibition of tumor growth can also be used to determine $ED_{50}$ (median effective dose) of the Selective Tissue Vascular Thrombogens and PSMA inhibitors. The activity and pharmacological effects of the Selective Tissue Vascular Thrombogens and inhibitors of the invention can also be characterized in vitro using tumors and tumor cells in culture.

For example, compositions containing inhibitors and/or Selective Tissue Vascular Thrombogens can be analyzed for efficiency of induction of apoptosis, for example, by measuring apoptosis in prostate cancer cells and endothelial cells using a TUNEL assay (Boehringer Mannheim). The efficacy of the inhibitors can be determined using a calorimetric cell proliferation assay (Boehringer Mannheim), which is based on the cleavage of tetrazolium salt WST-1 by mitochondrial dehydrogenases in viable LnCap cells and other PSMA positive cells. PSMA inhibitors can further be characterized in vitro by enzymatic assay of PSMA gamma glutamyl hydrolase activity in the presence and absence of selected PSMA inhibitors. For example, the ability of an inhibitor to inhibit PSMA activity can be assessed using a γ-glutamyl hydrolase assay with 4-NH2-10CH$_3$ PteGlu$_5$ as a substrate (O'Connor, Rotundo et al. 1991; Wang, Rotundo et al. 1993). The Ki for inhibitors tested in this assay can be determined to serve as a reference point in determining the proper in vitro and in vivo dosages for that inhibitor.

Compositions

The Selective Tissue Vascular Thrombogens and inhibitors of the invention can be formulated as pharmaceutical compositions and administered to a mammalian host, such as a human patient in a variety of forms adapted to the chosen route of administration. Preferred routes for administration include, for example, intravenous and intraarterial routes.

Solutions of the active constructs and inhibitors or their salts can be prepared in water or saline, and optionally mixed with a nontoxic surfactant. Formulations for intravenous or intraarterial administration may include sterile aqueous solutions that may also contain buffers, liposomes, diluents and other suitable additives.

The pharmaceutical dosage forms suitable for injection or infusion can include sterile aqueous solutions or dispersions comprising the active ingredient that are adapted for administration by encapsulation in liposomes. In all cases, the ultimate dosage form must be sterile, fluid and stable under the conditions of manufacture and storage.

Sterile injectable solutions are prepared by incorporating the active constructs and inhibitors in the required amount in the appropriate solvent with various of the other ingredients enumerated above, as required, followed by filter sterilization.

Useful dosages of the constructs and inhibitors can be determined by comparing their in vitro activity, and in vivo activity in animal models. Methods for the extrapolation of effective dosages in mice, and other animals, to humans are known to the art; for example, see U.S. Pat. No. 4,938,949.

In general, a suitable dose will be in the range of from about 1 to about 2000 µg/kg, for example, from about 2.0 to about 1500 µg/kg of body weight per treatment. Preferred doses are in the range of about 3 to about 500 µg per kilogram body weight of the recipient per treatment, more preferably in the range of about 10 to about 300 µg/kg/treatment, most preferably in the range of about 20 to about 200 µg/kg/treatment.

The compound is conveniently administered in unit dosage form; for example, containing 5 to 1000 µg, conveniently 10 to 750 µg, most conveniently, 50 to 500 µg of active ingredient per unit dosage form.

Ideally, the active ingredient should be administered to achieve peak plasma concentrations of the active compound of from about 0.1 to about 10 nM, preferably, about 0.2 to 10 nM, most preferably, about 0.5 to about 5 nM. This may be achieved, for example, by the intravenous injection of a 0.05 to 25% solution of the active ingredient, optionally in saline. Desirable blood levels may be maintained by continuous infusion to provide about 0.01-10.0 µg/kg/hr or by intermittent infusions containing about 0.4-50 µg/kg of the active ingredient(s).

The desired dose may conveniently be presented in a single dose or as divided doses administered at appropriate intervals, for example, as two, three, four or more sub-doses per day. The sub-dose itself may be further divided, for example, into a number of discrete loosely spaced administrations; such as multiple intravenous doses. For example, it is desirable to administer the present compositions intravenously over an extended period, either by continuous infusion or in separate doses.

The ability of the constructs and inhibitors of the invention to act as thrombosis-inducing agents and tumor inhibitors may be determined using pharmacological models known to the art, or using tests described herein.

The invention will be further described by reference to the following detailed examples, which are given for illustration of the invention, and are not intended to be limiting thereof.

EXAMPLE 1

Activation of Coagulation by a Fibronectin-Tissue Factor Selective Tissue Vascular Thrombogen In this example, a recombinant protein that contains the N-terminal, extracellular domain of Tissue Factor was fused to the integrin-binding domain of fibronectin type III repeat domains 8-11 (SEQ ID NO:9). As illustrated below, this Selective Tissue Vascular Thrombogen conferred coagulation activity to integrin-expressing cells that otherwise did not activate the coagulation cascade. These data showed that the coagulation cascade is efficiently activated by creation of a four domain protein incorporating the extracellular domain of Tissue Factor and the fibronectin type III repeat domains 8-11. This Selective Tissue Vascular Thrombogen became associated with the cellular membrane carrying an integrin polypeptide. According to the invention, this paradigm can be used to engineer Tissue Factor-based thrombogens that are capable of occluding the blood vessels in a tissue-selective and/or cell-selective manner.

Construction of a Fibronectin-Tissue Factor Fusion Protein

Fibronectin nucleic acids were obtained by PCR amplification from marathon-ready cDNA library of human placental origin (Clontech, Inc.) using vent DNA polymerase (New England Biolabs) and the following primers:

5' CACCAACAACTTGCATCTGGAGGC 3' and (SEQ ID NO:11)

5' AACATTGGGTGGTGTCCACTGGGC 3'     (SEQ ID NO:12)

After 35 cycles of 1 min 94° C., 1 min 60° C., and 1 min 75° C., a 1445 bp fragment was purified. The 1445 fragment was used as template for another PCR amplification using the following primers:

5'   ACCATCACGGATCCGGGGTCGTCGACACCTCC TCCCACTGACCTGCGA 3' (SEQ ID NO:13, the "FN5a primer") and 5'   GGTACC   GGAGGAGCTCGTTACCTGCAGTCT-GAACCAGAGG 3' (SEQ ID NO:14). An 1131 bp fragment was obtained.

Tissue Factor nucleic acids were obtained by amplification from plasmid pTrcHisC-tTF (Stone et. al. 1995) using the following primers:

5' ACGAGCTCCTCCGGTACCACAAATACT-GTGGGCAGC 3' (SEQ ID NO:15 and 5' TCTGCGTTCT-GATTTAATCT 3' (SEQ ID NO:16, the "ptrc-seg" primer) to produce a 714 bp fragment.

The 1131 bp fragment and 714 bp fragment were combined and amplified as a fusion by PCR with the FN5a (SEQ ID NO:13) and ptrc-seq (SEQ ID NO: 16) primers to yield a 1827 bp fragment. This 1827 fragment was digested with HindIII, partially digested with BamHI, and the resulting 1753 bp fragment was ligated into the BamHI and HindIII sites of the vectorpTrcHisC (Invitrogen).

The resulting plasmid (FNTF2) encodes a protein fusion having SEQ ID NO:9 with a short His 6 Tag at the N-terminus, followed by fibronectin residues 1237 to 1603, a five-residue linker peptide, and Tissue Factor residues 3-218 at the C-terminus. Plasmid FNTF2 was transformed into the *E. coli* host BL21 (Stratagene) for protein production.

Proteins

The soluble extracellular domain of Tissue Factor (SEQ ID NO:5, termed TF3-218) was expressed in *E. coli*, then purified and refolded as previously described (Stone, Ruf et al. 1995). Factor X was purified from plasma (Fair, Plow et al. 1979), followed by immunoaffinity chromatography with immobilized monoclonal antibody F21-4.2 to reduce VII contamination (Dickinson, Kelly et al. 1996). Factor VII was affinity purified with a calcium dependent antibody to the Gla domain and followed by a Mono-Q ion-exchange chromatography that is associated with spontaneous activation of VII to VIIa.

The fibronectin-Tissue Factor (Fn-TF) fusion protein was expressed in *E. coli.* and refolded as follows. Briefly, BL21 bacteria were pelleted from cultures obtained 5 hours after IPTG induction. Bacteria were lysed using lysozyme digestion. Inclusion bodies were isolated using repeated sonication and centrifugation, then resuspended in Ni-NTA affinity purification buffer containing 6M guanidium chloride by sonication. The suspension was affinity purified using Ni-NTA column. Purified fractions were combined and DTT was added to final concentration of 50 mM at room temperature overnight to reduce disulfide bonds. Refolding of the protein was at 4° C. for 4 days in buffer containing 50 mM Tris, 2M urea and a combination of oxidized glutathione (0.5 mM) and reduced glutathione (2.5 mM). The refolded soluble fraction was collected and cleaned with a round of size-exclusion chromatography. The purified fusion protein appears as a homogenous band of approximately 96 kD on a silver staining gel (FIG. 2A) that reacts positively with anti-Tissue Factor antibodies (FIG. 2B) upon Western blot analysis.

The $LD_{50}$ (median lethal dose) of wild type soluble TF (SEQ ID NO:4) in 20 gm Balb/C mice is greater than 500 ug, while the $LD_{50}$ of the Fn-TF construct was about 8 ug.

Western Blot Analysis

The immunoreactivity of Tissue Factor was quantified by Western blot with an anti-human Tissue Factor (anti-huTF) antibody. Varying amounts of protein were electrophoretically separated and transferred to nitrocellulose membrane. Membranes were blocked with 5% non-fat milk in TBS. Primary antibody, at a concentration of 1 ug/ml, was incubated with the membranes for 1 hour at 37° C. An appropriate enzyme-linked secondary antibody was used to permit visualization of Tissue Factor bands using an enhanced chemiluminescence system (Amershan-Pharmacia). The intensity of the bands are quantified with scanning laser densitometry and compared to that of Tissue Factor standards of known concentration.

Amidolytic Assay of Bound Factor VIIa to Fn-TF or TF 1-218.

The catalytic activity of Factor VIIa bound to Fn-TF for a peptidyl substrate was analyzed by hydrolysis of chromozym t-Pa (Boehringer Mannheim) and compared with that of the soluble TF 1-218. Varying concentrations TF 1-218 or Fn-TF were incubated with Factor VIIa at a final concentration of 5nM in the presence of 5 mM $Ca^{++}$ at ambient temperature for 15 minutes. Chromozym t-PA was added to a concentration of 1 mM. The initial rate of hydrolysis was measured at 406 nm with a kinetic micro-titer plate reader for 1 minute.

Proteolytic Activity of Tissue Factor Constructs Toward Factor X

The proteolytic activities of both Fn-TF:Factor VIIa and TF 1-218:Factor VIIa complexes toward Factor X were determined by a functional assay (Schullek, Ruf et al. 1994) using Spectrozyme Factor Xa to assess Factor Xa generation. Briefly, varying concentrations of Fn-TF and TF1-218 were pre-incubated with Factor VIIa (75 nM) for 5 minutes at 37° C. in the presence of 5 mM $CaCl_2$. The reaction was initiated by addition of substrate Factor X (1.5 uM). After incubation for 10 minutes at 37° C., the reaction was terminated by adding EDTA to a concentration of 0.1M. The amount of Factor Xa generated was determined by measuring Factor Xa amidolytic activity using 50 mM of the chromogenic substrate Spectrozyme Fxa (American Diagnostica, Greenwich, Conn.). The rate of absorbance increase at 405 nM was measured in a kinetic micro-titer plate reader.

Coagulation Assay

Coagulation assays were performed using an established procedure with some modifications to include a step for binding Tissue Factor constructs to cells. Platelet depleted, citrated human plasma pooled from multiple donors was used for these experiments. Cells are dislodged with trypsin free cell dissociation buffer (Gibco), and washed twice with TBS. Cells were then counted with cytometer. Only cells with viability greater than 90% were used for the assay. Varying concentrations of thrombogen were incubated with $10^5$ cells in 100 ul TBS containing $Ca^{++}$ 10 mM and $Mg^{++}$ 5 mM for 15 minutes at 37° C. The assays were initiated by addition of 100 ul of pooled citrated plasma pre-warmed to 37° C. Clotting times were recorded as the interval between assay initiation and clot appearance.

Model Ternary Structure of Tissue Factor Constructs with Factor VIIa:Factor X

The model of ternary structure is based on the crystal structure of TF and Factor VIIA (Banner, D'Arcy et al. 1996). A Gla deleted Factor X structure (Padmanabhan et al. 1993) is the primary source for the Factor X model docked onto the Tissue Factor:VIIa complex using the InsightII program docking module.

Results

Production of a Fibronectin-Tissue Factor Fusion Protein

Two fibronectin-TF fusion proteins were created by recombinant methods described above to test the feasibility of localizing the thrombogenic activity of Tissue Factor selectively to the cell surface of integrin-expressing cells. The human fibronectin sequence that encodes typeII repeats 8 through 11 was amplified by PCR and fused to sequences encoding the extracellular segment of TF residues 3-218 to generate a protein with SEQ ID NO:9. Another fusion protein having SEQ ID NO:10 contained the fibronectin type III repeat domain 10 with the TF3-218 polypeptide. These proteins had similar properties and are referred to herein as Fn-TF or Tn-TF proteins. Like TF 1-218, when expressed in *E. coli*, the Fn-TF proteins accumulated in inclusion bodies. The Fn-TF proteins also behaved similarly to TF1-218 through refolding and purification. A silver staining gel of purified TF 1-218 and Fn-TF (SEQ ID NO:9) is shown in FIG. 2A, and a Western blot stained with anti-Tissue Factor antibodies is provided in FIG. 2B.

Amidolytic Activity of Factor VIIa Bound to Fn-TF

The activity of Fn-TF as cofactor for enhancement of Factor VIIa amidolytic activity is shown in FIG. 3. The binding of Factor VIIa to Tissue Factor involves extensive regions from both proteins encompassing a number of amino acid residues and forming a large interacting surface. The N-terminal portion of Tissue Factor is associated with the protease domain of Factor VIIa through residues Phe76, Tyr94, and Trp45. These interactions are considered important for allosteric activation of Factor VIIa activity.

Very little difference in amidolytic activity is discernable for Tissue Factor and Fn-TF except at high concentrations. This suggests the that affinity of Tissue Factor for Factor VIIa is not affected by the addition of fibronectin domains in the FN-TF fusion protein. Furthermore, the addition of fibronectin moiety to the N-terminus of Tissue Factor does not affect the subtle protein-protein interactions in the protease domain of Factor VIIa that are responsible for the allosteric enhancement of Factor VIIa amidolytic activity.

Proteolytic Activity of Fn-TF:Factor VIIa Toward Factor X

The effect of the fused docking structure on the proteolytic activity of TF:VIIa was studied by a linked functional assay (Schullek, Ruf et al. 1994). Varying concentrations of Fn-TF or TF1-218 were allowed to bind to 10 pM Factor VIIa for 5 minutes. To measure the proteolytic activity of the resulting TF:Factor VIIa or FN-TF:Factor VIIa complexes, Factor X was added to a concentration of 100 nM and the mixture was incubated for 10 minutes at 37 ° C. The reaction was stopped by addition of 50 mM EDTA and the amount of Factor Xa generated was determined by measuring the Factor Xa amidolytic activity in the assay mixture using spetrozyme FXa as described above.

Figure 4:
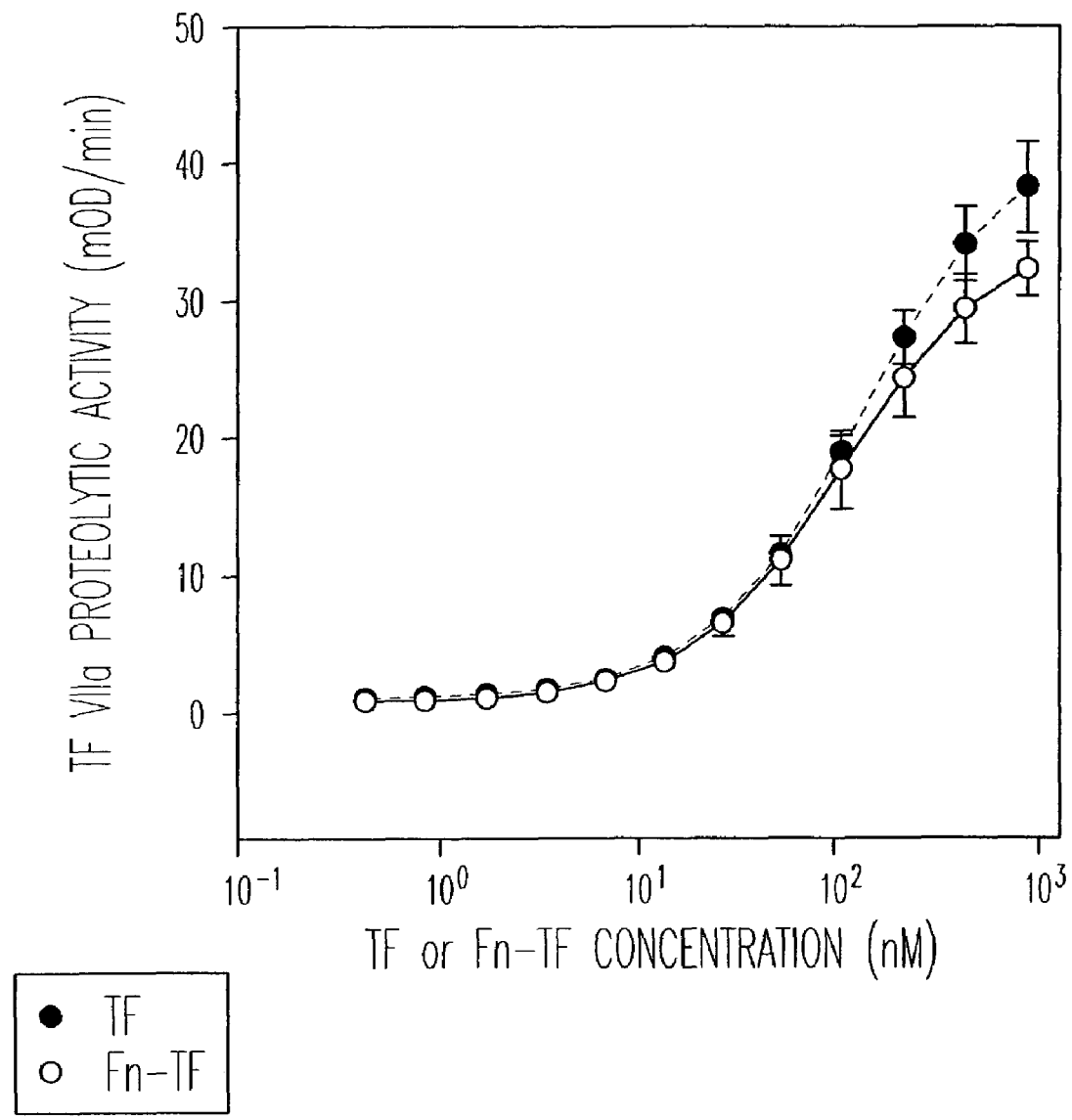

FIG. 4 shows the proteolytic activity of both soluble Fn-TF:Factor VIIa and Tissue Factor:Factor VIIa complexes toward Factor X. The increasing concentration of Fn-TF led to increased proteolytic activity similar to the curve obtained with TF1-218. These data suggest that the fused docking structure does not interfere with the recognition of Factor X by Fn-TF:Factor VIIa complex. Residues K165 and K166 in Tissue Factor are thought to be involved in binding to Factor X. When these residue are changed to alanine, there is no effect on the amidolytic activity of TF:VIIa activity, but there is a noted change in its proteolytic activity, thus indicating these residue are important in orienting the Factor X to allow the most efficient processing of the factor. The proteolytic activity of the protease complex is greatly enhanced when the Tissue Factor:Factor VIIa complex is properly docked onto an anionic lipid surface. This increase in activity may be explained by the interaction of the anionic lipid surface with the Gla domain of Factor VIIa bound to Tissue Factor, which will physically align the complex with substrate Factor X. The interaction of the Gla domain of both Factor VIIa and Factor X with phospholipids properly orients Factor X in relation to Factor VIIa and Tissue Factor. Proper orientation of the various proteins increases the recognition of Factor X by the Tissue Factor:Factor VIIa complex and promotes the activation of Factor X to Factor Xa.

Binding of Fn-TF to Integrin-Expressing CHO Cells

The beta-1 family (VLA) of integrins is widely distributed on the CHO cells. No endogenous Tissue Factor expression in CHO K1 cells was detected by Western Blot analysis or by the coagulation assay (data not shown). Hence, CHO K1 cells are an ideal system to study the docking of Fn-TF to integrin.

The binding of the Fn-TF protein to the integrin on CHO cells was monitored through direct incubation of varying concentrations of recombinant Fn-TF with $10^5$ CHO K1 cells in TBS, 10 mM $CaCl_2$, 5 mM $MgSO_4$. The bound and unbound proteins were separated by centrifugation, and the bound Tissue Factor immunoreactivity was detected by Western blot. The amount of Tissue Factor bound was quantified by comparing the intensity of resulting bands on the membrane to that of a standard curve of Tissue Factor protein of known concentration using a densitometer.

Figure 5:
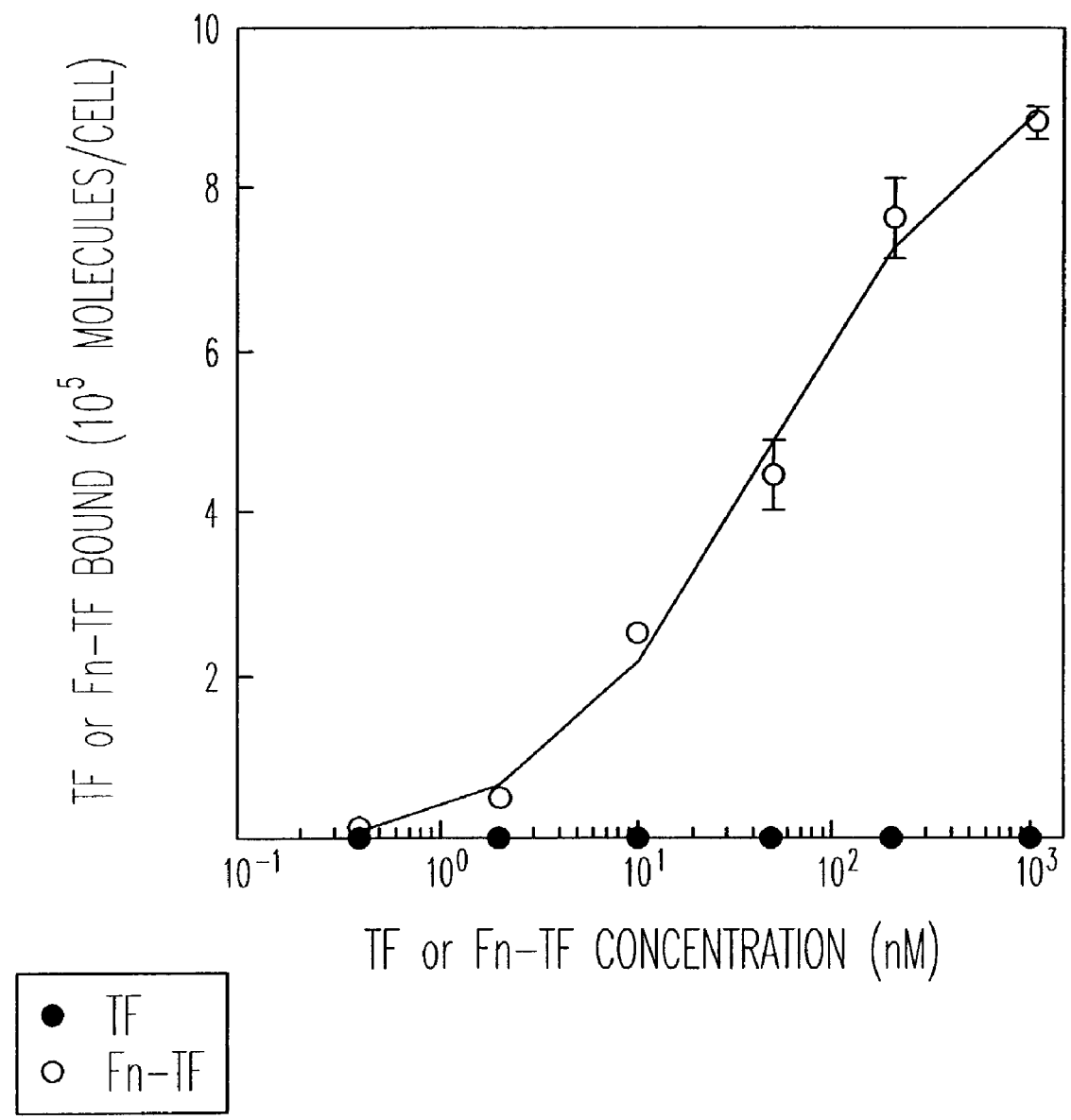
FIG. 5 graphically illustrates the binding of the Fn-TF protein to integrin expressing CHO K1 cells. The amount of Fn-TF (O) bound increases as the Fn-TF concentration increases. In contrast, soluble Tissue Factor (TF1-218)(•) shows no appreciable association with CHO K1 cells.

FIG. 5 shows that increasing amounts of Fn-TF become associated with CHO cells as the amount of Fn-TF increases. In contrast, soluble TF1-218 has no demonstrable association with CHO cells.

Induction of Localized Coagulation by Docked Fn-TF

Activation of the coagulation cascade was measured using a coagulation assay. Varying concentrations of Fn-TF or Tissue Factor were incubated with CHO K1 cells for 15 minutes. Coagulation assays were initiated with addition of 100 ul of pooled normal human plasma. The coagulation time was recorded as the interim between the initiation of assay and the appearance of the first fibrin strands.

Figure 6:
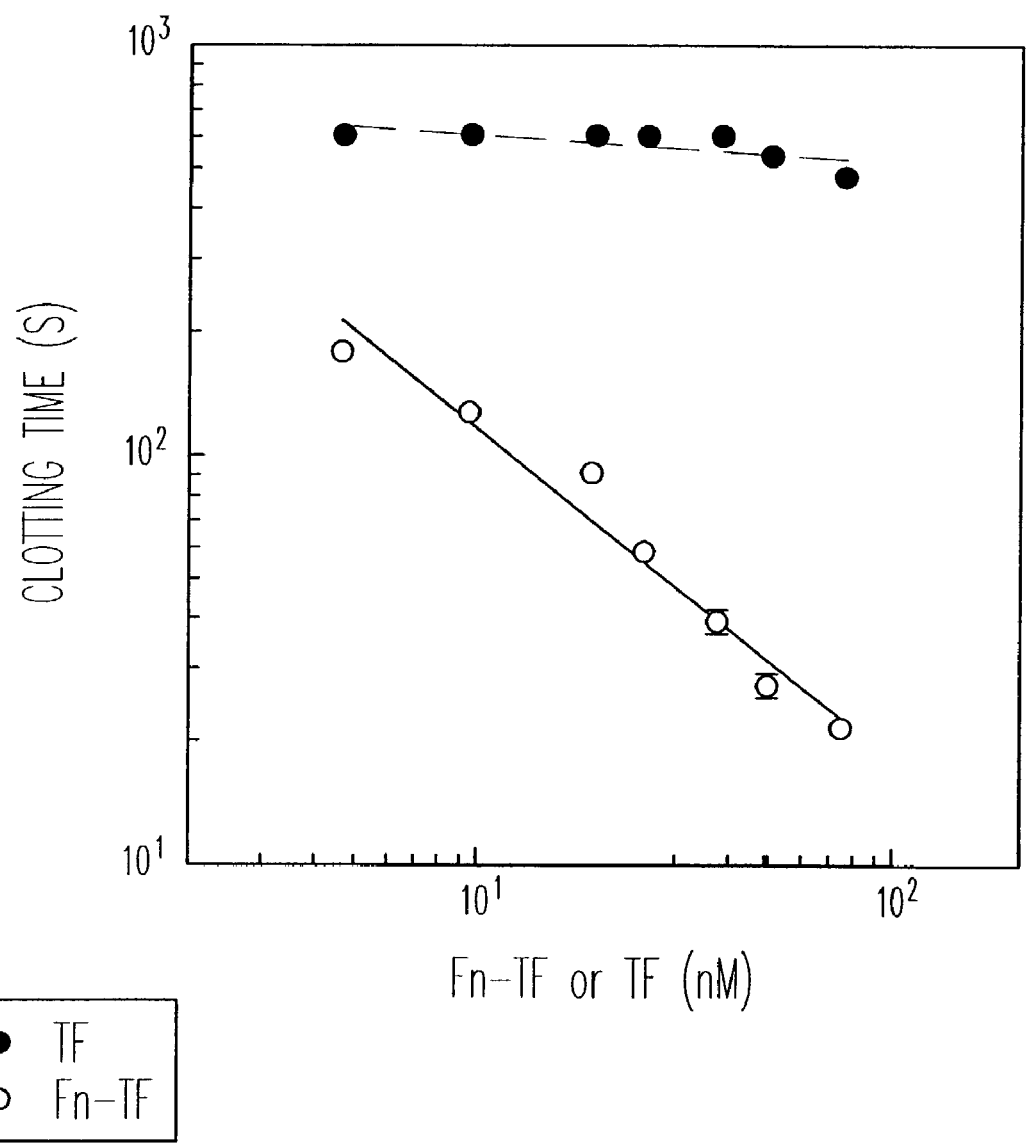
FIG. 6 graphically illustrates the initiation of localized coagulation on the cell surface by Fn-TF (O) or soluble Tissue Factor (TF1-218) (•) using cells that express integrin (CHO K1 cells). Coagulation time decreased with increasing concentrations of Fn-TF but not with soluble TF. These data indicate that the binding of Fn-TF to integrin led to the regeneration of thrombogenic function by association of the Fn-TF molecule with the cell surface through interaction with integrin. These data also indicate that the Fn-TF protein can assume a conformation that is substantially similar to that of native, transmembranic Tissue Factor so that initiation of the coagulation protease cascade is substantially unaffected by a heterologous Selective Binding Domain.
Figure 7:
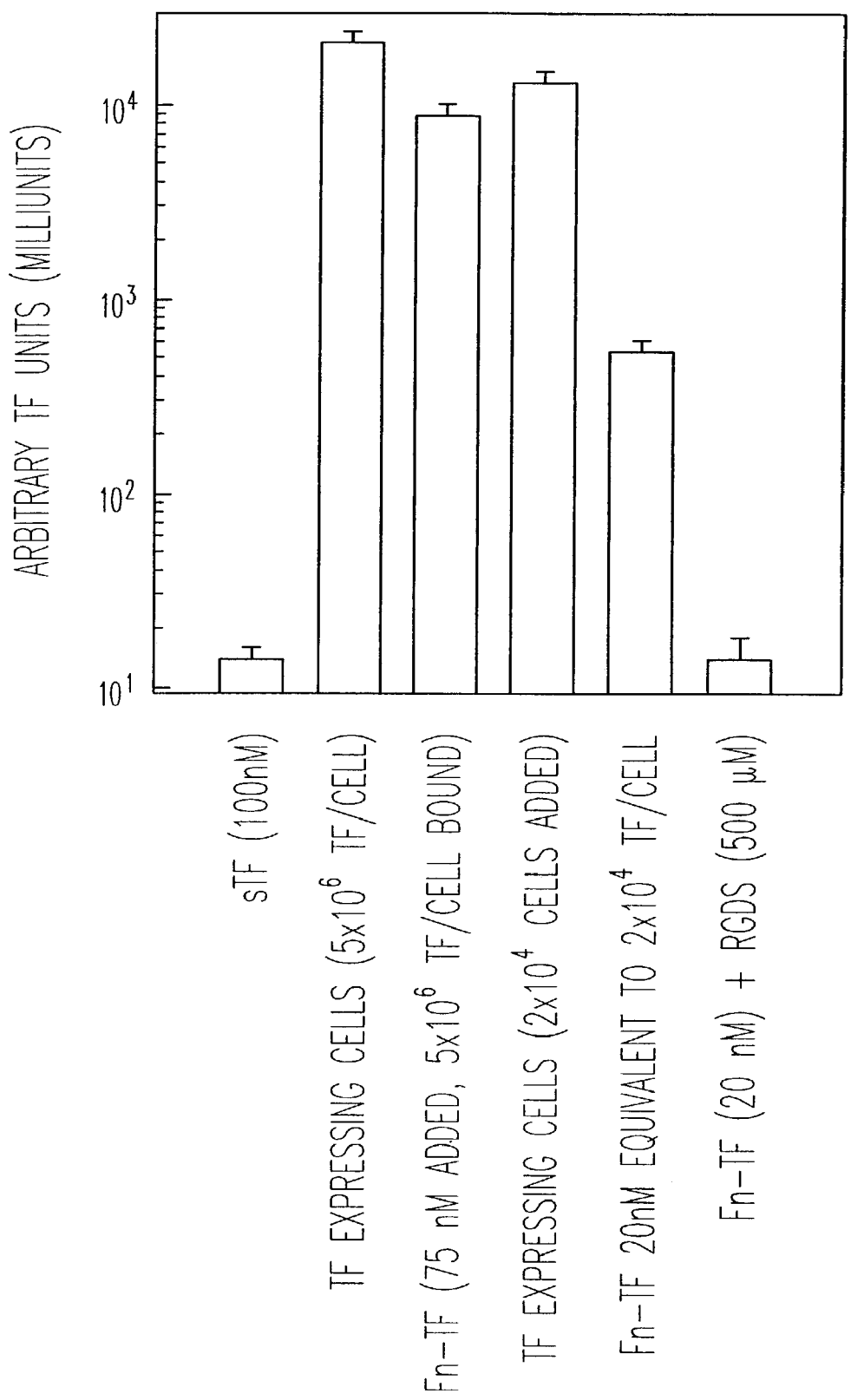
FIG. 7 graphically compares the thrombogenic activity of the Fn-TF protein with native Tissue Factor and further illustrates that an RGDS (SEQ ID NO: 17) peptide can competitively inhibit Fn-TF activity. The coagulation activity of the Fn-TF construct can be almost completely inhibited with the RGDS peptide (Fn-TF (20 nM)+RGDS (500 μM)). In the presence of RGDS, Fn-TF has low activity similar to soluble Tissue Factor (sTF), which cannot assemble into a thrombogenic complex on the cell. The RGDS peptide can therefore compete for binding to integrin, thereby blocking the binding of the fibronectin domain of Fn-TF to integrin. These data further confirm that the coagulation activity of the Fn-TF construct is dependent on the binding of a Selective Binding Domain.

FIG. 6 shows that the coagulation cascade was efficiently initiated by the Fn-TF complex bound to CHO K1 cells. In particular, the coagulation time decreases as the Fn-TF concentration increases suggesting the fibronectin docking domain can efficiently bind to the integrin on the CHO cell surface, and that such a docked Fn-TF complex can adopt the necessary conformation for initiating the coagulation cascade (FIGS. 6 and 7). With CHO K1 cells alone, plasma coagulation takes greater than 400 seconds (1 milliunit activity). However, when the Fn-TF fusion protein is bound to form approximately 100,000 Fn-TF:integrin complexes per cell, the coagulation time is reduced to about 20 seconds (40,000 milliunits activity). The Fn-TF fusion protein appears to be a more efficient activator of the coagulation cascade than is achieved with antibody mediated targeting of Tissue Factor observed previously (Huang, Molema et al. 1997).

Inhibition of Fn-TF Coagulation Activity by the RGD Peptide

The coagulation activity of the Fn-TF fusion protein can be fully blocked by addition of the RGDS (SEQ ID NO:17) (FIG. 7). These data indicate that the RGDS peptide, which binds to the integrin, inhibits binding of the Fn-TF fibronectin docking domain to the integrin on the cell surface. The increased coagulation activity of Fn-TF relative to TF1-218 is therefore apparently due to the fibronectin selective binding domain, which binds and orients the extracellular domain of Tissue Factor into proximity with anionic phospholipid membrane microdomains and thereby facilitates the association of Factor VIIa with Tissue Factor and the cell surface.

Coagulation Activity of Fn-TF Versus Full Length Tissue Factor

The coagulation activity of the Fn-TF fusion protein with CHO K1 cells was compared with the coagulation activity of a CHO K1 cell line that stably expressed full-length recombinant Tissue Factor. Approximately, $5 \times 10^5$ Fn-TF molecules are bound per cell when 75 nM Fn-TF fusion protein is incubated with $10^5$ CHO K1 cells in 100 ul. A similar number of CHO K1 cells that are expressing approximately $5 \times 10^5$ native Tissue Factor molecules have approximately the same level of coagulation activity as the $10^5$ CHO K1 cells exposed to 75 nM Fn-TF (FIG. 7).

Hence, the thrombogenic activity of Tissue Factor is largely dependent upon binding to a cellular membrane and upon physical alignment with the cell surface in a manner that is similar to that of native Tissue Factor structure. Whereas the lack of a membrane assembly domain eliminates the major mechanism for proper docking of the Tissue Factor:Factor VIIa:Factor X complex on the cell surface, as well as the associated protease activities, the data provided in this example indicate that the N-terminus of Tissue Factor tolerates introduction of heterologous selective binding domains and that those binding domains can facilitate proper cell membrane association and orientation to restore the protease activity of Tissue Factor.

Hence, fusion of tissue-selective binding domain to the extracellular domain of Tissue Factor can target coagulation within that selected tissue type.

EXAMPLE 2

Prostate Tumor Infarction By Tissue Factor:PSMA Inhibitor

In this example, intravascular thrombosis was induced within mouse tumors by administration of an Asp-β linked-Glu (DβE)-biotin:streptavidin-Tissue Factor complex. The Asp-β linked-Glu dipeptide is a binding inhibitor of PSMA and, in this example, acts as a Selective Binding Domain. Use of a small peptide inhibitor such as D-β-E has benefits over the use of an anti-PSMA antibody because it is easier to produce, and it is small so that the thrombogenic potential is maximized, for example, with small tumor vessels. The Asp-β linked-Glu Selective Binding Domain directs an associated Tissue Factor polypeptide to PSMA-expressing cells that line the blood channels of prostate tumors. After association with PSMA-expressing cells, the Tissue Factor domain initiates localized thrombosis and infarctive necrosis of the prostate tumor. This results in tumor regression without harming the animal host.

Reagents

Purified human plasma factor VIIa was from Hematologic Technologies (Essex Junction, Vt.). Liposome incorporated doxorubicin (Doxil™) was from ALZA corporation (Mountain View, Calif.). *Streptomyces avidinii* was from the ATCC and grown for isolation of DNA using the QIAmp kit method (QIAGEN, Valencia, Calif.).

Antibodies

Anti-PSMA antibodies (7E11C5) were used to characterize the Mat Lu rat and LuCap mouse prostate tumor models. Monoclonal antibodies against mouse CD31 (MEC 13.3) and rat CD31 (TLD-3A 12) were from PharMingen (La Jolla, Calif.). Biotinylated rat anti-mouse CD31 antibody and a FITC labeled mouse anti-human CD31 antibody were also purchased from Pharmingen, La Jolla, Calif. Murine monoclonal antibody J591 specific for the extracellular domain of PSMA was provided by Dr. N. Bander (School of Medicine, Cornell University). Biotinylated 7E11C-5 antibody was from Dr. J. Murphy, Pacific Northwest Cancer Foundation, Seattle, Wash. The 7E11C-5 antibody epitope was mapped to the N-terminal intracellular portion of human PSMA that is not present in the mouse PSMA homologue. The anti-CD31 antibodies react with endothelial cells.

Streptavidin-Tissue Factor Fusion Protein

To determine whether a PSMA inhibitor could serve as a Selective Binding Domain to target Tissue Factor to prostate tumors and then induce tumor necrosis, an Asp-β-linked-L-Glutamate (DβE) biotinylated dipeptide was synthesized. This peptide was made to interact with and bind to a streptavidin moiety that was N-terminally attached to the extracellular domain of Tissue Factor (SEQ ID NO:5), termed streptavidin-TF. The streptavidin-TF fusion protein was produced in *E. coli* and folded to generate a tetramer capable of binding to four biotin molecules. The details involved in generating this protein are described below.

Tissue Factor cDNA containing amino acids 3 to 311 was obtained by PCR of a human cDNA library (Clontech, Palo Alto, Calif.) with the following primers:

```
                                              (SEQ ID NO:20)
BM21:   5'-ACTACAAATACTGTGGCAGCA-3'; and (SEQ ID NO:21)
BM33:   5'-TTTAAGCTTTCACGTGCCCATACACTCTACCGG-3'.
```

The resulting 639 bp fragment was isolated by gel electrophoresis and subjected to a second PCR with primer BM33 (SEQ ID NO:21) and the following primer:

```
BM51:  5'-AAATGGATCCTGGTGCCTAGGGGCCCGGGACTACAAATACTGTGGCAGCA-3'.   (SEQ ID NO:22)
```

The resulting 670 bp fragment was digested with BamHI and HindIII and ligated into the BamHI and HindIII sites of the vector pTrcHisC (Invitrogen, Carlsbad, Calif.). The BM51 oligo also encodes a thrombin cleavage site (Val-Pro-Arg-Gly-Ser, SEQ ID NO:23) for selective proteolytic deletion of the His tag from the expressed protein. This plasmid (NuV120) was further modified to contain a linker sequence with three repeats of $Gly_4Ser$ (SEQ ID NO:24) between the thrombin cleavage sequences and those of Tissue Factor. The following overlapping oligos were annealed and inserted into the BamHI and AvaI sites of NuV120:

```
nuv20-1: 5' GATCTTGGTCCCTAGGGGATCCGCAGAACCAATGCCT 3';      (SEQ ID NO:25)

nuv20-2: 5' PO4-CACTCGCTAAACTTCAGTCAATACCTCTGGTATACT 3';     (SEQ ID NO:26)

nuv20-3: 5' PO4-GGTACCGGAGGAGGCGGTTCAGGTGGTGGAGGTTCA 3';     (SEQ ID NO:27)

nuv20-4: 5' PO4-GGAGGTGGAGGTTCTC 3';                         (SEQ ID NO:28)
```

-continued

```
nuv20-5: 5' PO4-TCTGCGGATCCCCTAGGGACCAA 3';                    (SEQ ID NO:29)

nuv20-6: 5' PO4-AGGTATTGACTGAAGTTTAGCGAGTGAGGCATTGGT 3';  (SEQ ID NO:30)

nuv20-7: 5' PO4-CCACCTGAACCGCCTCCTCCGGTACCAGTATACCAG 3';  (SEQ ID NO:31)

nuv20-8: 5' CCGGGAGAACCTCCACCTCCTGAACCTCCA 3'.                 (SEQ ID NO:32)
```

The resulting plasmid (NuV127) encodes a His-tag, a thrombin cleavage site, three repeats of the spacer $Gly_4Ser$ (SEQ ID NO:37), and Tissue Factor residues 3 to 211. This vector can be used to create expression vectors for various Selective Tissue Vascular Thrombogens by inserting a cDNA sequence encoding the derived amino acids into unique BamHI and KpnI sites. The streptavidin gene was amplified by PCR with Pfu polymerase (Stratagene) using the following oligonucleotides:

```
strep1: 5' ACCACGGTCTCGATTACGGC 3'; (SEQ ID NO:33)
and strep2: 5' ACTACTGCTGAACGGCGTCG 3'. (SEQ ID NO:34)
```

Such PCR amplification results in a 514 bp fragment. The 514 bp fragment was purified and used as template for a second PCR amplification, this time with the following oligonucleotides:

```
                                              (SEQ ID NO:35)
strep3:   5' CACACAGGATCCGCCGCCGAGGCCGGCATCAC 3';
and (SEQ ID NO:36)
strep4:   5' CACACAGGTACCCTGCTGAACGGCGTCGAGCG 3'.
```

BamHI and KpnI sites, respectively, are underlined in the above oligonucleotide sequences and extra nucleotides in italics were added for efficient enzyme digestion. The resulting DNA fragment of 486 bp was purified, digested with BamHI and KpnI and cloned into the BamHI and KpnI sites of NuV127. The resulting plasmid, NuV159, expresses a Streptavidin-Tissue Factor.

BL21 cells transformed with the NuV159 plasmid were grown in Super Medium (25 g tryptone, 15 g yeast extract and 5 g NaCl per liter) supplemented with biotin. Cells were induced with 1 mM IPTG when the $OD_{600}$ reached 0.6 and were cultured for 24 hours at 37° C. The protein (Strep-TF) accumulated in inclusion bodies, which were isolated as described in Donate et al., Dimerization of tissue factor supports solution-phase autoactivation of factor VII without influencing proteolytic activation of factor X. Biochemistry, 39: 11467-11476, 2000. The inclusion bodies were solubilized in 6 M guanidinium hydrochloride (GuHCl), pH 8.0, and the protein construct was partially purified in a Ni-NTA (QIAGEN) column equilibrated and washed with 6 M GuHCl pH 8.0 and eluted with 250 mM imidazole, 6 M GuHCl, pH 8.0. Protein folding was performed by dilution of GuHCl solubilized Strep-TF in 20 mM Tris, 300 mM NaCl, 0.8 M GuHCl pH 8.0 and glutathione redox buffer. After 16 hours at 4° C., the sample was concentrated with a Pellicon XL concentrator (MWCO, 10,000). The His tag is removed by thrombin digestion and the protein construct purified in two steps with a Source 15Q 16/10 column followed by a Sephacryl S-200 gel filtration. FIG. 9A depicts a silver-stained gel illustrating the purity of the streptavidin-TF protein.

A DβE-biotin:streptavidin-TF complex was prepared by mixing excess DβE-biotin (>10 to 1 molar concentration ratio) with streptavidin-TF protein in saline. The binding of the DβE-biotin peptide to the streptavidin-TF protein was allowed to proceed for 30 min. The resulting DβE-biotin:streptavidin-TF complex was dialyzed against two changes of saline. FIG. 9B illustrates the activity of the D-β-E-biotin:streptavidin-Tissue Factor complex in a Factor X generation assay.

Before injection into animals, the DβE-biotin:streptavidin-TF complex was mixed with an equal molar ratio of Factor VIIa for 10 min. This permitted formation of the functional DβE-TF:Factor-TF:Factor VIIa thrombogenic complex.

Cell Culture

Cell lines LnCap and the Mat Lu cell were from ATCC. The LnCap cells were cultivated in RPMI-1640 medium supplemented with 10% fetal calf serum, glutamine (2 mM), HEPES (10 mM), sodium pyruvate (1 mM) and glucose (4.5 g/L). Mat Lu cells were cultured in RPMI-1640 with 10% fetal calf serum, glutamine (2 mM), and 250 nM dexamethasone.

Factor Xa Generation Assay

Factor Xa generation assays were performed as described in Ruf, et al. (J. Biol. Chem., 266, pg. 2158-66, 1991) with modifications to provide for association of the STVT constructs to PSMA expressing LnCap cells. LnCap cells were plated at $8\times10^4$ per well in 96 well plates and allowed to attach for 4 hours in the medium described above. Medium was replaced with HBSA buffer (150 mM NaCl, 5 mM $CaCl_2$, 0.5% BSA, 20 mM Hepes, pH 7.4) and serial concentrations of DβE:Strep-TF:VIIa or Strep-TF:VIIa complex were added to the wells. After incubation for 5 minutes, factor X was then added to a final concentration of 1 μM. After 5 minutes at 37° C. the limited proteolytic conversion of factor X to factor Xa was arrested with 100 mM EDTA. Factor Xa amidolytic chromogenic substrate Spectrozyme Xa (American Diagnostica, Greenwich, Conn.) was added to a final concentration of 200 μM and substrate hydrolysis was determined kinetically at OD 405 in a spectrophotometric plate reader (Molecular Devices, Sunnyvale, Calif.).

Animal Models

Cell lines LnCap and the Mat Lu cell were from ATCC. The PSMA positive human prostate carcinoma (CaP) xenograft, LuCap 58, was carried as a xenograft in WEHI nude mice (The Scripps Research Institute Breeding Facility). See Bladou et al., In vitro and in vivo models developed from human prostatic cancer. Prog. Urol., 7: 384-396, 1997. The tumors were passaged by implantation of ~2 $mm^3$ fragments in the subcutaneous tissue of the back of the mice. The rat Mat Lu prostate carcinoma was carried in male Copenhagen rats aged 4 to 6 weeks (Harlan Sprague-Dawley, Germantown, N.Y.) innoculated with $5\times10^5$ Mat Lu cells per subcutaneous site on the back.

Treatment of tumors was initiated once tumors reached 200 $mm^3$ through bolus intravenous injection of the Selective Tissue Vascular Thrombogen or a control protein (0.1 mg/Kg based on strep-TF protein) and repeated twice at two-day intervals. For combination therapies, liposomal doxorubicin (Doxil™) at 2 mg/kg was separately injected intravenously. Tumor growth and other physical signs were monitored daily including gross evidence of tumor necrosis, local tumor ulceration as well as evidence of toxicity including mobility, response to stimulus, eating, and weight of each animal. The studies have been reviewed and approved by the Institutional Animal Care and Use Committee of The Scripps Research Institute. The work was conducted in the TSRI facilities which are accredited by the Association for the Assessment and Accreditation of Laboratory Animal Care. The Scripps Research Institute maintains an assurance with the Public Health Service, is registered with the United States Department of Agriculture and is in compliance with all regulations relating to animal care and welfare.

Immunohistochemistry

Immunohistochemical analysis was performed on formalin fixed as well as fresh frozen 5 μm tissue sections mounted on poly-lysine coated slides. For endothelial identification, biotinylated murine anti-rat CD-31 monoclonal antibody (TLD-3A12) or biotinylated rat anti-mouse CD-31 monoclonal antibody (MEC 13.3) were used at 1 μg/ml as first antibody then the reaction was developed with fluorescein conjugated strepavidin. For identification of PSMA in frozen sections, reaction with mouse monoclonal antibody J591 was followed by biotinylated rabbit anti-mouse IgG and the reaction was visualized with Texas-red conjugated strepavidin. Staining of PSMA in formalin fixed tissue was performed with biotinylated 7E11C-5 antibody. The tissue sections were analyzed with the aid of laser scanning confocal microscopy (Bio-Rad, Hercules, Calif.).

Coagulation Assay

The coagulation activity of the DβE-biotin:streptavidin-TF:Factor VIIa thrombogenic complex was assayed using a cell mediated coagulation assay employing CHO K1 cells that stably express PSMA. Different concentrations of DβE-biotin:streptavidin-TF:Factor VIIa thrombogenic complex (in 50 ul) were incubated with $10^5$ PSMA expressing CHO K1 cells (also in 50 ul) at room temperature for 15 min to allow the DβE-biotin:streptavidin-TF:Factor VIIa thrombogenic complex to associate with PSMA on the cell surface. At the end of this incubation, 100 ul citrated pooled human plasma was added and the assay was initiated by adding 100 ul 20 mM $CaCl_2$ that had been pre-warmed to at 37° C. Assays using CHO K1 cells without PSMA were used as controls. The clotting time was recorded as the interim between the initiation of the reaction and the occurrence of the first strands of fibrin gel. This assay was used to guide the construction of fusion proteins and to quantify the activity of the DβE-biotin:streptavidin-TF:Factor VIIa thrombogenic complex in different preparations.

Combined Treatment with the DβE-biotin:streptavidin-TF:Factor VIIa Thrombogenic Complex and Doxorubicin Treatment of tumor-bearing rodents was initiated when tumors reached 200 $mm^3$ by bolus i.v. injection. Some test animals were injected with DβE-biotin:streptavidin-TF:Factor VIIa thrombogenic complex (0.1 mg/Kg based on streptavidin-TF total protein) plus doxorubicin (2 mg/kg, 3.5umol/kg). Other test animals were injected with DβE-biotin:streptavidin-TF:Factor VIIa thrombogenic complex (0.1 mg/Kg based on streptavidin-TF total protein) alone. Control animals were injected with doxorubicin (2 mg/kg, 3.5umol/kg). Mock-treated animals received no doxorubicin and no thrombogenic complex. The treatment is repeated daily. The doxorubicin dosage is determined according to the MTD (maximum tolerated dose) published for daily injection for five days, which between 2.8 umol/kg to 3.6 umol/kg. Tumor growth was monitored daily through 4 weeks and until death. Tumor size was measured daily from the day of initial treatment.

Statistical analysis

Statistical significance was determined by the two-tailed Student=s t test, except for statistical significance of survival curves which utilized the Logrank test using GraphPad Prism version 3.00 (GraphPad Software, San Diego Calif. USA).

Results

Immunohistological Analysis

Figure 8A:
FIG. 8A is a photomicrograph of a formalin fixed section of a LuCap 58 prostate tumor stained with the biotinylated anti-PSMA antibody 7E11C-5. Note the intense positive stain of PSMA (arrows) on the endothelial surface of the tumor microvasculature.
Figure 8B:
FIG. 8B is an expanded view of the inset identified on a photomicrograph of FIG. 8A. Channels stained with biotinylated anti-PSMA antibodies are identified (arrows). Note that the intensity of the staining is greatest in the lining of the lumen for each channel structure.

PSMA was detected on the vessels of a xenograft model of human prostate tumors (LuCap 58) using the 7E11 antibody, and also using a biotinylated peptidyl inhibitor (Asp-β-Glu) of PSMA enzymatic activity. Strong PSMA expression was detected on the luminal surfaces of the vessels of the PSMA positive human LuCap 58 xenograft grown in nude mice (FIG. 8A and 8B). The epitope recognized by the murine 7E11C-5 antibody was mapped to the N-terminal intracellular portion of human PSMA that is not present in the mouse PSMA homologue. Therefore, the detected PSMA was human PSMA. This observation indicates that the tumor vasculature present in this tumor model is of human origin, even though the LuCap model has been propagated in nude mice for much too long for primary non-transferred endothelial cells to survive in these tumors. Such data indicate that the tumors themselves are generating microvascular lining cells or that human PSMA from the tumor cells was acquired by transfer to endothelial cells of the mouse that have grown into the tumor.

Immunohistochemical analysis of the human LuCap tumors clearly identified PSMA positive cells that line and thereby delineate the microscopic channels with structural characteristics not unlike microvascular channels (FIG. 8A and 8B). PSMA expression is more intense on the aspect of tumor cell membranes that constitutes the luminal surface of the channels (FIG. 8B).

Figure 8C:
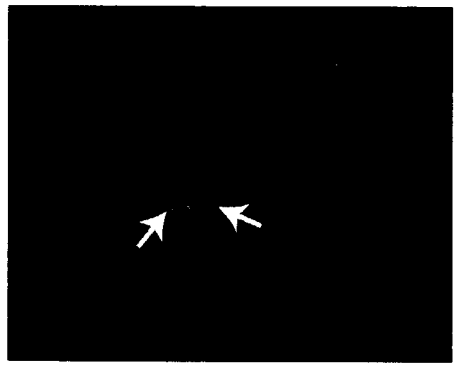
FIG. 8C is a photomicrograph showing LuCap xenograph tumor cells stained red (arrows) with anti-PSMA antibody while most of the surrounding endothelial cells stained green with anti-CD31 antibody. The red and green staining patterns are mutually exclusive indicating that PSMA is not expressed on CD31 positive endothelial cells.

A second piece of evidence indicates that the PSMA-positive cells lining the vessels of the tumors are not endothelial cells. Frozen sections of LuCap 58 tumors were immunohistochemically stained with biotinylated rat anti-mouse CD31 antibody and with an FITC-labeled mouse anti-human CD31 antibody. While the FITC-labeled anti-mouse CD31 reacted positively with the tumor vessels lining cells in these sections (FIG. 8C), the rat anti-human CD31 staining was negative. Double staining of the LuCap tumor with anti-mouse CD31 antibody and PSMA specific antibody (FIG. 8C) indicated that these PSMA-expressing microchannels are distinct and mutually exclusive of microvascular channels lined by CD31 positive cells. These data therefore indicate that human endothelial cells do not exist in the LuCap 58 tumor. In Mat Lu tumors, the anti-PSMA antibody and anti-CD31 antibody reacted with almost entirely mutually exclusive cell surfaces, also indicating that the PSMA positive cells lining blood vascular channels are not endothelial cells.

Figure 8D:
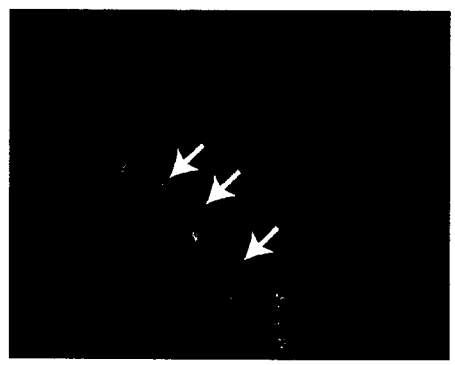
FIG. 8D depicts a section of a rat Mat Lu tumor where PSMA was observed to co-localize with cells that line the channels in these tumors. Rats were injected intravenously with $10^{12}$ M 13 bacteriophage and tumors were harvested about 2 min. later. The tumor channels stained red with anti-PSMA (J591) antibodies (arrow) and the circulated phage were stained green with anti-phage antibodies (arrows). These results indicate that the PSMA positive cell lined channel structure is connected with the circulatory system of the animal.
Figure 8E:
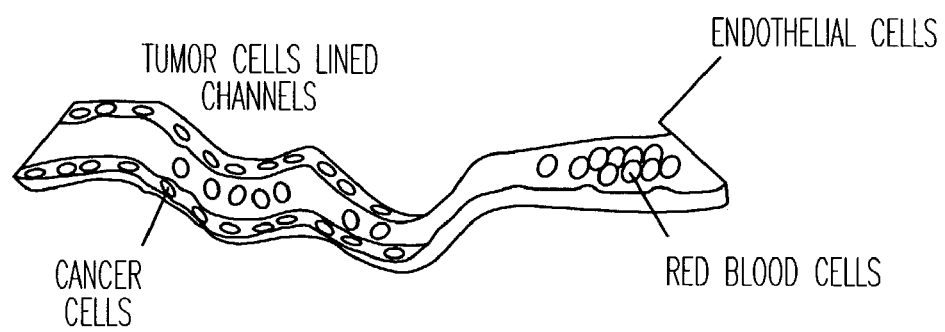
FIG. 8E is a schematic representation of such vasculogenic mimicry in which tumor cells differentiate into an endothelial-like phenotype and form channel structures that connect to natural endothelial-lined tumor vessels and carry blood into the tumor.

To investigate that whether the PSMA-positive cells that lined the channels in these tumors were part of the tumor vasculature, bacteriophage M13 was injected into the blood stream of the animal as a marker. Tumors were harvested minutes after the injection and frozen sections were prepared from these samples. Extensive experience with in vivo phage panning has proven that phage will remain in the tumor vasculature and can be easily recognized with anti-phage antibody staining. Double staining with PSMA antibody and anti-phage antibody revealed that PSMA lined the channel structures stained by phage and through which blood flows (FIG. 8D). These data indicate that the channels lined by PSMA-expressing cells are part of the tumor vasculature (see schematic diagram provided in FIG. 8E). Cells lining the blood vessels and in contact with the blood are tumor cells, rather than endothelial cells. Similar microchannels lined by PSMA positive cells were also observed in syngeneic rat Mat Lu tumors.

The STVT Functionally Associates with PSMA Positive Cells.

A factor Xa generation assay was used to test whether the DβE-biotin:streptavidin-TF:Factor VIIa complex could align properly on an anionic cell membrane surface and properly associate with factor X substrate that has localized to the same locus. As illustrated in FIG. 9B, the DβE-biotin:streptavidin-TF:Factor VIIa complex but not the streptavidin-TF:Factor VIIa complex functions on LnCap cells to generate Factor Xa in the Factor Xa generation assay described above. Hence, the DβE-biotin:streptavidin-TF:Factor VIIa complex can proteolytically convert factor X to factor Xa while bound to LnCap cells.

The factor Xa generation assay requires the functional assembly of the assembled DβE:Strep-TF:VIIa complex on PSMA expressing LnCap cells. Unlike most tumor cells, LnCap cells do not express Tissue Factor as indicated by coagulation assays and western blot examination (data not shown). LnCap cells also do not directly form factor Xa from factor X and therefore cannot drive the thrombogenic cascade (see streptavidin-Tissue Factor control in FIG. 9B). The dose dependent increase of factor Xa generation by the DβE:Strep-TF:VIIa complex in the presence of LnCap cells was striking in comparison to the control LnCap cells treated with the streptavidin-Tissue Factor molecule that lacked the PSMA targeting element (FIG. 9B). These data indicate that the DβE:Strep-TF:VIIa complex functionally assembles on the cell surface through binding of DβE to PSMA and initiates the thrombogenic cascade.

Tumor Necrosis

Mat Lu tumors were generated by subcutaneous inoculation of $0.5 \times 10^6$ tumor cells per site in the subcutaneous tissue of the back of the Copenhagen rats. After 7 days the tumors grew to an average diameter of 1 cm. Treatment is initiated at this time by bolus intravenous injection of the DβE-biotin:streptavidin-TF:Factor VIIa complex at a dose of 0.1 mg streptavidin-TF per Kg body weight. Treatment was repeated daily for 7 days. Tumor growth was measured daily and graphed. Key physical signs were monitored, including:

(a) Tumor necrosis and infarction. Mat Lu tumors are non-necrotic tumors with fast initial growth but slow progression. Local ulceration is a important sign of targeted thrombosis;
(b) Apparent health of each rat; and
(c) Mobility and response to stimulus.

The control streptavidin-TF protein was not toxic in rats over a wide range of concentrations, thereby permitting evaluation of the potential for selective tumor thrombosis and infarctive necrosis in tumor bearing rats.

Figure 10A:
FIG. 10A-10D provides a pathological analysis of Mat Lu tumor treated with the D-β-streptavidin-Tissue factor protein.
Figure 10B:
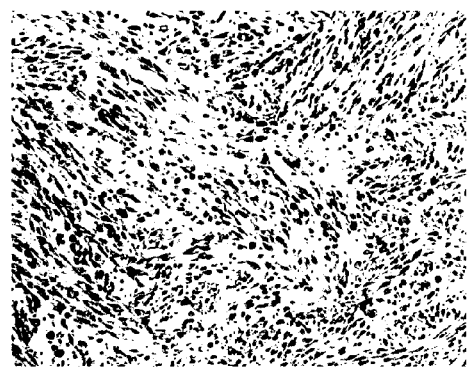
Figure 10C:
Figure 10D:
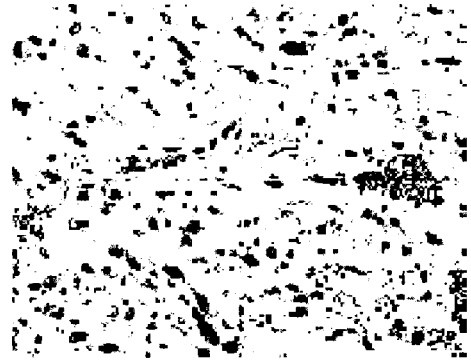

Intravenous injection of the DβE-biotin:streptavidin-TF:Factor VIIa complex was associated with a rapid wave of localized microthrombosis of blood channels within Mat Lu tumors, leading to infarctive necrosis of Mat Lu prostate tumors. As shown in FIG. 10A, the treated tumor (left) was extensively necrotic while the untreated tumor (right) showed little or no necrosis. The center of the treated tumor was liquefied upon gross and histological pathological examination, showing gross signs of ischemic necrosis. In contrast, there was no micro-thrombosis or necrotic regions in tumors from the control group (FIG. 10B). Occluded tumor microvessels were widespread in the experimental group (FIG. 10C), with platelet aggregates, packed erythrocytes and fibrin (FIG. 10D). The tumor interstitium commonly contained a few erythrocytes and was infiltrated with inflammatory cells (FIG. 10D). After the standard three infusions at two-day interval, tumors showed very extensive necrosis with liquefaction of the entire central region of the tumors. However, at the growth edge of tumors from the treated animals, a rim of viable tumor tissue remained.

Pathological studies were performed to confirm that intravenous administration of an DβE-biotin:streptavidin-TF:Factor VIIa complex induced selective thrombosis of tumor vasculature in rats bearing Mat Lu prostate cancers. Signs of tumor vasculature thrombosis were observed in tumors immediately following treatment. The center of the treated tumors showed gross signs of ischemic changes. In Hematoxylin and Eosin stained sections, the number of vessels that were occluded increased dramatically. After one hour, blood vessel thrombosis was extensive. Occlusive platelet aggregates were frequently observed in thrombi as well as red blood cells and fibrin. By 72 hours and after three treatments, the tumors showed advanced necrosis. In some tumors, the entire central region was completely liquified.

Figure 11A:
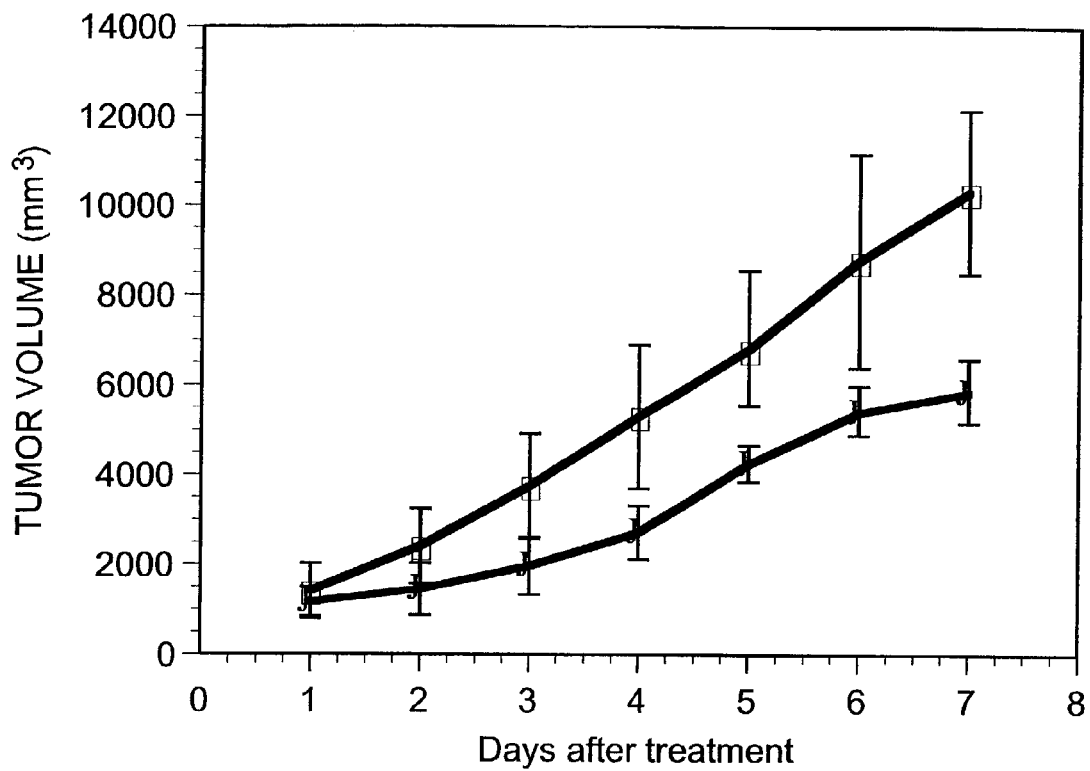
FIG. 11A graphically depicts retardation of Mat Lu tumor growth by the PSMA STVT targeting thrombogen. In the saline treated control group (square symbols), the tumor volume increased progressively and was greater than the DβE-biotin:streptavidin-TF:Factor VIIa treated group (J symbols). The tumor size was measured with a caliper and tumor volume calculated as $D \times d^2$. In this case, although tumor center is necrotic and liquified, the total tumor size remained unchanged from day zero or increased slightly as the surviving tumor cells at the rim of the tumor continued to grow.

FIG. 11A graphically depicts the retardation of Mat Lu tumor growth by the DβE-biotin:streptavidin-TF:Factor VIIa complex. In the saline treated control group (square symbols) rats, the tumor volume increased progressively and was greater than the DβE-biotin:streptavidin-TF:Factor VIIa treated group (J symbols). The tumor size was measured with a caliper and tumor volume calculated as $D \times d^2$. In some cases, although the tumor center is necrotic and liquified, the total tumor size remained unchanged or increased slightly as a result of an inflammatory response and as some surviving tumor at the periphery of the tumor continued to grow.

Figure 11B:
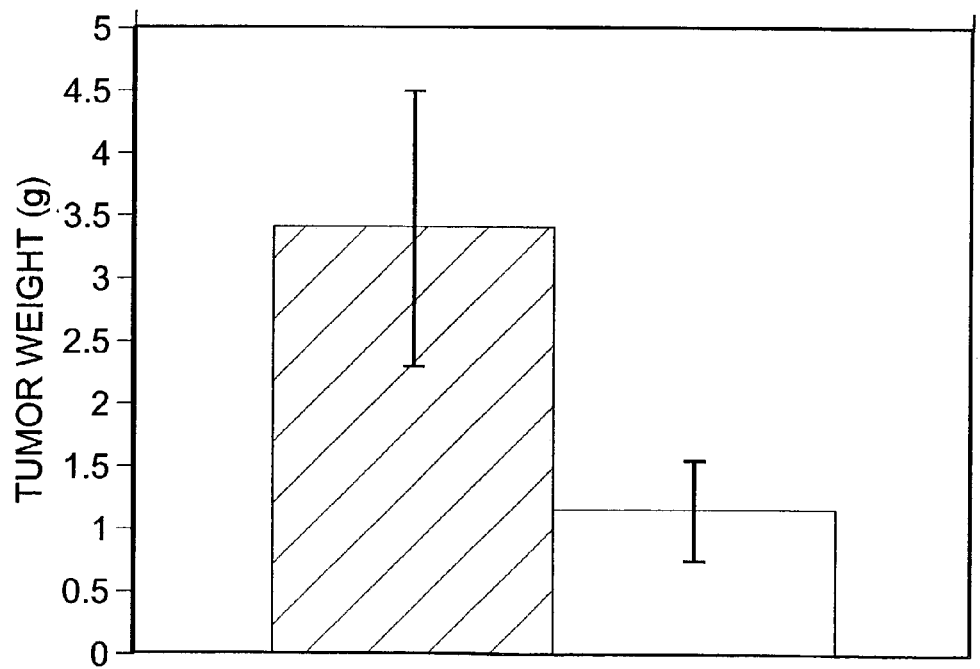
FIG. 11B graphically illustrates the weight of tumors after dissection. The average tumor weight in the treated group (STVT, white) was less than that of the control group (cross-hatched).

FIG. 11B graphically illustrates the weight of tumors after removal. The average tumor weight in the DβE-biotin:streptavidin-TF: Factor VIIa treated group (grey) was substantially less than that of the control group (black).

Combined Therapy with Doxorubicin.

Figure 12A:
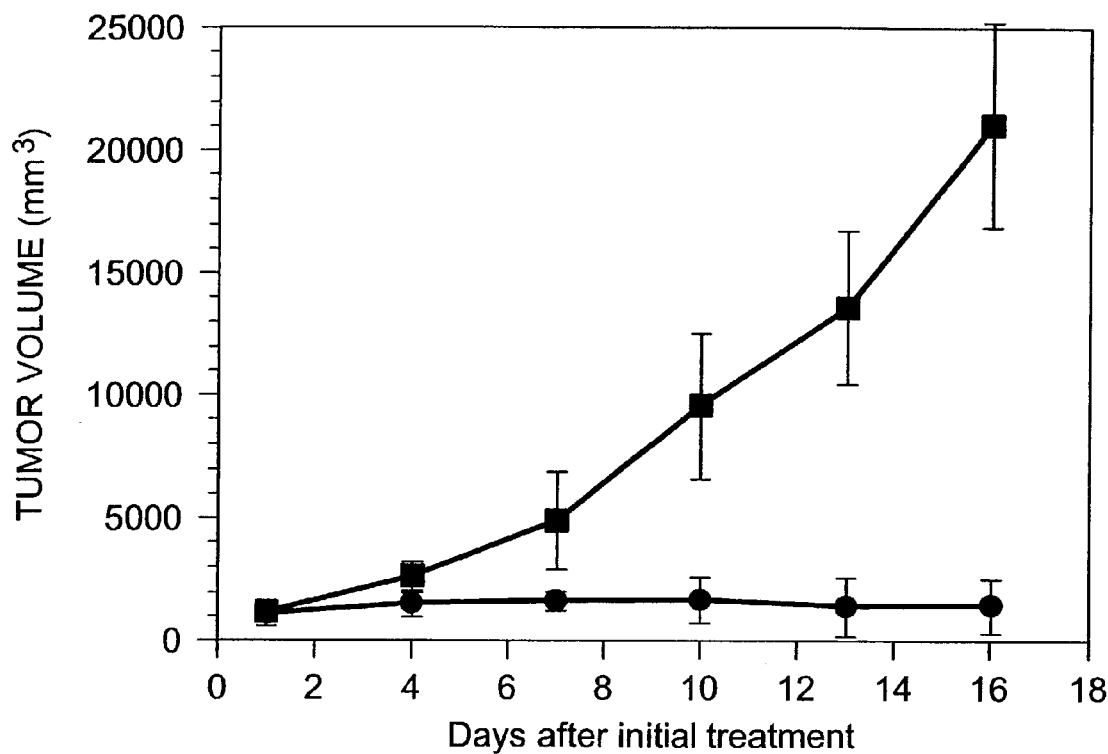
FIG. 12A illustrates that combined treatment with low doses of liposomal doxorubicin and the D-β-E-streptavidin-Tissue Factor STVT augments the tumoricidal effect of PSMA directed STVT therapy. In representative experiments, the combination of doxorubicin and the STVT resulted in nearly complete growth arrest of tumors in the treated animals (closed circles, n=12), in striking contrast to those treated only with low dose liposomal doxorubicin (closed squares, n=12). The data points represent mean ?SEM of 12 rats (p<0.001). The experiment was reproducible with comparable results.
Figure 12B:
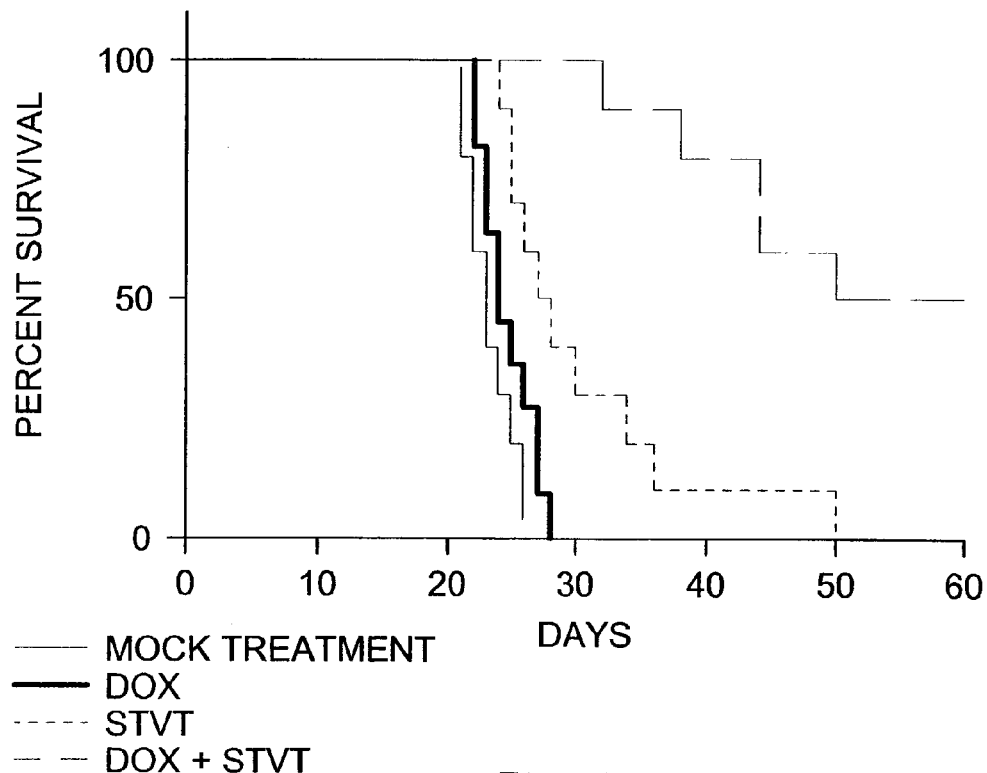
FIG. 12B graphically illustrates the percent survival of animals treated with the STVT thrombogen or doxorubicin. As illustrated, the combination of STVT thrombogen and doxorubicin treatment (Dox+STVT, long dashed line —) lead to significantly better survival than mock-treated (thin solid line) animals. Animals treated with the combination of STVT thrombogen and doxorubicin (—) also survived significantly longer than animals treated with doxorubicin only (thick solid line) or with only the STVT (short dashed line - - - ).

To address the potential to enhance selective tumor microvascular thrombosis and infarction of tumors, infusions of both the DβE-biotin:streptavidin-TF: Factor VIIa construct and low doses of liposomal doxorubicin (2 mg/Kg) were conducted. Three infusions of each were administered at two-day intervals as described above. There was virtually a complete arrest of tumor growth and gross eradication of tumors in some rats that received doxorubicin with the DβE-biotin:streptavidin-TF: Factor VIIa construct (FIG. 12A and 12B). This combination therapy also had a significant beneficial effect on survival of the tumor bearing animal hosts ($p < 0.001$, FIG. 12B). The prolongation of survival of rats treated with the DβE-biotin:streptavidin-TF: Factor VIIa alone was modest, but significant. Therapy with low dose liposomal doxorubicin alone had no measurable benefit (FIGS. 12A and 12B).

FIG. 12 graphically illustrates the synergistic effect of combined treatment with both the DβE-biotin:streptavidin-TF: Factor VIIa complex and doxorubicin. After about 5-6 days of treatment, the tumor volume of rats receiving doxorubicin had progressively increased (square symbols, FIG. 12A). There was little difference in tumor volume of between the control and doxorubicin treatment alone (data not shown).

However, animals receiving combined therapy exhibited substantially no increase in tumor volume and had significantly smaller tumors than did doxorubicin-only treated animals (round symbols, FIG. 12A). Similarly, rats receiving the DβE-biotin:streptavidin-TF: Factor VIIa complex and doxorubicin (long dashed line, FIG. 12B) survived substantially longer than rats that that received doxorubicin alone (solid line, FIG. 12B).

Therapy with PSMA Inhibitors

Figure 13A:
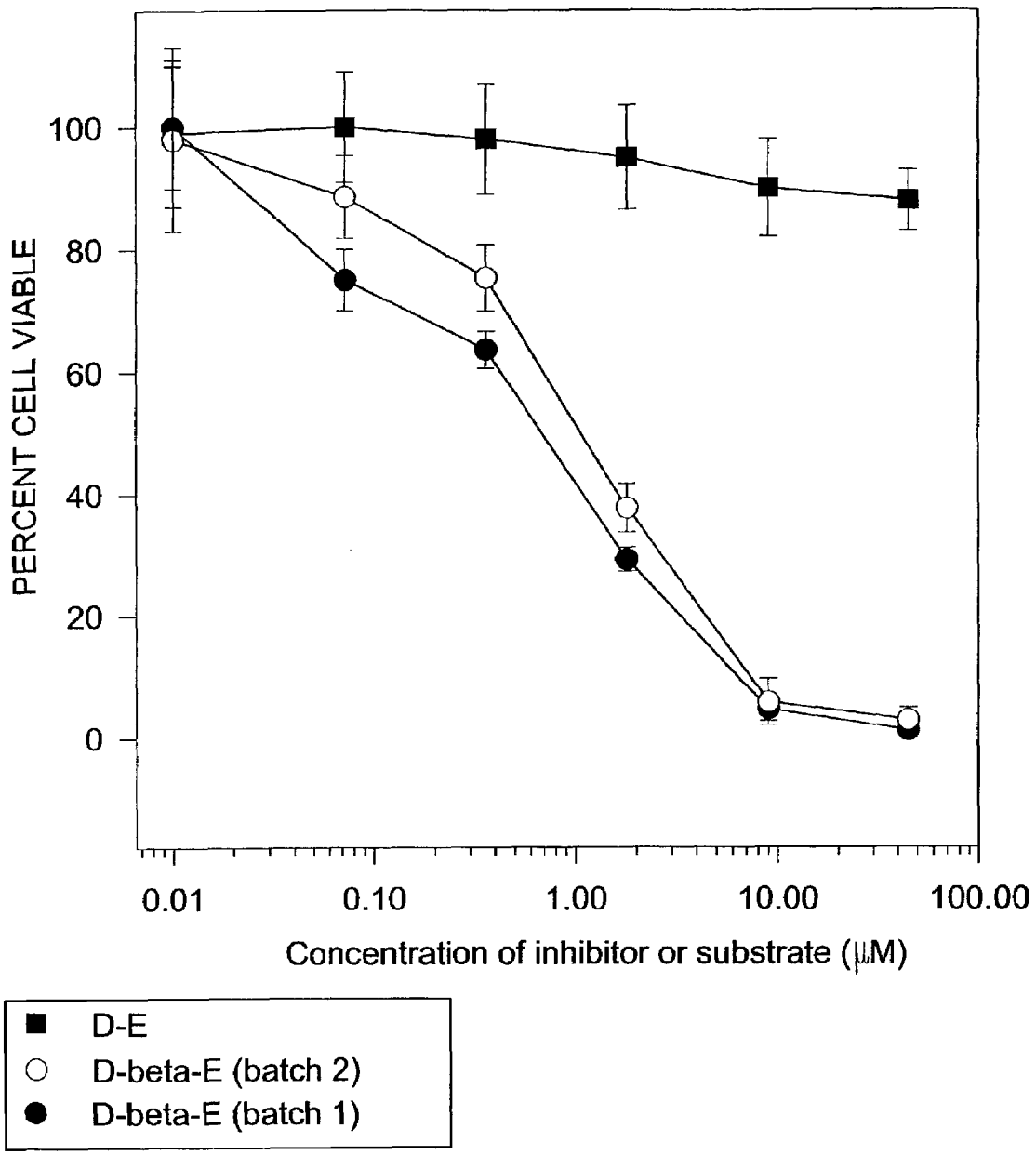
FIG. 13A graphically illustrates that as the concentration of DβE inhibitor increases the viability of PSMA expressing prostate cancer cells in culture declines. A cell proliferation and viability assay was employed to assess DβE inhibitor activity using trypan blue staining. LnCap cells (4×10⁴ cells/well) were seeded in 96 well plates. Different concentrations of the DβE inhibitor or the Asp-Glu (D-E) substrate were added to the media as indicated. The % cell viability was determined 48 hours after treatment as the number of living cells (unstained) divided by total cells count (stain+unstained cells). Inhibition of the glutamyl preferring carboxypeptidase activity of PSMA using its inhibitor Aspartyl-β-linked L glutamate (D-β-E) resulted in tumor cell death in a dose dependent manner in contrast to its physiological substrate analogue, Aspartyl-glutamate (D-E).

FIG. 13A graphically illustrates that as the concentration of DβE inhibitor increases (circular symbols), the viability of PSMA expressing prostate cancer cells declines. A cell proliferation and viability assay was employed to assess DβE inhibitor activity using trypan blue staining. LnCap cells ($4 \times 10^4$ cells/well) were seeded in 96 well plates. Different concentrations of the DβE inhibitor or the Asp-Glu (D-E) substrate were added to the media at the concentrations indicated in FIG. 13A. The % cell viability was determined 48 hours after treatment as the number of living cells (unstained) divided by total cells count (stain+unstained cells). Inhibition of the glutamyl preferring carboxypeptidase activity of PSMA using its inhibitor Aspartyl-β-linked L glutamate (D-β-E) resulted in tumor cell death in a dose dependent manner in contrast to its physiological substrate analogue, Aspartyl-glutamate (D-E).

Figure 13B:
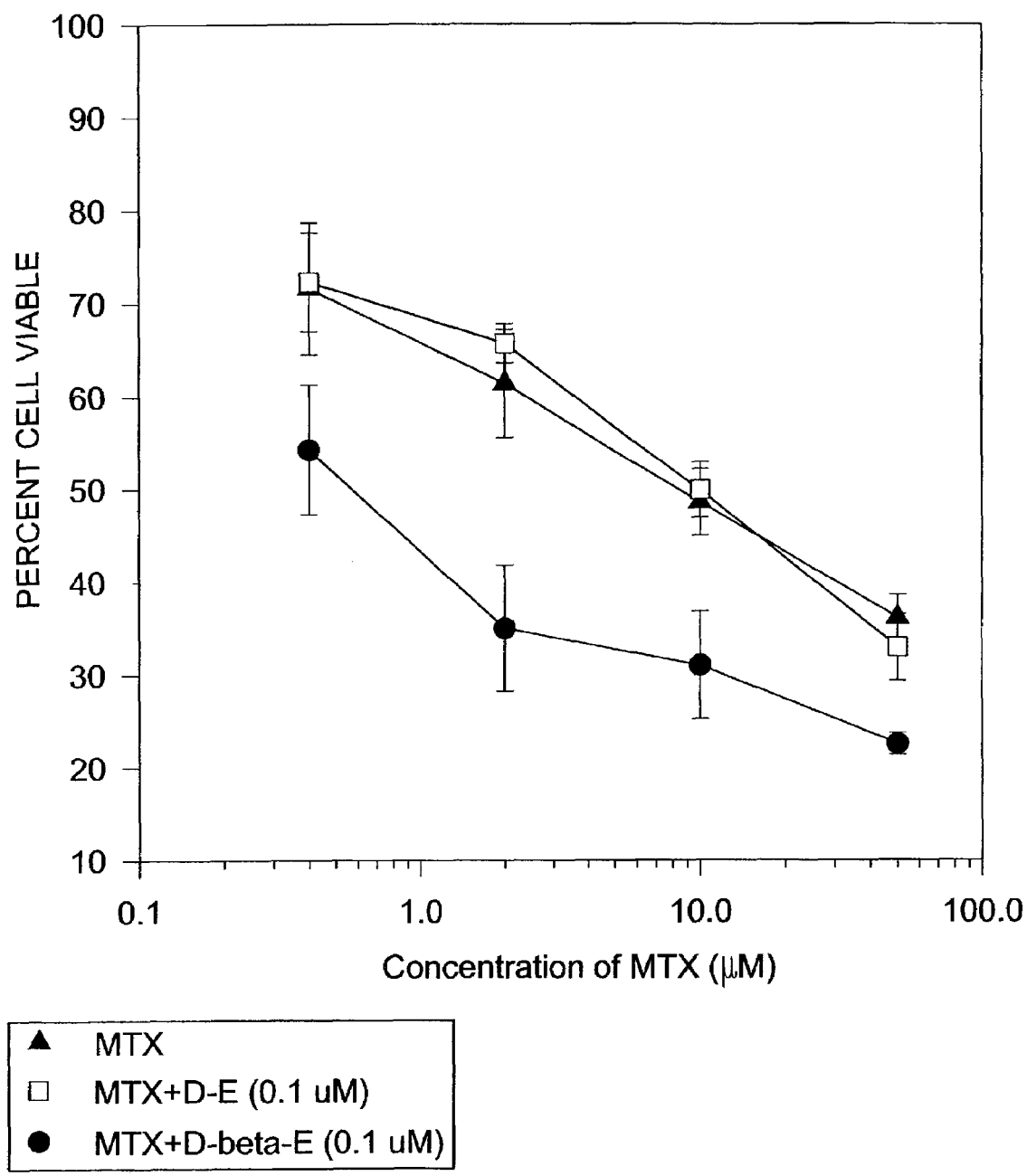
FIG. 13B graphically illustrates the synergistic effect of combining methotrexate (MTX) and the PSMA inhibitor D-β-E (filled circles), on cancer cell viability in vitro. The cytotoxic effect of methotrexate was assessed with and without the presence of the PSMA inhibitor (D-β-E) or PSMA substrate (D-E) using a cell proliferation and viability assay. Tumor cell viability was less when cells were exposed to a combination of methotrexate and the D-β-E inhibitor (filled circles) than when cells were exposed to methotrexate alone (filled triangles) or a combination of methotrexate and the D-E substrate (open squares). The cytotoxic effect of methotrexate was potentiated in the presence of inhibitor at a concentration of 0.1 uM. The $ID_{50}$ of MTX was reduced from around 10 uM to around 0.5 uM in the presence of the PSMA inhibitor (D-β-E) ($ID_{50}/ID_{50}^*=20$), a twenty-fold enhancement of the tumoricidal activity.

FIG. 13B graphically illustrates the synergistic effect of combining methotrexate (MTX) and the PSMA inhibitor, D-β-E, on cancer cell viability in vitro. The cytotoxic effect of methotrexate was assessed with and without the presence of the PSMA inhibitor (D-β-E) or PSMA substrate (D-E) using a cell proliferation and viability assay. The cytotoxic effect of methotrexate was potentiated in the presence of inhibitor at a concentration of 0.1 uM. The $ID_{50}$ of MTX was reduced from around 10 uM to around 0.5 uM in the presence of the PSMA inhibitor (D-β-E) ($ID_{50}/ID_{50}^*=20$), a twenty-fold enhancement of the tumoricidal activity.

These experiments illustrated the therapeutic potential of reduction of a tumor cell viability, combined with selective tumor vascular thrombosis in prostate cancer by targeting cells that express PSMA. The data indicate that PSMA-expressing tumor cells create vascular channels that are lined by tumor cells. Some tumor tissue on the periphery of the tumor often escaped thrombosis, indicating that these tumor cells may survive because they are not in direct contact with tumor blood vessels. However, these peripheral tumor cells are more accessible to cytotoxic drugs delivered by the circulatory system. A combination of therapeutic agents that includes the present Selective Tissue Vascular Thrombogens and an anti-tumor drug may effectively eradicate solid tumors.

Hence, the compositions and methods of the invention are peculiarly suited to treat here-to-fore inaccessible tumor cells within the heart of solid tumors.

The foregoing specification, including the specific embodiments and examples, is intended to be illustrative of the present invention and is not to be taken as limiting. Numerous other variations and modifications can be effected without departing from the true spirit and scope of the present invention.

REFERENCES

The following references, to the extent that they provide exemplary procedural or other details supplementary to those set forth herein, are specifically incorporated herein by reference.

Antibodies: A Laboratory Manual, Cold Spring Harbor Laboratory, 1988.
Abraham et al., Science, 233:545-548, 1986.
Abrams and Oldham, Monoclonal Antibody Therapy of Human Cancer, Foon and Morgan (Eds.), Martinus Nijhoff Publishing, Boston, pp. 103-120, 1985.
Ausubel et al., Current Protocols in Molecular Biology, Greene Publishing Associates and Wiley Interscience, N.Y., 1989.
Bach et al., Biochemistry, 25, 4007-4020, 1986.
Bauer, et al., Vox Sang, 61:156-157, 1991.
Baxter, et al., Micro. Res., 41(1):5-23, 1991.
Bevilacqua, et al., Proc. Natl. Acad. Sci. USA, 84:9238-9242, 1987.
Bhagwat et al., Nature, 316:511-513, 1985.
Bicknell and Harris, Seminars in Cancer Biology, 3:399-407, 1992.
Birembaut et al., J Pathology, 145:283-296, 1985.
Bjomdahl et al., Eur. J. Immunol., 19:881-887, 1989.
Bolhuis et al., J. Immunol., 149:1840-1846, 1992.
Borden et al., Cancer, 65:800-814, 1990.
Brennan et al., Science, 229:81-83, 1985.
Brinkmann et al., Proc. Natl. Acad Sci., 88(19):8616-8620, 1991.
Broze, Seminars in Hematol., 29:159-169, 1992.
Burchell et al., J. Immunol., 131(1):508-513, 1983.
Burrows et al, Cancer Res., 52:5965-5962, 1992.
Burrows et al., Cancer Res., 51:4768-4775, 1991.
Burrows and Thorpe, Proc. Natl. Acad. Sci., USA, 90:8996-9000, 1993.
Burtin et al., Cancer, 31:719-726, 1983.
Byers and Baldwin Immunol., 65:329-335, 1988.
Carter, R. E., A. R. Feldman, et al. (1996). "Prostate-specific membrane antigen is a hydrolase with substrate and pharmacologic characteristics of a neuropeptidase." Proc Natl Acad Sci U S A 93(2): 749-53.
Campbell, In: Monoclonal Antibody Technology, Laboratory Techniques in Biochemistry and Molecular Biology, Vol. 13, Burden and Von Knippenberg (Eds.), Elseview, Amsterdam, pp. 75-83, 1984.
Carmeliet, Mackman et al., 1996. Role of tissue factor in embryonic blood vessel development. Nature 383:73-75.
Chang, S. S., V. E. Reuter et al. (1999). "Five different anti-prostate-specific membrane antigen (PSMA) antibodies confirm PSMA expression in tumor associated neovasculature." Cancer Res Jul 1;59 (13):3192-8.
Chen et al., J. Immunol., 145:8-12, 1990.
Cherwinski et al., J Exp. Med., 166:1229-1244, 1989.
Clark et al., Biochem. Biophys. ACTA, 867:244-251, 1986.
Clark et al., Int. J Cancer, 2:15-17, 1988.
Clark et al., Cancer Res., 51:944-948, 1991.
Colcher et al., Cancer Res., 47:1185 and 4218, 1987.
Collins et al., Proc. Natl. Acad. Sci. USA, 81:4917-4921, 1984.
Cotran et al., J. Exp. Med., 164:661-666, 1986.
Daar et al., Transplantation, 38(3):293-298, 1984.
Davie et al., Biochem., 30:10363-10310, 1991.
Davies and Wlodawer, FASEB J., 9:50-56, 1995.
Davis and Preston, Analytical Biochemistry, 116(2):402-407, 1981.
DeFranco, Nature, 352:754-755, 1991.
deLeij et al., Bispecific Antibodies and Targeted Cellular Cytotoxicity, Romet-Lemonne et al., p. 249, 1991.
Denekamp et al., Brit. J Cancer, 461:711-720, 1982.
Dewerchin et al., Blood, 78(4):1005-1018, 1991.
Di Scipio et al., Biochemistry, 16:5253-5260, 1977.

Dillman et al., Antibody Immunocon. Radiopharm., 1:65-77, 1988.

Drake et al., J Cell Biol., 109:389-95, 1989.

Dustin et al., J. Immunol., 137:245-254, 1986.

Dvorak et al., J. Exp. Med., 174:1275-1278, 1991.

Edgington et al., Thrombosis and Haemostatis, 66(1):67-79, 1991.

Edgington, T. S., C. D. Dickinson, et al. (1997). "The structural basis of function of the TF. VIIa complex in the cellular initiation of coagulation." Thromb Haemost 78(1): 401-5.

Embleton et al, Br. J. Cancer, 63(5):670-674, 1991.

Epenetos et al., Cancer Res., 46:3183-3191, 1986.

Erlanson, D. A., M. Chytil, et al. (1996). "The leucine zipper domain controls the orientation of AP-1 in the NFAT.AP-1.DNA complex." Chem Biol 3(12): 981-91.

Fair, Blood, 62:784-791, 1983.

Fair et al., J. Biol. Chem., 262, 11692-11698, 1987.

Ferrara, J. Cell. Biochem., 47:211-218, 1991.

Flavell et al., Br. J. Cancer, 64(2):274-280, 1991.

Flavell et al., Br. J. Cancer, 65:545-551, 1992.

Folkman, Adv. Cancer Res., 43:175-230, 1985a.

Folkman, In: Important Advances in Oncology, Part I, DeVita et al., (Eds.), J B Lippincott, Philadelphia, pp. 42-62, 1985b.

Fox et al., J. Biol. Resp., 9:499-511, 1990.

Frelinger III, et al., J. Biol. Chem., 265(11):6346-6352, 1990.

Frelinger III, et al., J. Biol. Chem., 266(26):17106-17111, 1991.

French et al., Cancer Res., 51:2358-2361, 1991.

Galfre et al., Methods Enzymol., 73:1-46, 1981.

Galivan, J., T. Johnson, et al. (1987). "The role of folylpolyglutamate synthetase and gamma-glutamyl hydrolase in altering cellular folyl- and antifolylpolyglutamates." Adv Enzyme Regul 26: 147-55.

Gefter et al., Somatic Cell Genet., 3:231-236, 1977.

Geppert et al., Immunological Reviews, 117:5-66, 1990.

Ghose and Blair, CRC Critical Reviews in Therapeutic Drug Carrier Systems, 3:262-359, 1987.

Ghose, CRC Critical Review in Therapeutic Drug Carrier Systems, 3:262-359, 1982.

Ghose et al., Meth. Enzymology, 93:280-333, 1983.

Ghose et al., CRC Critical Reviews in Therapeutic Drug Carrier Systems, 3:262-359, 1987.

Giles et al., Brit. J. Haematol., 69:491-497, 1988.

Glennie et al., J. Immunol., 139:2367-2375, 1987.

Goding, In: Monoclonal Antibodies: Principles and Practice, 2d Ed., Academic Press, Orlando, Fla., pp. 60-61, 65-66, 71-74, 1986.

Gougos and Letarte, J. Immunol., 141:1925-1933, 1988.

Grauer, L. S., K. D. Lawler, et al. (1998). "Identification, purification, and subcellular localization of prostate-specific membrane antigen PSM' protein in the LNCaP prostatic carcinoma cell line." Cancer Res 58(21): 4787-9.

Griffith, E. C., Z. Su, et al. (1997). "Methionine aminopeptidase (type 2) is the common target for angiogenesis inhibitors AGM-1470 and ovalicin." Chem Biol 4(6): 461-71.

Groenewegen et al., Nature, 316:361-363, 1985.

Hagen, et al., Proc. Natl. Acad. Sci. USA., 83:2412-2416, 1986.

Halling et al., Nucl. Acids Res., 13:8019-8033, 1985.

Hammerling, Transplant Rev., 30:64-82, 1976.

Hattey et al., Thrombosis Research, 45(5):485-495, 1987.

Hayward et al., Biological Chemistry, 266(11):7114-7120, 1991.

Hess et al., Transplantation, 6:1232-1240, 1991.

Heston, W. D. (1996). "[Significance of prostate-specific membrane antigen (PSMA). A neurocarboxypeptidase and membrane folate hydrolase]." Urologe A 35(5): 400-7.

Heston, W. D. (1997). "Characterization and glutamyl preferring carboxypeptidase function of prostate specific membrane antigen: a novel folate hydrolase." Urology 49(3A Suppl): 104-12.

Heynen et al., J. Clin. Invest., 94:1098-1112, 1994.

Horoszewicz, J. S., E. Kawinski, et al. (1987). "Monoclonal antibodies to a new antigenic marker in epithelial prostatic cells and serum of prostatic cancer patients." Anticancer Res 7(5B): 927-35.

Huang, X., G. Molema, et al. (1997). "Tumor infarction in mice by antibody-directed targeting of tissue factor to tumor vasculature." Science 275(5299): 547-50.

Ingber, D., T. Fujita, et al. (1990). "Synthetic analogues of fumagillin that inhibit angiogenesis and suppress tumour growth." Nature 348(6301): 555-7.

Israeli, R. S., C. T. Powell, et al. (1993). "Molecular cloning of a complementary DNA encoding a prostate-specific membrane antigen." Cancer Res 53(2): 227-30.

Jackson, P. F., D. C. Cole, et al. (1996). "Design, synthesis, and biological activity of a potent inhibitor of the neuropeptidase N-acetylated alpha-linked acidic dipeptidase." J Med Chem 39(2): 619-22.

Jain, Cancer Meta. Rev., 9(3):253-266, 1990.

June et al., Mol. Cell Biol., 12:4472-4481, 1987.

June et al., Immunology Today, 11(6):211-216, 1990.

Juweid et al., Cancer Res., 52:5144-5153, 1992.

Kandel et al., Cell, 66:1095-1104, 1991.

Kim et al., Nature, 362:841-844, 1993.

Kimura et al., Immunogenetics, 11:373-381, 1983.

Kisiel, J. Biol. Chem., 254(23):12230-12234, 1979.

Klagsburn and Folkman, Angiogenesis Handbook of Experimental Pharmacology, Vol. 95, Sporn and Roberts, Springer-Verlag, Berlin, pp. 549-586, 1990.

Kohler and Milstein, Nature, 256:495-497, 1975.

Kohler and Milstein, Eur. J. Immunol., 6:511-519, 1976.

Krishnaswamy et al., J. Biol. Chem., 267:26110-26120, 1992.

Kyte and Doolittle, J. Mol. Biol., 157(1):105-132, 1982.

Lamb et al., Eur. J. Biochem., 148:265-270, 1985.

Lee et al., Methods in Enzymology, 237:146-164, 1994.

Leith et al., British J. Cancer, 66(2):345-348, 1992.

Liu, H., P. Moy, et al. (1997). "Monoclonal antibodies to the extracellular domain of prostate-specific membrane antigen also react with tumor vascular endothelium." Cancer Res 57(17): 3629-34.

Liu, H., A. K. Rajasekaran, et al. (1998). "Constitutive and antibody-induced internalization of prostate-specific membrane antigen." Cancer Res 58(18): 4055-60.

Liu, S., J. Widom, et al. (1998). "Structure of human methionine aminopeptidase-2 complexed with fumagillin." Science 282(5392): 1324-7.

Lord et al, In: Genetically Engineered Toxins, Frank (Ed.), M. Dekker Publ., p. 183, 1992.

Lowder et al., Blood, 69:199-210, 1987.

Lowe et al., Immunol. Lett., 12:263-269, 1986.

Maeda et al., J. Invest. Derm., 97:183-189, 1991.

Manabe et al., J. Lab. Clin. Med., 104(3):445-454, 1984.

Martin, FASEB J., 9:852-859, 1995.

Massoglia et al., J. Cell. Phys., 132:531-537, 1987.

Mazzocchi et al., Cancer Immunol. Immuother., 32:13-21, 1990.

McGuire, J. J., T. Tsukamoto, et al. (1996). "Exploitation of folate and antifolate polyglutamylation to achieve selective anticancer chemotherapy." Invest New Drugs 14(3): 317-23.
Mignatti et al., J. Cell. Biol., 113:1193-1201, 1991.
Miotti et al., Cancer Res., 65:826, 1985.
Moroi and Aoki, J. Biol. Chem., 251(19):5956-5965, 1976.
Morrissey et al, Cell, 50:129-135, 1987.
Morrissey et al., Thrombosis Research, 52:247-261, 1988.
Morrissey et al., Blood, 81:734-744, 1993.
Mueller et al., Proc. Natl. Acad. Sci. USA, 89:11832-11836, 1992.
Murray, Clauss, Thurston, Stem, Int. J. Radiat. Biol, 60:273-277, 1991.
Nakamura, Prog. Growth Factor Res., 3:67-86, 1991.
Nawroth, Handley, Matsueda, de Waal, Gerlach, Blohm, Stem, J. Exp. Med., 168:637-648, 1988.
Nawroth and Stem, J. Exp. Med., 163:740-745, 1986.
Nelson, Cancer Cells, 3 (5) p163-72, 1991.
Nemerson, Blood, 71(1):1-8, 1988.
Nitta et al., Lancet, 335:368-371, 1990.
O'Brien et al., J. Clin. Invest., 82:206-211, 1988.
O'Connell et al., J. Immunol., 144(2):521-525, 1990.
O'Connor, B. M., R. F. Rotundo, et al. (1991). "Secretion of gamma-glutamyl hydrolase in vitro." Cancer Res 51(15): 3874-81.
O'Hare et al., FEBS Lett., 210:731, 1987.
Ogata, J. Biol. Chem., 256:20678-20685, 1990.
Ogawa, Shreeniwas, Brett, Clauss, Furie, Stem, Brit. J. Haematol., 75:517-524, 1990.
Ohuchida et al., J. Am. Chem. Soc., 103(15):4597-4599, 1981.
Oi and Morrison, Mt. Sinai J. Med., 53(3): 175-180, 1986.
Osborn et al., Cell, 59:1203-1211, 1989.
Osterud et al., Thrombosis Res., 42:323-329, 1986.
Paborsky et al., J. Biol. Chem., 266(32):21911-21916, 1991.
Palleroni et al., Int. J. Cancer, 49:296-302, 1991.
Pasqualini et al., Nat. Biotechnol. 15:542-546, 1997.
Perez et al., Nature, 316:354-356, 1985.
Perez et al., J. Immunol., 137:2069-2072, 1986a.
Perez et al., J. Exp. Med., 163:166-178, 1986b.
Pieterez et al., Antibody Immunoconj. Radiopharm., 1:79-103, 35, 1988.
Pimm et al., J. Cancer Res. Clin. Oncol., 118:367-370, 1992.
Pober et al., J. Exp. Med., 157:1339-1353, 1991.
Pukrittayakamee et al., Mol. Biol. Med., 1: 123-135, 1983.
Qian et al., Cancer Res., 140:3250, 1991.
Rehemtulla et al., Thrombosis and Haemostatis. 65(5):521-527, 1991.
Reisfeld et al., Melanoma Antigens and Antibodies, p. 317, 1982.
Remington's Pharmaceutical Sciences, 16th Ed., Mack Publishing Company, 1980.
Rettig et al., Proc. Natl. Acad. Sci. USA., 89:10832-10836, 1992.
Rhee, M. S., Y. Wang, et al. (1993). "Acquisition of resistance to antifolates caused by enhanced gamma-glutamyl hydrolase activity." Cancer Res 53(10 Suppl): 2227-30.
Rivoltini et al., 3rd Int. Conf. Bispecific Antibodies and Targeted Cellular Cytotoxicity, 1992.
Ruco et al., Am. J. Pathol., 137(5):1163-1171, 1990.
Ruf and Edgington, Proc. Natl. Acad. Sci. USA., 88:8430-8434, 1991a.
Ruf and Edgington, Thrombosis and Haemostasis, 66(5): 529-533, 40, 1991b.
Ruf, et al., J. Biol. Chem., 266, pg. 2158-66, 1991.
Ruf and Edgington, FASEB J., 8:385-390, 1994.
Ruf et al., J. Biol. Chem., 267:22206-22210, 1992a.
Ruf et al., J. Biol. Chem., 267:6375-6381, 1992b.
Ruf et al., J. Biol. Chem., 267(31):22206-22210, 1992c.
Sakai and Kisiel, Thrombosis Res., 60:213-222, 1990.
Sambrook et al., Molecular Cloning, A Laboratory Manual, Cold Spring Harbor Laboratory, N.Y., 1989.
Sambrook et al., Molecular Cloning, A Laboratory Manual, Cold Spring Harbor Laboratory, N.Y., 2001.
Sands, Immunoconjugates and Radiopharmaceuticals, 1:213-226, 1988.
Schutt et al., Immunol. Lett., 19:321-328, 1988.
Segal et al., Int. J. Cancer Suppl., 7 p36-8, 1992.
Serval, V., L. Barbeito, et al. (1990). "Competitive inhibition of N-acetylated-alpha-linked acidic dipeptidase activity by N-acetyl-L-aspartyl-beta-linked L-glutamate." J Neurochem 55(1): 39-46.
Serval, V., T. Galli, et al. (1992). "In vitro and in vivo inhibition of N-acetyl-L-aspartyl-L-glutamate catabolism by N-acylated L-glutamate analogs." J Pharmacol Exp Ther 260(3): 1093-100.
Shankar et al., J. Biol. Chem., 269(19):13936-13941, 1994.
Shen and Tai, J. Biol. Chem., 261(25):11585-11591, 1986.
Shepard et al., J Clin. Immunol., 11:117-127, 1991.
Shockley et al., Ann. N.Y. Acad. Sci., 617:367-382, 1991.
Silver, D. A., I. Pellicer, et al. (1997). "Prostate-specific membrane antigen expression in normal and malignant human tissues [In Process Citation]." Clin Cancer Res 3(1): 81-5.
Smith et al., Br. J. Cancer, 59 (2) p174-8, 1989.
Spiegelberg and Weigle, J. Exp. Med., 121:323-338, 1965.
Staerz et al., Nature, 314(6012):628-631, 1985.
Stevenson et al., Chem. Immunol., 48:126-166, 1990.
Stone, et al., Biochem J., 310:605, 1995.
Street et al., Cell. Immunol., 120:75-81, 1989.
Su, S. L., I. P. Huang, et al. (1995). "Alternatively spliced variants of prostate-specific membrane antigen RNA: ratio of expression as a potential measurement of progression." Cancer Res 55(7): 1441-3.
Sugama et al., Jpn. J. Pharmacol., 55:2, pp. 287-290, 1991.
Sugama et al., J. Cell. Biol., 119(4):935-944, 1992.
ten Cate et al., J. Clin. Invest., 92:1207-1212, 1993.
Thieme et al., Diabetes, 44(1):98-103, 1995.
Thor et al, Cancer Res., 46:3118, 1986.
Tiffany, C. W., G. R. Lapidus et al. (1999) "Characterization of the enzymatic activity of PSM: comparison with brain NAALADase" Prostate Apr 1;39(1):28-35.
Ting et al., J. Immunol., 141:741-748, 1988.
Titus et al., J. Immunol., 138:4018-4022, 1987.
Tomiyama et al., Blood, 79(9):2303-2312, 1992.
Tutt et al., Eur. J Immunol., 21:1351-1358, 1991.
U.S. Pat. No. 4,196,265.
U.S. Pat. No. 4,554,101.
U.S. Pat. No. 4,975,369.
U.S. Pat. No. 5,017,556.
U.S. Pat. No. 5,110,730.
U.S. Pat. No. 5,139,941.
U.S. Pat. No. 5,183,756.
U.S. Pat. No. 5,223,427.
U.S. Pat. No. 5,242,813.
U.S. Pat. No. 5,288,641.
U.S. Pat. No. 5,346,991.
U.S. Pat. No. 5,374,617.
U.S. Pat. No. 5,437,864.
U.S. Pat. No. 5,504,064.
U.S. Pat. No. 5,504,067.
U.S. Pat. No. 5,589,173.
U.S. Pat. No. 5,589,363.
Ugarova et al., J. Biol. Chem., 268(28):21080-21087, 1993.

Vaickus et al., Cancer Invest., 9:195-209, 1991.
Van Duk et al., Int. J. Cancer, 43:344-349, 1989.
Venkateswaran et al., Hybridoma, 11(6):729-739, 1992.
Vitetta et al., Cancer Res., 15:4052-4058, 1991.
Wang et al. (1993). "Two novel HPLC methods which rapidly detect the substrates and cleavage products of gamma-glutamyl hydrolase." Adv Exp Med Biol 338: 655-8.
Wang et al., Biochem. and Biophys. Res. Comm., 177(1): 286-291, 1991.
Wang et al., Int. J Cancer, 54:363-370, 1993.
Warr et al., Blood, 75:1481-1489, 1990.
Watanbe et al., Proc. Natl. Acad. Sci. USA, 86:9456-9460, 1989.
Wawrzynczak and Thorpe In: Immunoconjugates: Antibody Conjugates in Radioimaging and Therapy of Cancer, Vogel (ed.), New York, Oxford University Press, pp. 28-55, 1987.
Weiss et al., Blood, 73:968-975, 1989.
Whittle et al., Nature, 292:472-474, 1981.
Wildgoose et al., Blood, 80:25-28, 1992.
Williams and Esnouf, Biochem. J., 84:52-62, 1962.
Wiman and Collen, Eur. J. Biochem., 78:19-26, 1977.
Wiman, Biochem. J., 191:229-232, 1980.
Winter and Milstein, Nature, 349:293-299, 1991.
WO 94/05328, PCT Application.
WO 94/07515, PCT Application.
WO 94/28017, PCT Application.
WO 96/01653, PCT Application.
Wu et al., Int. J. Pharm., 12:235-239, 1990.
Xu et al., J. Biol. Chem., 267(25): 17792-17803, 1992.
Yamaue et al., Biotherapy, 2:247-259, 1990.
Yao, R., Z. Nimec, et al. (1996). "Identification, cloning, and sequencing of a cDNA coding for rat gamma-glutamyl hydrolase." *J Biol Chem* 271(15): 8525-8.
Yao, R., E. Schneider, et al. (1996). "Human gamma-glutamyl hydrolase: cloning and characterization of the enzyme expressed in vitro." *Proc Natl Acad Sci U S A* 93(19): 10134-8.
Zamarron et al., J. Biol. Chem., 266(24):16193-16199, 1991.
Zhang, L., T. R. Torgerson, et al. (1998). "Preparation of functionally active cell-permeable peptides by single-step ligation of two peptide modules." *Proc Natl Acad Sci U S A* 95(16): 9184-9.

What is claimed:

1. A Tissue Vascular Thrombogen comprising a first Binding Domain associated with a second Tissue Factor Polypeptide Domain, wherein the Binding Domain can bind to a blood vessel within a tissue, and wherein the Tissue Factor Polypeptide Domain consists of SEQ ID NO:4, SEQ ID NO:5, or SEQ ID NO:6.

2. The Tissue Vascular Thrombogen of claim 1 wherein the tissue is a lung, breast, ovary, stomach, pancreas, larynx, esophagus, testes, liver, parotid, biliary tract, colon, rectum, cervix, uterus, endometrium, kidney, bladder, prostate, thyroid, benign prostate hyperplasia, squamous cell carcinoma, adenocarcinoma, small cell carcinoma, melanoma, glioma, or neuroblastoma tumor.

3. The Tissue Vascular Thrombogen of claim 1 wherein the tissue is a prostate tumor.

4. The Tissue Vascular Thrombogen of claim 1 wherein the Binding Domain comprises a ligand for a cellular receptor, a receptor for a cellular ligand or an inhibitor for a membrane-associated protein.

5. The Tissue Vascular Thrombogen of claim 1 wherein the Binding Domain binds to endoglin, integrin, VEGF receptor, or Prostate Specific Membrane Antigen.

6. The Tissue Vascular Thrombogen of claim 1 wherein the Binding Domain is an integrin binding site from fibronectin.

7. The Tissue Vascular Thrombogen of claim 6 wherein the integrin binding site from fibronectin is a polypeptide from SEQ ID NO:8.

8. The Tissue Vascular Thrombogen of claim 1 wherein the Binding Domain is not an antibody.

9. The Tissue Vascular Thrombogen of claim 1 wherein the Binding Domain comprises an inhibitor of prostate specific membrane antigen.

10. The Tissue Vascular Thrombogen of claim 9 wherein the inhibitor of prostate specific membrane antigen comprises Asp-β-Glu, N-succinyl-glutamic acid, quisqalic acid or 2-(phosphonomethyl) pentanedioic acid.

11. The Tissue Vascular Thrombogen of claim 1 comprising SEQ ID NO:9 or SEQ ID NO:10.

12. A therapeutic composition for treating a solid tumor in an animal in need of treatment for the solid tumor, comprising a therapeutically effective amount of a Tissue Vascular Thrombogen and a pharmaceutically acceptable carrier, wherein the Tissue vascular Thrombogen comprises a first Binding Domain associated with a second Tissue Factor Polypeptide Domain, wherein the Binding Domain can bind to blood vessel within a tissue, and wherein the Tissue Factor Polypeptide Domain consists of SEQ ID NO:4, SEQ ID NO:5, or SEQ ID NO:6.

13. The therapeutic composition of claim 12 wherein the tissue is a lung, breast, ovary, stomach, pancreas, larynx, esophagus, testes, liver, parotid, biliary tract, colon, rectum, cervix, uterus, endometrium, kidney, bladder, prostate, thyroid, benign prostate hyperplasia, squamous cell carcinoma, adenocarcinoma, small cell carcinoma, melanoma, glioma, or neuroblastoma tumor.

14. The therapeutic composition of claim 12 wherein the tissue is a prostate tumor.

15. The therapeutic composition of claim 12 wherein the Binding Domain comprises a ligand for a cellular receptor, a receptor for a cellular ligand or an inhibitor for a membrane-associated protein.

16. The therapeutic composition of claim 12 wherein the Binding Domain binds to endoglin, integrin, VEGE receptor, or Prostate Specific Membrane Antigen.

17. The therapeutic composition of claim 12 wherein the Binding Domain is an integrin binding site from fibronectin.

18. The therapeutic composition of claim 17 wherein the integrin binding site from fibronectin is a polypeptide from SEQ ID NO:8.

19. The therapeutic composition of claim 12 wherein the Binding Domain is not an antibody.

20. The therapeutic composition of claim 12 wherein the Binding Domain comprises an inhibitor of prostate specific membrane antigen.

21. The therapeutic composition of claim 20 wherein the inhibitor of prostate specific membrane antigen comprises Asp-β-Glu, N-succinyl-glutamic acid, quisqalic acid, or 2-(phosphonomethyl)pentanedioic acid.

22. The therapeutic composition of claim 12 wherein the pharmaceutically acceptable carrier is a liposome.

23. The therapeutic composition of claim 12 that further comprises a Factor VII or Factor VIIa polypeptide.

24. The therapeutic composition of claim 12 that further comprises a chemotherapeutic agent.

25. The therapeutic composition of claim 12 wherein the Tissue Vascular Thrombogen comprises SEQ ID NO:9 or SEQ ID NO:10.

26. A method of treating a solid tumor in an animal that comprises administering a therapeutically effective amount of a Tissue Vascular Thrombogen comprising a first Binding Domain associated with a second Tissue Factor polypeptide Domain, wherein the Binding Domain can bind to a blood vessel within a tumor, and wherein the Tissue Factor Polypeptide Domain consists of SEQ ID NO:4, SEQ ID NO:5, or SEQ ID NO:6.

27. The method of claim 26 wherein the tumor is a lung, breast, ovary, stomach, pancreas, larynx, esophagus, testes, liver, parotid, biliary tract, colon, rectum, cervix, uterus, endometrium, kidney, bladder, prostate, thyroid, squamous cell carcinoma, adenocarcinoma, small cell carcinoma, melanoma, glioma, or neuroblastoma tumor.

28. The method of claim 26 wherein the tumor is a prostate tumor.

29. The method of claim 28 wherein the thrombosis leads to tumor necrosis.

30. The method of claim 26 wherein the Binding Domain comprises a ligand for a cellular receptor, a receptor for a cellular ligand or an inhibitor for a membrane-associated protein.

31. The method of claim 26 wherein the Binding Domain binds to endoglin, integrin, VEGF receptor, or Prostate Specific Membrane Antigen.

32. The method of claim 26 wherein the Binding Domain is an integrin binding site from fibronectin.

33. The method of claim 32 wherein the integrin binding site from fibronectin is a polypeptide from SEQ ID NO:8.

34. The method of claim 26 wherein the Binding Domain is not an antibody.

35. The method of claim 26 wherein the Binding Domain comprises an inhibitor of prostate specific membrane antigen.

36. The method of claim 35 wherein the inhibitor of prostate specific membrane antigen comprises Asp-β-Glu, N-succinyl-glutamic acid, quisqalic acid or 2-(phosphonomethyl) pentanedioic acid.

37. The method of claim 26 wherein the Tissue Vascular Thrombogen is in a liposome.

38. The method of claim 26 that further comprises administering a therapeutically effective amount of a chemotherapeutic agent.

39. The method of claim 26 wherein the chemotherapeutic agent comprises methotrexate or doxorubicin.

40. The method of claim 26 that further comprises administering a therapeutically effective amount of an inhibitor of prostate specific membrane antigen.

41. The method of claim 40 wherein the inhibitor of prostate specific membrane antigen comprises Asp-β-Glu, N-succinyl-glutamic acid, quisqalic acid or 2-(phosphonomethyl) pentanedioic acid.

42. The method of claim 26 wherein the Selective Tissue Vascular Thrombogen comprises SEQ ID NO:9 or SEQ ID NO:10.

* * * * *

SEQUENCE LISTING

```
<160> NUMBER OF SEQ ID NOS: 36

<210> SEQ ID NO 1
<211> LENGTH: 295
<212> TYPE: PRT
<213> ORGANISM: Homo sapiens

<400> SEQUENCE: 1

Met Glu Thr Pro Ala Trp Pro Arg Val Pro Arg Pro Glu Thr Ala Val
1               5                   10                  15

Ala Arg Thr Leu Leu Leu Gly Trp Val Phe Ala Gln Val Ala Gly Ala
            20                  25                  30

Ser Gly Thr Thr Asn Thr Val Ala Ala Tyr Asn Leu Thr Trp Lys Ser
        35                  40                  45

Thr Asn Phe Lys Thr Ile Leu Glu Trp Glu Pro Lys Pro Val Asn Gln
    50                  55                  60

Val Tyr Thr Val Gln Ile Ser Thr Lys Ser Gly Asp Trp Lys Ser Lys
65                  70                  75                  80

Cys Phe Tyr Thr Thr Asp Thr Glu Cys Asp Leu Thr Asp Glu Ile Val
                85                  90                  95

Lys Asp Val Lys Gln Thr Tyr Leu Ala Arg Val Phe Ser Tyr Pro Ala
            100                 105                 110

Gly Asn Val Glu Ser Thr Gly Ser Ala Gly Glu Pro Leu Tyr Glu Asn
        115                 120                 125

Ser Pro Glu Phe Thr Pro Tyr Leu Glu Thr Asn Leu Gly Gln Pro Thr
    130                 135                 140

Ile Gln Ser Phe Glu Gln Val Gly Thr Lys Val Asn Val Thr Val Glu
145                 150                 155                 160

Asp Glu Arg Thr Leu Val Arg Arg Asn Asn Thr Phe Leu Ser Leu Arg
                165                 170                 175

Asp Val Phe Gly Lys Asp Leu Ile Tyr Thr Leu Tyr Tyr Trp Lys Ser
            180                 185                 190

Ser Ser Ser Gly Lys Lys Thr Ala Lys Thr Asn Thr Asn Glu Phe Leu
        195                 200                 205

Ile Asp Val Asp Lys Gly Glu Asn Tyr Cys Phe Ser Val Gln Ala Val
```

```
            210                 215                 220
Ile Pro Ser Arg Thr Val Asn Arg Lys Ser Thr Asp Ser Pro Val Glu
225                 230                 235                 240

Cys Met Gly Gln Glu Lys Gly Glu Phe Arg Glu Ile Phe Tyr Ile Ile
                245                 250                 255

Gly Ala Val Val Phe Val Val Ile Ile Leu Val Ile Ile Leu Ala Ile
                260                 265                 270

Ser Leu His Lys Cys Arg Lys Ala Gly Val Gly Gln Ser Trp Lys Glu
                275                 280                 285

Asn Ser Pro Leu Asn Val Ser
                290                 295

<210> SEQ ID NO 2
<211> LENGTH: 263
<212> TYPE: PRT
<213> ORGANISM: Homo sapiens

<400> SEQUENCE: 2

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
        50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg Glu Ile Phe Tyr Ile Ile
        210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
                245                 250                 255

Asn Ser Pro Leu Asn Val Ser
                260

<210> SEQ ID NO 3
<211> LENGTH: 219
```

```
<212> TYPE: PRT
<213> ORGANISM: Homo sapiens

<400> SEQUENCE: 3

Ser Gly Thr Thr Asn Thr Val Ala Ala Tyr Asn Leu Thr Trp Lys Ser
  1               5                  10                  15

Thr Asn Phe Lys Thr Ile Leu Glu Trp Glu Pro Lys Pro Val Asn Gln
             20                  25                  30

Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu
210                 215

<210> SEQ ID NO 4
<211> LENGTH: 218
<212> TYPE: PRT
<213> ORGANISM: Homo sapiens

<400> SEQUENCE: 4

Ser Gly Thr Thr Asn Thr Val Ala Ala Tyr Asn Leu Thr Trp Lys Ser
  1               5                  10                  15

Thr Asn Phe Lys Thr Ile Leu Glu Trp Glu Pro Lys Pro Val Asn Gln
             20                  25                  30

Val Tyr Thr Val Gln Ile Ser Thr Lys Ser Gly Asp Trp Lys Ser Lys
         35                  40                  45

Cys Phe Tyr Thr Thr Asp Thr Glu Cys Asp Leu Thr Asp Glu Ile Val
 50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                 85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125
```

Asp Glu Arg Thr Leu Val Arg Arg Asn Asn Thr Phe Leu Ser Leu Arg
            130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
            195                 200                 205

Cys Met Gly Gln Glu Lys Gly Glu Phe Arg
            210                 215

<210> SEQ ID NO 5
<211> LENGTH: 217
<212> TYPE: PRT
<213> ORGANISM: Homo sapiens

<400> SEQUENCE: 5

Thr Thr Asn Thr Val Ala Ala Tyr Asn Leu Thr Trp Lys Ser Thr Asn
1               5                   10                  15

Phe Lys Thr Ile Leu Glu Trp Glu Pro Lys Pro Val Asn Gln Val Tyr
            20                  25                  30

Thr Val Gln Ile Ser Thr Lys Ser Gly Asp Trp Lys Ser Lys Cys Phe
        35                  40                  45

Tyr Thr Thr Asp Thr Glu Cys Asp Leu Thr Asp Glu Ile Val Lys Asp
    50                  55                  60

Val Lys Gln Thr Tyr Leu Ala Arg Val Phe Ser Tyr Pro Ala Gly Asn
65                  70                  75                  80

Val Glu Ser Thr Gly Ser Ala Gly Glu Pro Leu Tyr Glu Asn Ser Pro
                85                  90                  95

Glu Phe Thr Pro Tyr Leu Glu Thr Asn Leu Gly Gln Pro Thr Ile Gln
            100                 105                 110

Ser Phe Glu Gln Val Gly Thr Lys Val Asn Val Thr Val Glu Asp Glu
        115                 120                 125

Arg Thr Leu Val Arg Arg Asn Asn Thr Phe Leu Ser Leu Arg Asp Val
    130                 135                 140

Phe Gly Lys Asp Leu Ile Tyr Thr Leu Tyr Tyr Trp Lys Ser Ser Ser
145                 150                 155                 160

Ser Gly Lys Lys Thr Ala Lys Thr Asn Thr Asn Glu Phe Leu Ile Asp
                165                 170                 175

Val Asp Lys Gly Glu Asn Tyr Cys Phe Ser Val Gln Ala Val Ile Pro
            180                 185                 190

Ser Arg Thr Val Asn Arg Lys Ser Thr Asp Ser Pro Val Glu Cys Met
            195                 200                 205

Gly Gln Glu Lys Gly Glu Phe Arg Glu
            210                 215

<210> SEQ ID NO 6
<211> LENGTH: 216
<212> TYPE: PRT
<213> ORGANISM: Homo sapiens

<400> SEQUENCE: 6

Thr Thr Asn Thr Val Ala Ala Tyr Asn Leu Thr Trp Lys Ser Thr Asn
1               5                   10                  15

```
Phe Lys Thr Ile Leu Glu Trp Glu Pro Lys Pro Val Asn Gln Val Tyr
                 20                  25                  30

Thr Val Gln Ile Ser Thr Lys Ser Gly Asp Trp Lys Ser Lys Cys Phe
             35                  40                  45

Tyr Thr Thr Asp Thr Glu Cys Asp Leu Thr Asp Glu Ile Val Lys Asp
     50                  55                  60

Val Lys Gln Thr Tyr Leu Ala Arg Val Phe Ser Tyr Pro Ala Gly Asn
 65                  70                  75                  80

Val Glu Ser Thr Gly Ser Ala Gly Glu Pro Leu Tyr Glu Asn Ser Pro
                 85                  90                  95

Glu Phe Thr Pro Tyr Leu Glu Thr Asn Leu Gly Gln Pro Thr Ile Gln
            100                 105                 110

Ser Phe Glu Gln Val Gly Thr Lys Val Asn Val Thr Val Glu Asp Glu
            115                 120                 125

Arg Thr Leu Val Arg Arg Asn Asn Thr Phe Leu Ser Leu Arg Asp Val
130                 135                 140

Phe Gly Lys Asp Leu Ile Tyr Thr Leu Tyr Tyr Trp Lys Ser Ser Ser
145                 150                 155                 160

Ser Gly Lys Lys Thr Ala Lys Thr Asn Thr Asn Glu Phe Leu Ile Asp
                165                 170                 175

Val Asp Lys Gly Glu Asn Tyr Cys Phe Ser Val Gln Ala Val Ile Pro
            180                 185                 190

Ser Arg Thr Val Asn Arg Lys Ser Thr Asp Ser Pro Val Glu Cys Met
            195                 200                 205

Gly Gln Glu Lys Gly Glu Phe Arg
        210                 215

<210> SEQ ID NO 7
<211> LENGTH: 22
<212> TYPE: PRT
<213> ORGANISM: Homo sapiens

<400> SEQUENCE: 7

Phe Tyr Ile Ile Gly Ala Val Val Phe Val Ile Ile Leu Val Ile
 1               5                  10                  15

Ile Leu Ala Ile Ser Leu
            20

<210> SEQ ID NO 8
<211> LENGTH: 2320
<212> TYPE: PRT
<213> ORGANISM: Homo sapiens

<400> SEQUENCE: 8

Met Val Gln Pro Gln Ser Pro Val Ala Val Ser Gln Ser Lys Pro Gly
 1               5                  10                  15

Cys Tyr Asp Asn Gly Lys His Tyr Gln Ile Asn Gln Gln Trp Glu Arg
                 20                  25                  30

Thr Tyr Leu Gly Asn Ala Leu Val Cys Thr Cys Tyr Gly Gly Ser Arg
             35                  40                  45

Gly Phe Asn Cys Glu Ser Lys Pro Glu Ala Glu Glu Thr Cys Phe Asp
     50                  55                  60

Lys Tyr Thr Gly Asn Thr Tyr Arg Val Gly Asp Thr Tyr Glu Arg Pro
 65                  70                  75                  80

Lys Asp Ser Met Ile Trp Asp Cys Thr Cys Ile Gly Ala Gly Arg Gly
                 85                  90                  95
```

```
Arg Ile Ser Cys Thr Ile Ala Asn Arg Cys His Glu Gly Gly Gln Ser
            100                 105                 110
Tyr Lys Ile Gly Asp Thr Trp Arg Pro His Glu Thr Gly Gly Tyr
        115                 120                 125
Met Leu Glu Cys Val Cys Leu Gly Asn Gly Lys Gly Glu Trp Thr Cys
    130                 135                 140
Lys Pro Ile Ala Glu Lys Cys Phe Asp His Ala Ala Gly Thr Ser Tyr
145                 150                 155                 160
Val Val Gly Glu Thr Trp Glu Lys Pro Tyr Gln Gly Trp Met Met Val
                165                 170                 175
Asp Cys Thr Cys Leu Gly Glu Gly Ser Gly Arg Ile Thr Cys Thr Ser
                180                 185                 190
Arg Asn Arg Cys Asn Asp Gln Asp Thr Arg Thr Ser Tyr Arg Ile Gly
            195                 200                 205
Asp Thr Trp Ser Lys Lys Asp Asn Arg Gly Asn Leu Leu Gln Cys Ile
        210                 215                 220
Cys Thr Gly Asn Gly Arg Gly Glu Trp Lys Cys Glu Arg His Thr Ser
225                 230                 235                 240
Val Gln Thr Thr Ser Ser Gly Ser Gly Pro Phe Thr Asp Val Arg Ala
                245                 250                 255
Ala Val Tyr Gln Pro Gln Pro His Pro Gln Pro Pro Pro Tyr Gly His
            260                 265                 270
Cys Val Thr Asp Ser Gly Val Val Tyr Ser Val Gly Met Gln Trp Leu
        275                 280                 285
Lys Thr Gln Gly Asn Lys Gln Met Leu Cys Thr Cys Leu Gly Asn Gly
    290                 295                 300
Val Ser Cys Gln Glu Thr Ala Val Thr Gln Thr Tyr Gly Gly Asn Ser
305                 310                 315                 320
Asn Gly Glu Pro Cys Val Leu Pro Phe Thr Tyr Asn Gly Arg Thr Phe
                325                 330                 335
Tyr Ser Cys Thr Thr Glu Gly Arg Gln Asp Gly His Leu Trp Cys Ser
            340                 345                 350
Thr Thr Ser Asn Tyr Glu Gln Asp Gln Lys Tyr Ser Phe Cys Thr Asp
        355                 360                 365
His Thr Val Leu Val Gln Thr Arg Gly Gly Asn Ser Asn Gly Ala Leu
    370                 375                 380
Cys His Phe Pro Phe Leu Tyr Asn Asn His Asn Tyr Thr Asp Cys Thr
385                 390                 395                 400
Ser Glu Gly Arg Arg Asp Asn Met Lys Trp Cys Gly Thr Thr Gln Asn
                405                 410                 415
Tyr Asp Ala Asp Gln Lys Phe Gly Phe Cys Pro Met Ala Ala His Glu
            420                 425                 430
Glu Ile Cys Thr Thr Asn Glu Gly Val Met Tyr Arg Ile Gly Asp Gln
        435                 440                 445
Trp Asp Lys Gln His Asp Met Gly His Met Met Arg Cys Thr Cys Val
    450                 455                 460
Gly Asn Gly Arg Gly Glu Trp Thr Cys Ile Ala Tyr Ser Gln Leu Arg
465                 470                 475                 480
Asp Gln Cys Ile Val Asp Asp Ile Thr Tyr Asn Val Asn Asp Thr Phe
                485                 490                 495
His Lys Arg His Glu Glu Gly His Met Leu Asn Cys Thr Cys Phe Gly
            500                 505                 510
Gln Gly Arg Gly Arg Trp Lys Cys Asp Pro Val Asp Gln Cys Gln Asp
```

-continued

```
            515                 520                 525
Ser Glu Thr Gly Thr Phe Tyr Gln Ile Gly Asp Ser Trp Glu Lys Tyr
        530                 535                 540

Val His Gly Val Arg Tyr Gln Cys Tyr Cys Tyr Gly Arg Gly Ile Gly
545                 550                 555                 560

Glu Trp His Cys Gln Pro Leu Gln Thr Tyr Pro Ser Ser Gly Pro
                    565                 570                 575

Val Glu Val Phe Ile Thr Glu Thr Pro Ser Gln Pro Asn Ser His Pro
                580                 585                 590

Ile Gln Trp Asn Ala Pro Gln Pro Ser His Ile Ser Lys Tyr Ile Leu
            595                 600                 605

Arg Trp Arg Pro Lys Asn Ser Val Gly Arg Trp Lys Glu Ala Thr Ile
        610                 615                 620

Pro Gly His Leu Asn Ser Tyr Thr Ile Lys Gly Leu Lys Pro Gly Val
625                 630                 635                 640

Val Tyr Glu Gly Gln Leu Ile Ser Ile Gln Gln Tyr Gly His Gln Glu
                    645                 650                 655

Val Thr Arg Phe Asp Phe Thr Thr Ser Thr Ser Thr Pro Val Thr
                660                 665                 670

Ser Asn Thr Val Thr Gly Glu Thr Thr Pro Phe Ser Pro Leu Val Ala
            675                 680                 685

Thr Ser Glu Ser Val Thr Glu Ile Thr Ala Ser Ser Phe Val Val Ser
        690                 695                 700

Trp Val Ser Ala Ser Asp Thr Val Ser Gly Phe Arg Val Glu Tyr Glu
705                 710                 715                 720

Leu Ser Glu Glu Gly Asp Glu Pro Gln Tyr Leu Asp Leu Pro Ser Thr
                    725                 730                 735

Ala Thr Ser Val Asn Ile Pro Asp Leu Leu Pro Gly Arg Lys Tyr Ile
                740                 745                 750

Val Asn Val Tyr Gln Ile Ser Glu Asp Gly Glu Gln Ser Leu Ile Leu
            755                 760                 765

Ser Thr Ser Gln Thr Thr Ala Pro Asp Ala Pro Pro Asp Thr Thr Val
        770                 775                 780

Asp Gln Val Asp Asp Thr Ser Ile Val Val Arg Trp Ser Arg Pro Gln
785                 790                 795                 800

Ala Pro Ile Thr Gly Tyr Arg Ile Val Tyr Ser Pro Ser Val Glu Gly
                    805                 810                 815

Ser Ser Thr Glu Leu Asn Leu Pro Glu Thr Ala Asn Ser Val Thr Leu
                820                 825                 830

Ser Asp Leu Gln Pro Gly Val Gln Tyr Asn Ile Thr Ile Tyr Ala Val
            835                 840                 845

Glu Glu Asn Gln Glu Ser Thr Pro Val Val Ile Gln Gln Glu Thr Thr
        850                 855                 860

Gly Thr Pro Arg Ser Asp Thr Val Pro Ser Pro Arg Asp Leu Gln Phe
865                 870                 875                 880

Val Glu Val Thr Asp Val Lys Val Thr Ile Met Trp Thr Pro Pro Glu
                    885                 890                 895

Ser Ala Val Thr Gly Tyr Arg Val Asp Val Ile Pro Val Asn Leu Pro
                900                 905                 910

Gly Glu His Gly Gln Arg Leu Pro Ile Ser Arg Asn Thr Phe Ala Glu
            915                 920                 925

Val Thr Gly Leu Ser Pro Gly Val Thr Tyr Tyr Phe Lys Val Phe Ala
        930                 935                 940
```

```
Val Ser His Gly Arg Glu Ser Lys Pro Leu Thr Ala Gln Gln Thr Thr
945                 950                 955                 960

Lys Leu Asp Ala Pro Thr Asn Leu Gln Phe Val Asn Glu Thr Asp Ser
                965                 970                 975

Thr Val Leu Val Arg Trp Thr Pro Pro Arg Ala Gln Ile Thr Gly Tyr
            980                 985                 990

Arg Leu Thr Val Gly Leu Thr Arg Arg Gly Gln Pro Arg Gln Tyr Asn
        995                 1000                1005

Val Gly Pro Ser Val Ser Lys Tyr Pro Leu Arg Asn Leu Gln Pro Ala
    1010                1015                1020

Ser Glu Tyr Thr Val Ser Leu Val Ala Ile Lys Gly Asn Gln Glu Ser
1025                1030                1035                1040

Pro Lys Ala Thr Gly Val Phe Thr Thr Leu Gln Pro Gly Ser Ser Ile
            1045                1050                1055

Pro Pro Tyr Asn Thr Glu Val Thr Glu Thr Thr Ile Val Ile Thr Trp
            1060                1065                1070

Thr Pro Ala Pro Arg Ile Gly Phe Lys Leu Gly Val Arg Pro Ser Gln
            1075                1080                1085

Gly Gly Glu Ala Pro Arg Glu Val Thr Ser Asp Ser Gly Ser Ile Val
            1090                1095                1100

Val Ser Gly Leu Thr Pro Gly Val Glu Tyr Val Tyr Thr Ile Gln Val
1105                1110                1115                1120

Leu Arg Asp Gly Gln Glu Arg Asp Ala Pro Ile Val Asn Lys Val Val
                1125                1130                1135

Thr Pro Leu Ser Pro Pro Thr Asn Leu His Leu Glu Ala Asn Pro Asp
            1140                1145                1150

Thr Gly Val Leu Thr Val Ser Trp Glu Arg Ser Thr Thr Pro Asp Ile
            1155                1160                1165

Thr Gly Tyr Arg Ile Thr Thr Thr Pro Thr Asn Gly Gln Gln Gly Asn
            1170                1175                1180

Ser Leu Glu Glu Val Val His Ala Asp Gln Ser Ser Cys Thr Phe Asp
1185                1190                1195                1200

Asn Leu Ser Pro Gly Leu Glu Tyr Asn Val Ser Val Tyr Thr Val Lys
            1205                1210                1215

Asp Asp Lys Glu Ser Val Pro Ile Ser Asp Thr Ile Ile Pro Ala Val
            1220                1225                1230

Pro Pro Pro Thr Asp Leu Arg Phe Thr Asn Ile Gly Pro Asp Thr Met
            1235                1240                1245

Arg Val Thr Trp Ala Pro Pro Ser Ile Asp Leu Thr Asn Phe Leu
1250                1255                1260

Val Arg Tyr Ser Pro Val Lys Asn Glu Glu Asp Val Ala Glu Leu Ser
1265                1270                1275                1280

Ile Ser Pro Ser Asp Asn Ala Val Val Leu Thr Asn Leu Leu Pro Gly
            1285                1290                1295

Thr Glu Tyr Val Val Ser Val Ser Ser Val Tyr Glu Gln His Glu Ser
            1300                1305                1310

Thr Pro Leu Arg Gly Arg Gln Lys Thr Gly Leu Asp Ser Pro Thr Gly
            1315                1320                1325

Ile Asp Phe Ser Asp Ile Thr Ala Asn Ser Phe Thr Val His Trp Ile
            1330                1335                1340

Ala Pro Arg Ala Thr Ile Thr Gly Tyr Arg Ile Arg His His Pro Glu
1345                1350                1355                1360
```

-continued

```
His Phe Ser Gly Arg Pro Arg Glu Asp Arg Val Pro His Ser Arg Asn
            1365                1370                1375

Ser Ile Thr Leu Thr Asn Leu Thr Pro Gly Thr Glu Tyr Val Val Ser
        1380                1385                1390

Ile Val Ala Leu Asn Gly Arg Glu Glu Ser Pro Leu Leu Ile Gly Gln
    1395                1400                1405

Gln Ser Thr Val Ser Asp Val Pro Arg Asp Leu Glu Val Val Ala Ala
1410                1415                1420

Thr Pro Thr Ser Leu Leu Ile Ser Trp Asp Ala Pro Ala Val Thr Val
1425                1430                1435                1440

Arg Tyr Tyr Arg Ile Thr Tyr Gly Glu Thr Gly Gly Asn Ser Pro Val
                1445                1450                1455

Gln Glu Phe Thr Val Pro Gly Ser Lys Ser Thr Ala Thr Ile Ser Gly
            1460                1465                1470

Leu Lys Pro Gly Val Asp Tyr Thr Ile Thr Val Tyr Ala Val Thr Gly
        1475                1480                1485

Arg Gly Asp Ser Pro Ala Ser Ser Lys Pro Ile Ser Ile Asn Tyr Arg
    1490                1495                1500

Thr Glu Ile Asp Lys Pro Ser Gln Met Gln Val Thr Asp Val Gln Asp
1505                1510                1515                1520

Asn Ser Ile Ser Val Lys Trp Leu Pro Ser Ser Ser Pro Val Thr Gly
                1525                1530                1535

Tyr Arg Val Thr Thr Thr Pro Lys Asn Gly Pro Gly Pro Thr Lys Thr
            1540                1545                1550

Lys Thr Ala Gly Pro Asp Gln Thr Glu Met Thr Ile Glu Gly Leu Gln
        1555                1560                1565

Pro Thr Val Glu Tyr Val Val Ser Val Tyr Ala Gln Asn Pro Ser Gly
    1570                1575                1580

Glu Ser Gln Pro Leu Val Gln Thr Ala Val Thr Asn Ile Asp Arg Pro
1585                1590                1595                1600

Lys Gly Leu Ala Phe Thr Asp Val Asp Val Asp Ser Ile Lys Ile Ala
                1605                1610                1615

Trp Glu Ser Pro Gln Gly Gln Val Ser Arg Tyr Arg Val Thr Tyr Ser
            1620                1625                1630

Ser Pro Glu Asp Gly Ile His Glu Leu Phe Pro Ala Pro Asp Gly Glu
        1635                1640                1645

Glu Asp Thr Ala Glu Leu Gln Gly Leu Arg Pro Gly Ser Glu Tyr Thr
    1650                1655                1660

Val Ser Val Val Ala Leu His Asp Asp Met Glu Ser Gln Pro Leu Ile
1665                1670                1675                1680

Gly Thr Gln Ser Thr Ala Ile Pro Ala Pro Thr Asp Leu Lys Phe Thr
                1685                1690                1695

Gln Val Thr Pro Thr Ser Leu Ser Ala Gln Trp Thr Pro Pro Asn Val
            1700                1705                1710

Gln Leu Thr Gly Tyr Arg Val Arg Val Thr Pro Lys Glu Lys Thr Gly
        1715                1720                1725

Pro Met Lys Glu Ile Asn Leu Ala Pro Asp Ser Ser Ser Val Val Val
    1730                1735                1740

Ser Gly Leu Met Val Ala Thr Lys Tyr Glu Val Ser Val Tyr Ala Leu
1745                1750                1755                1760

Lys Asp Thr Leu Thr Ser Arg Pro Ala Gln Gly Val Val Thr Thr Leu
                1765                1770                1775

Glu Asn Val Ser Pro Pro Arg Arg Ala Arg Val Thr Asp Ala Thr Glu
```

-continued

```
                1780            1785            1790
Thr Thr Ile Thr Ile Ser Trp Arg Thr Lys Thr Glu Thr Ile Thr Gly
    1795            1800            1805

Phe Gln Val Asp Ala Val Pro Ala Asn Gly Gln Thr Pro Ile Gln Arg
    1810            1815            1820

Thr Ile Lys Pro Asp Val Arg Ser Tyr Thr Ile Thr Gly Leu Gln Pro
1825            1830            1835            1840

Gly Thr Asp Tyr Lys Ile Tyr Leu Tyr Thr Leu Asn Asp Asn Ala Arg
                1845            1850            1855

Ser Ser Pro Val Val Ile Asp Ala Ser Thr Ala Ile Asp Ala Pro Ser
    1860            1865            1870

Asn Leu Arg Phe Leu Ala Thr Thr Pro Asn Ser Leu Leu Val Ser Trp
    1875            1880            1885

Gln Pro Pro Arg Ala Arg Ile Thr Gly Tyr Ile Ile Lys Tyr Glu Lys
    1890            1895            1900

Pro Gly Ser Pro Pro Arg Glu Val Val Pro Arg Pro Arg Pro Gly Val
1905            1910            1915            1920

Thr Glu Ala Thr Ile Thr Gly Leu Glu Pro Gly Thr Glu Tyr Thr Ile
                1925            1930            1935

Tyr Val Ile Ala Leu Lys Asn Asn Gln Lys Ser Glu Pro Leu Ile Gly
                1940            1945            1950

Arg Lys Lys Thr Asp Glu Leu Pro Gln Leu Val Thr Leu Pro His Pro
                1955            1960            1965

Asn Leu His Gly Pro Glu Ile Leu Asp Val Pro Ser Thr Val Gln Lys
    1970            1975            1980

Thr Pro Phe Val Thr His Pro Gly Tyr Asp Thr Gly Asn Gly Ile Gln
1985            1990            1995            2000

Leu Pro Gly Thr Ser Gly Gln Gln Pro Ser Val Gly Gln Gln Met Ile
                2005            2010            2015

Phe Glu Glu His Gly Phe Arg Arg Thr Thr Pro Pro Thr Thr Ala Thr
                2020            2025            2030

Pro Ile Arg His Arg Pro Arg Pro Tyr Pro Pro Asn Val Gly Gln Glu
    2035            2040            2045

Ala Leu Ser Gln Thr Thr Ile Ser Trp Ala Pro Phe Gln Asp Thr Ser
    2050            2055            2060

Glu Tyr Ile Ile Ser Cys His Pro Val Gly Thr Asp Glu Glu Pro Leu
2065            2070            2075            2080

Gln Phe Arg Val Pro Gly Thr Ser Thr Ser Ala Thr Leu Thr Gly Leu
                2085            2090            2095

Thr Arg Gly Ala Thr Tyr Asn Val Ile Val Glu Ala Leu Lys Asp Gln
                2100            2105            2110

Gln Arg His Lys Val Arg Glu Glu Val Val Thr Val Gly Asn Ser Val
    2115            2120            2125

Asn Glu Gly Leu Asn Gln Pro Thr Asp Asp Ser Cys Phe Asp Pro Tyr
    2130            2135            2140

Thr Val Ser His Tyr Ala Val Gly Asp Glu Trp Glu Arg Met Ser Glu
2145            2150            2155            2160

Ser Gly Phe Lys Leu Leu Cys Gln Cys Leu Gly Phe Gly Ser Gly His
                2165            2170            2175

Phe Arg Cys Asp Ser Ser Arg Trp Cys His Asp Asn Gly Val Asn Tyr
    2180            2185            2190

Lys Ile Gly Glu Lys Trp Asp Arg Gln Gly Glu Asn Gly Gln Met Met
    2195            2200            2205
```

Ser Cys Thr Cys Leu Gly Asn Gly Lys Gly Glu Phe Lys Cys Asp Pro
    2210                2215                2220

His Glu Ala Thr Cys Tyr Asp Asp Gly Lys Thr Tyr His Val Gly Glu
2225                2230                2235                2240

Gln Trp Gln Lys Glu Tyr Leu Gly Ala Ile Cys Ser Cys Thr Cys Phe
                2245                2250                2255

Gly Gly Gln Arg Gly Trp Arg Cys Asp Asn Cys Arg Arg Pro Gly Gly
            2260                2265                2270

Glu Pro Ser Pro Glu Gly Thr Thr Gly Gln Ser Tyr Asn Gln Tyr Ser
        2275                2280                2285

Gln Arg Tyr His Gln Arg Thr Asn Thr Asn Val Asn Cys Pro Ile Glu
    2290                2295                2300

Cys Phe Met Pro Leu Asp Val Gln Ala Asp Arg Glu Asp Ser Arg Glu
2305                2310                2315                2320

<210> SEQ ID NO 9
<211> LENGTH: 599
<212> TYPE: PRT
<213> ORGANISM: Homo sapiens

<400> SEQUENCE: 9

Met Arg Gly Ser His His His His His His Gly Ser Gly Ser Ser Thr
1               5                   10                  15

Pro Pro Pro Thr Asp Leu Arg Phe Thr Asn Ile Gly Pro Asp Thr Met
                20                  25                  30

Arg Val Thr Trp Ala Pro Pro Ser Ile Asp Leu Thr Asn Phe Leu
            35                  40                  45

Val Arg Tyr Ser Pro Val Lys Asn Glu Glu Asp Val Ala Glu Leu Ser
    50                  55                  60

Ile Ser Pro Ser Asp Asn Ala Val Val Leu Thr Asn Leu Leu Pro Gly
65                  70                  75                  80

Thr Glu Tyr Val Val Ser Val Ser Ser Val Tyr Glu Gln His Glu Ser
                85                  90                  95

Thr Pro Leu Arg Gly Arg Gln Lys Thr Gly Leu Asp Ser Pro Thr Gly
                100                 105                 110

Ile Asp Phe Ser Asp Ile Thr Ala Asn Ser Phe Thr Val His Trp Ile
            115                 120                 125

Ala Pro Arg Ala Thr Ile Thr Gly Tyr Arg Ile Arg His His Pro Glu
    130                 135                 140

His Phe Ser Gly Arg Pro Arg Glu Asp Arg Val Pro His Ser Arg Asn
145                 150                 155                 160

Ser Ile Thr Leu Thr Asn Leu Thr Pro Gly Thr Glu Tyr Val Val Ser
                165                 170                 175

Ile Val Ala Leu Asn Gly Arg Glu Glu Ser Pro Leu Leu Ile Gly Gln
            180                 185                 190

Gln Ser Thr Val Ser Asp Val Pro Arg Asp Leu Glu Val Val Ala Ala
    195                 200                 205

Thr Pro Thr Ser Leu Leu Ile Ser Trp Asp Ala Pro Ala Val Thr Val
    210                 215                 220

Arg Tyr Tyr Arg Ile Thr Tyr Gly Glu Thr Gly Gly Asn Ser Pro Val
225                 230                 235                 240

Gln Glu Phe Thr Val Pro Gly Ser Lys Ser Thr Ala Thr Ile Ser Gly
                245                 250                 255

Leu Lys Pro Gly Val Asp Tyr Thr Ile Thr Val Tyr Ala Val Thr Gly

-continued

```
                    260                 265                 270
Arg Gly Asp Ser Pro Ala Ser Ser Lys Pro Ile Ser Ile Asn Tyr Arg
                275                 280                 285

Thr Glu Ile Asp Lys Pro Ser Gln Met Gln Val Thr Asp Val Gln Asp
            290                 295                 300

Asn Ser Ile Ser Val Lys Trp Leu Pro Ser Ser Pro Val Thr Gly
305                 310                 315                 320

Tyr Arg Val Thr Thr Thr Pro Lys Asn Gly Pro Gly Pro Thr Lys Thr
                325                 330                 335

Lys Thr Ala Gly Pro Asp Gln Thr Glu Met Thr Ile Glu Gly Leu Gln
            340                 345                 350

Pro Thr Val Glu Tyr Val Val Ser Val Tyr Ala Gln Asn Pro Ser Gly
        355                 360                 365

Glu Ser Gln Pro Leu Val Gln Thr Ala Val Thr Ser Ser Gly Thr
    370                 375                 380

Thr Asn Thr Val Ala Ala Tyr Asn Leu Thr Trp Lys Ser Thr Asn Phe
385                 390                 395                 400

Lys Thr Ile Leu Glu Trp Glu Pro Lys Pro Val Asn Gln Val Tyr Thr
                405                 410                 415

Val Gln Ile Ser Thr Lys Ser Gly Asp Trp Lys Ser Lys Cys Phe Tyr
            420                 425                 430

Thr Thr Asp Thr Glu Cys Asp Leu Thr Asp Glu Ile Val Lys Asp Val
        435                 440                 445

Lys Gln Thr Tyr Leu Ala Arg Val Phe Ser Tyr Pro Ala Gly Asn Val
    450                 455                 460

Glu Ser Thr Gly Ser Ala Gly Glu Pro Leu Tyr Glu Asn Ser Pro Glu
465                 470                 475                 480

Phe Thr Pro Tyr Leu Glu Thr Asn Leu Gly Gln Pro Thr Ile Gln Ser
                485                 490                 495

Phe Glu Gln Val Gly Thr Lys Val Asn Val Thr Val Glu Asp Glu Arg
            500                 505                 510

Thr Leu Val Arg Arg Asn Asn Thr Phe Leu Ser Leu Arg Asp Val Phe
        515                 520                 525

Gly Lys Asp Leu Ile Tyr Thr Leu Tyr Tyr Trp Lys Ser Ser Ser Ser
    530                 535                 540

Gly Lys Lys Thr Ala Lys Thr Asn Thr Asn Glu Phe Leu Ile Asp Val
545                 550                 555                 560

Asp Lys Gly Glu Asn Tyr Cys Phe Ser Val Gln Ala Val Ile Pro Ser
                565                 570                 575

Arg Thr Val Asn Arg Lys Ser Thr Asp Ser Pro Val Glu Cys Met Gly
            580                 585                 590

Gln Glu Lys Gly Glu Phe Arg
        595
```

<210> SEQ ID NO 10
<211> LENGTH: 330
<212> TYPE: PRT
<213> ORGANISM: Homo sapiens

<400> SEQUENCE: 10

```
Met Arg Gly Ser His His His His His His Gly Ser Gly Ser Ser Thr
 1               5                  10                  15

Val Ser Asp Val Pro Arg Asp Leu Glu Val Val Ala Ala Thr Pro Thr
            20                  25                  30
```

-continued

Ser Leu Leu Ile Ser Trp Asp Ala Pro Ala Val Thr Val Arg Tyr Tyr
         35                  40                  45

Arg Ile Thr Tyr Gly Glu Thr Gly Gly Asn Ser Pro Val Gln Glu Phe
 50                  55                  60

Thr Val Pro Gly Ser Lys Ser Thr Ala Thr Ile Ser Gly Leu Lys Pro
 65                  70                  75                  80

Gly Val Asp Tyr Thr Ile Thr Val Tyr Ala Val Thr Gly Arg Gly Asp
                 85                  90                  95

Ser Pro Ala Ser Ser Lys Pro Ile Ser Ile Asn Tyr Arg Thr Ser Ser
                100                 105                 110

Ser Gly Thr Thr Asn Thr Val Ala Ala Tyr Asn Leu Thr Trp Lys Ser
            115                 120                 125

Thr Asn Phe Lys Thr Ile Leu Glu Trp Glu Pro Lys Pro Val Asn Gln
        130                 135                 140

Val Tyr Thr Val Gln Ile Ser Thr Lys Ser Gly Asp Trp Lys Ser Lys
145                 150                 155                 160

Cys Phe Tyr Thr Thr Asp Thr Glu Cys Asp Leu Thr Asp Glu Ile Val
                165                 170                 175

Lys Asp Val Lys Gln Thr Tyr Leu Ala Arg Val Phe Ser Tyr Pro Ala
                180                 185                 190

Gly Asn Val Glu Ser Thr Gly Ser Ala Gly Glu Pro Leu Tyr Glu Asn
            195                 200                 205

Ser Pro Glu Phe Thr Pro Tyr Leu Glu Thr Asn Leu Gly Gln Pro Thr
        210                 215                 220

Ile Gln Ser Phe Glu Gln Val Gly Thr Lys Val Asn Val Thr Val Glu
225                 230                 235                 240

Asp Glu Arg Thr Leu Val Arg Arg Asn Asn Thr Phe Leu Ser Leu Arg
                245                 250                 255

Asp Val Phe Gly Lys Asp Leu Ile Tyr Thr Leu Tyr Tyr Trp Lys Ser
                260                 265                 270

Ser Ser Ser Gly Lys Lys Thr Ala Lys Thr Asn Thr Asn Glu Phe Leu
            275                 280                 285

Ile Asp Val Asp Lys Gly Glu Asn Tyr Cys Phe Ser Val Gln Ala Val
        290                 295                 300

Ile Pro Ser Arg Thr Val Asn Arg Lys Ser Thr Asp Ser Pro Val Glu
305                 310                 315                 320

Cys Met Gly Gln Glu Lys Gly Glu Phe Arg
                325                 330

<210> SEQ ID NO 11
<211> LENGTH: 24
<212> TYPE: DNA
<213> ORGANISM: Artificial Sequence
<220> FEATURE:
<223> OTHER INFORMATION: A primer.

<400> SEQUENCE: 11
caccaacaac ttgcatctgg aggc                                    24

<210> SEQ ID NO 12
<211> LENGTH: 24
<212> TYPE: DNA
<213> ORGANISM: Artificial Sequence
<220> FEATURE:
<223> OTHER INFORMATION: A primer.

<400> SEQUENCE: 12

-continued

```
aacattgggt ggtgtccact gggc                                          24

<210> SEQ ID NO 13
<211> LENGTH: 48
<212> TYPE: DNA
<213> ORGANISM: Artificial Sequence
<220> FEATURE:
<223> OTHER INFORMATION: A primer.

<400> SEQUENCE: 13
accatcacgg atccggggtc gtcgacacct cctcccactg acctgcga               48

<210> SEQ ID NO 14
<211> LENGTH: 40
<212> TYPE: DNA
<213> ORGANISM: Artificial Sequence
<220> FEATURE:
<223> OTHER INFORMATION: A primer.

<400> SEQUENCE: 14
ggtaccggag gagctcgtta cctgcagtct gaaccagagg                         40

<210> SEQ ID NO 15
<211> LENGTH: 36
<212> TYPE: DNA
<213> ORGANISM: Artificial Sequence
<220> FEATURE:
<223> OTHER INFORMATION: A primer.

<400> SEQUENCE: 15
acgagctcct ccggtaccac aaatactgtg ggcagc                             36

<210> SEQ ID NO 16
<211> LENGTH: 20
<212> TYPE: DNA
<213> ORGANISM: Artificial Sequence
<220> FEATURE:
<223> OTHER INFORMATION: A primer.

<400> SEQUENCE: 16
tctgcgttct gatttaatct                                               20

<210> SEQ ID NO 17
<211> LENGTH: 4
<212> TYPE: PRT
<213> ORGANISM: Artificial Sequence
<220> FEATURE:
<223> OTHER INFORMATION: A RGDS peptide.

<400> SEQUENCE: 17

Arg Gly Asp Ser
 1

<210> SEQ ID NO 18
<211> LENGTH: 19
<212> TYPE: PRT
<213> ORGANISM: Artificial Sequence
<220> FEATURE:
<223> OTHER INFORMATION: A peptide containing a poly His tag and a
      processing protease (Fxa) cleavage site followed by a cysteine.
<220> FEATURE:
<221> NAME/KEY: SITE
<222> LOCATION: (1)...(19)
<223> OTHER INFORMATION: Xaa = any amino acid.

<400> SEQUENCE: 18

Met Xaa Xaa Xaa His His His His His His Xaa Xaa Xaa Xaa Ile Glu
```

-continued

```
1               5                  10                  15
Gly Arg Cys

<210> SEQ ID NO 19
<211> LENGTH: 5
<212> TYPE: PRT
<213> ORGANISM: Artificial Sequence
<220> FEATURE:
<223> OTHER INFORMATION: A lysine containing linker.

<400> SEQUENCE: 19

Lys Ser Gly Gly Gly
 1               5

<210> SEQ ID NO 20
<211> LENGTH: 21
<212> TYPE: DNA
<213> ORGANISM: Artificial Sequence
<220> FEATURE:
<223> OTHER INFORMATION: A primer.

<400> SEQUENCE: 20
actacaaata ctgtggcagc a                                              21

<210> SEQ ID NO 21
<211> LENGTH: 33
<212> TYPE: DNA
<213> ORGANISM: Artificial Sequence
<220> FEATURE:
<223> OTHER INFORMATION: A primer.

<400> SEQUENCE: 21
tttaagcttt cacgtgccca tacactctac cgg                                 33

<210> SEQ ID NO 22
<211> LENGTH: 50
<212> TYPE: DNA
<213> ORGANISM: Artificial Sequence
<220> FEATURE:
<223> OTHER INFORMATION: A primer.

<400> SEQUENCE: 22
aaatggatcc tggtgcctag gggcccggga ctacaaatac tgtggcagca               50

<210> SEQ ID NO 23
<211> LENGTH: 5
<212> TYPE: PRT
<213> ORGANISM: Artificial Sequence
<220> FEATURE:
<223> OTHER INFORMATION: A thrombin cleavage site.

<400> SEQUENCE: 23

Val Pro Arg Gly Ser
 1               5

<210> SEQ ID NO 24
<211> LENGTH: 15
<212> TYPE: PRT
<213> ORGANISM: Artificial Sequence
<220> FEATURE:
<223> OTHER INFORMATION: A linker sequence with three repeats of
      Gly4Ser.

<400> SEQUENCE: 24

Gly Gly Gly Gly Ser Gly Gly Gly Gly Ser Gly Gly Gly Gly Ser
 1               5                  10                  15
```

<210> SEQ ID NO 25
<211> LENGTH: 37
<212> TYPE: DNA
<213> ORGANISM: Artificial Sequence
<220> FEATURE:
<223> OTHER INFORMATION: A primer.

<400> SEQUENCE: 25
gatcttggtc cctaggggat ccgcagaacc aatgcct                     37

<210> SEQ ID NO 26
<211> LENGTH: 36
<212> TYPE: DNA
<213> ORGANISM: Artificial Sequence
<220> FEATURE:
<223> OTHER INFORMATION: A primer.

<400> SEQUENCE: 26
cactcgctaa acttcagtca atacctctgg tatact                      36

<210> SEQ ID NO 27
<211> LENGTH: 36
<212> TYPE: DNA
<213> ORGANISM: Artificial Sequence
<220> FEATURE:
<223> OTHER INFORMATION: A primer.

<400> SEQUENCE: 27
ggtaccggag gaggcggttc aggtggtgga ggttca                      36

<210> SEQ ID NO 28
<211> LENGTH: 16
<212> TYPE: DNA
<213> ORGANISM: Artificial Sequence
<220> FEATURE:
<223> OTHER INFORMATION: A primer.

<400> SEQUENCE: 28
ggaggtggag gttctc                                            16

<210> SEQ ID NO 29
<211> LENGTH: 23
<212> TYPE: DNA
<213> ORGANISM: Artificial Sequence
<220> FEATURE:
<223> OTHER INFORMATION: A primer.

<400> SEQUENCE: 29
tctgcggatc ccctagggac caa                                    23

<210> SEQ ID NO 30
<211> LENGTH: 36
<212> TYPE: DNA
<213> ORGANISM: Artificial Sequence
<220> FEATURE:
<223> OTHER INFORMATION: A primer.

<400> SEQUENCE: 30
aggtattgac tgaagtttag cgagtgaggc attggt                      36

<210> SEQ ID NO 31
<211> LENGTH: 36
<212> TYPE: DNA
<213> ORGANISM: Artificial Sequence
<220> FEATURE:

```
<223> OTHER INFORMATION: A primer.

<400> SEQUENCE: 31
ccacctgaac cgcctcctcc ggtaccagta taccag                              36

<210> SEQ ID NO 32
<211> LENGTH: 30
<212> TYPE: DNA
<213> ORGANISM: Artificial Sequence
<220> FEATURE:
<223> OTHER INFORMATION: A primer.

<400> SEQUENCE: 32
ccgggagaac ctccacctcc tgaacctcca                                     30

<210> SEQ ID NO 33
<211> LENGTH: 20
<212> TYPE: DNA
<213> ORGANISM: Artificial Sequence
<220> FEATURE:
<223> OTHER INFORMATION: A primer.

<400> SEQUENCE: 33
accacggtct cgattacggc                                                20

<210> SEQ ID NO 34
<211> LENGTH: 20
<212> TYPE: DNA
<213> ORGANISM: Artificial Sequence
<220> FEATURE:
<223> OTHER INFORMATION: A primer.

<400> SEQUENCE: 34
actactgctg aacggcgtcg                                                20

<210> SEQ ID NO 35
<211> LENGTH: 32
<212> TYPE: DNA
<213> ORGANISM: Artificial Sequence
<220> FEATURE:
<223> OTHER INFORMATION: A primer.

<400> SEQUENCE: 35
cacacaggat ccgccgccga ggccggcatc ac                                  32

<210> SEQ ID NO 36
<211> LENGTH: 32
<212> TYPE: DNA
<213> ORGANISM: Artificial Sequence
<220> FEATURE:
<223> OTHER INFORMATION: A primer.

<400> SEQUENCE: 36
cacacaggta ccctgctgaa cggcgtcgag cg                                  32
```